United States Patent
Stassinopoulos

(10) Patent No.: US 7,655,392 B2
(45) Date of Patent: Feb. 2, 2010

(54) QUENCHING METHODS FOR RED BLOOD CELL INACTIVATION PROCESS

(75) Inventor: Adonis Stassinopoulos, Dublin, CA (US)

(73) Assignee: Cerus Corporation, Concord, CA (US)

( * ) Notice: Subject to any disclaimer, the term of this patent is extended or adjusted under 35 U.S.C. 154(b) by 498 days.

(21) Appl. No.: 11/264,195

(22) Filed: Oct. 31, 2005

(65) Prior Publication Data

US 2006/0115466 A1    Jun. 1, 2006

Related U.S. Application Data

(60) Provisional application No. 60/623,177, filed on Oct. 29, 2004.

(51) Int. Cl.
*A01N 1/00* (2006.01)
(52) U.S. Cl. .......................................... 435/2
(58) Field of Classification Search ................... None
See application file for complete search history.

(56) References Cited

U.S. PATENT DOCUMENTS

| | | | |
|---|---|---|---|
| 2,402,665 | A | 6/1946 | Pepper et al. |
| 4,252,645 | A | 2/1981 | Marconi et al. |
| 4,337,269 | A | 6/1982 | Berke et al. |
| 4,727,027 | A | 2/1988 | Wiesehahn et al. |
| 4,748,120 | A | 5/1988 | Wiesehahn et al. |
| 4,944,920 | A | 7/1990 | Rubinstein |
| 4,971,760 | A | 11/1990 | Rubinstein |
| 5,055,485 | A | 10/1991 | Geacintov et al. |
| 5,094,960 | A | 3/1992 | Bonomo |
| 5,120,649 | A | 6/1992 | Horowitz et al. |
| 5,232,844 | A | 8/1993 | Horowitz et al. |
| 5,281,579 | A | 1/1994 | Estep |
| 5,418,130 | A | 5/1995 | Platz et al. |
| 5,559,250 | A | 9/1996 | Cook et al. |
| 5,587,490 | A | 12/1996 | Goodrich, Jr. et al. |
| 5,591,350 | A | 1/1997 | Piechocki et al. |
| 5,601,730 | A | 2/1997 | Page et al. |
| 5,637,451 | A | 6/1997 | Ben-Hur et al. |
| 5,658,722 | A | 8/1997 | Margolis-Nunno et al. |
| 5,660,731 | A | 8/1997 | Piechocki et al. |
| 5,691,132 | A | 11/1997 | Wollowitz et al. |
| 5,753,258 | A | 5/1998 | Schreier et al. |
| 6,093,725 | A | 7/2000 | Cook et al. |
| 6,136,586 | A | 10/2000 | Budowsky |
| 6,143,490 | A | 11/2000 | Cook et al. |
| 6,150,109 | A | 11/2000 | Edson et al. |
| 6,171,777 | B1 | 1/2001 | Cook et al. |
| 6,177,441 | B1 | 1/2001 | Cook et al. |
| 6,270,952 | B1 | 8/2001 | Cook et al. |
| 6,410,219 | B1 | 6/2002 | Cook et al. |
| 6,514,987 | B1 | 2/2003 | Cook et al. |
| 6,544,727 | B1 | 4/2003 | Hei |
| 6,617,157 | B1 | 9/2003 | Budowsky et al. |
| 6,709,810 | B2 | 3/2004 | Cook et al. |
| 6,951,713 | B2 | 10/2005 | Hei et al. |
| 7,293,985 | B2 | 11/2007 | Cook et al. |
| 2001/0009756 | A1 | 7/2001 | Hei et al. |
| 2002/0182581 | A1 | 12/2002 | Cook et al. |
| 2002/0192632 | A1 | 12/2002 | Hei et al. |
| 2003/0113704 | A1 | 6/2003 | Stassinopoulos et al. |
| 2004/0029897 | A1 | 2/2004 | Cook et al. |
| 2004/0180321 | A1 | 9/2004 | Cook et al. |
| 2004/0185544 | A9 | 9/2004 | Hei |

FOREIGN PATENT DOCUMENTS

| | | |
|---|---|---|
| EP | 0 352 076 A2 | 1/1990 |
| EP | 0 352 076 B1 | 1/1990 |
| EP | 0 457 196 A2 | 11/1991 |
| EP | 0 641 796 A1 | 3/1995 |
| WO | WO 95/00631 A1 | 1/1995 |
| WO | WO 96/02838 A1 | 2/1996 |
| WO | WO 96/09846 A1 | 4/1996 |
| WO | WO 96/14737 A1 | 5/1996 |
| WO | WO 96/39816 A1 | 12/1996 |
| WO | WO 96/39818 A1 | 12/1996 |
| WO | WO 96/40857 A1 | 12/1996 |
| WO | WO 97/02028 A1 | 1/1997 |
| WO | WO 97/07674 A1 | 3/1997 |
| WO | WO 97/16966 A1 | 5/1997 |
| WO | WO 97/18844 A1 | 5/1997 |
| WO | WO 98/30545 A1 | 7/1998 |
| WO | WO 99/34839 A1 | 7/1999 |
| WO | WO 2006/050328 A1 | 5/2006 |

OTHER PUBLICATIONS

Aejmelaeus, R. et al. (1996). "Is There an Unidentified Defense Mechanism Against Infection in Human Plasma," *FEBS Letters* 384:128-130.

Al-Harbi, M.M. et al. (1997). "Gentamycin and Cyclosporine Increase Total Soluble Thiols in the Plasma and Lymphocytes of Rats and Perturb Erythrocyte Fragility," *Med. Sci. Res.* 25:155-157.

Awasthi, Y.C. et al. (Dec. 28, 1984). "Purification and Characterization of a New Form of Glutathione S-Transferase from Human Erythrocytes," *Biochemical and Biophys. Res. Commun.* 125:1053-1060.

Anonymous. (1971). Special Regents for Thiol Groups, *Aldrichimica Acta* 4(3):33-35.

(Continued)

*Primary Examiner*—Sandra E Saucier
(74) *Attorney, Agent, or Firm*—Morrison & Foerster LLP

(57) ABSTRACT

Methods are provided for improved quenching of undesired side reactions upon treating a red blood cell composition with a pathogen inactivating compound comprising a nucleic acid binding ligand and a functional group which is, or which is capable of forming, an electrophilic group. In some embodiments, the improved methods use a suitably high concentration of quencher that comprises a nucleophilic functional group that is capable of covalently reacting with the electrophilic group, wherein the treatment occurs within a desired pH range to provide sufficient quenching. Preferred quenchers for use in some of the methods include thiols, such as glutathione, which have been suitably neutralized such that addition to a red blood cell composition results in the desired concentration of quencher at a desirable pH range of 6.8 to 8.5.

20 Claims, 6 Drawing Sheets

OTHER PUBLICATIONS

Figure 1:
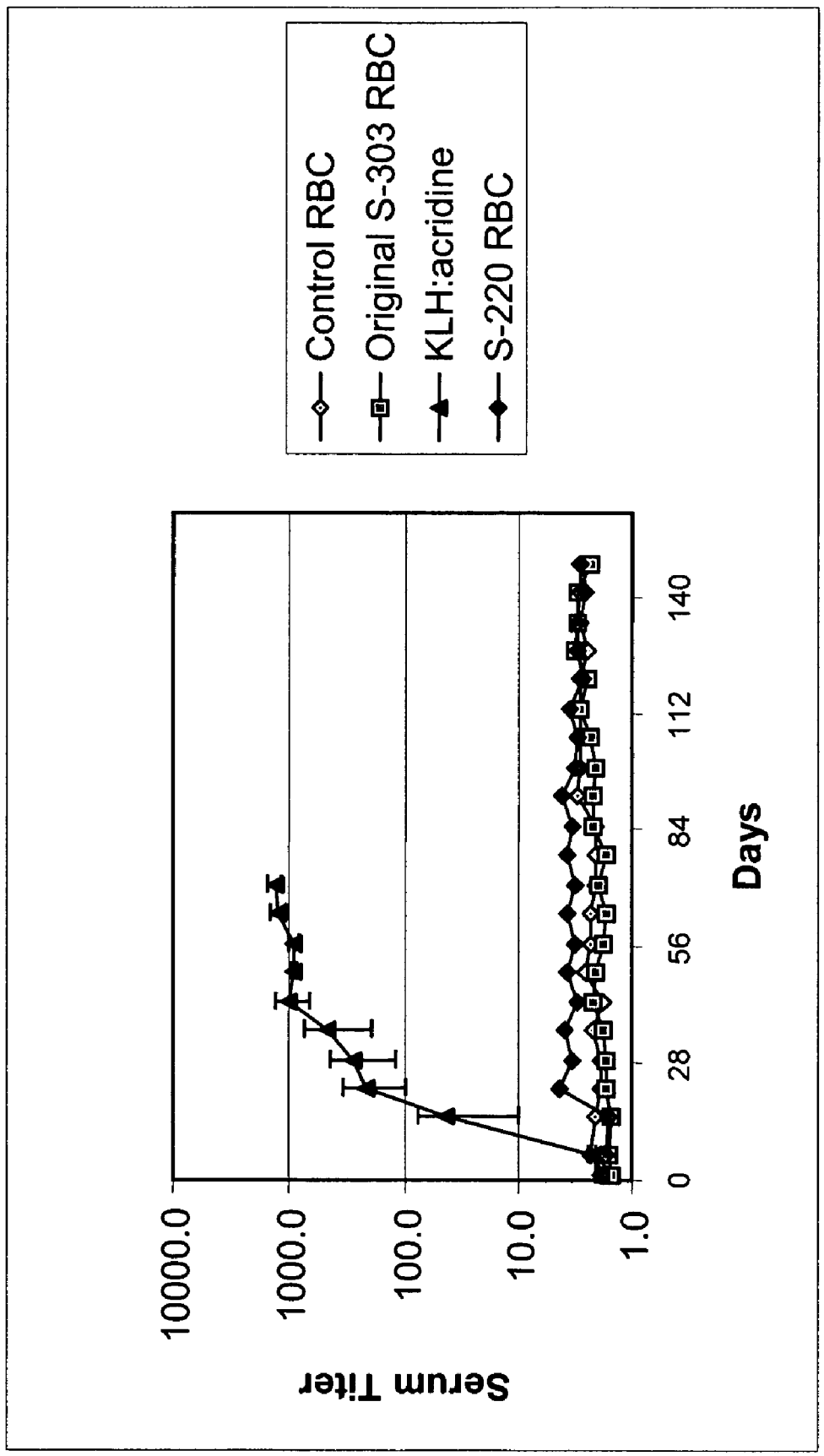

Anonymous. (1971). Special Regents for Thiol Groups, *Aldrichimica Acta* 4(3):46-48.

Anonymous. (2003). "Helinx® Technology Inactivates Human T-Cell Leukemia Virus (HTLV I/II) in Human Red Blood Cells," Abstract *presented at: American Association of Blood Banks (AABB)*, 56th Annual Meeting, Nov. 1-4, 2003, located at <http://www.cerus.com/index.cfm/abstracts/2003/Helinx174TechnologylnactivatesHumanTCell LeukemiaVirus H . . . >, last visited on Jan. 8, 2007, two pages.

Anonymous. (2003). "Helinx® Technology Inactivates Pathogens of Emerging Importance in Red Blood Cell Concentrates," Abstract *presented at: American Society of Hematology (ASH).* 45th Annual Meeting, Dec. 6-9, 2003, located at <http://www.cerus.com/index.cfm/abstracts/2003/Helinx174Technology InactivatesPathogensof EmergingImpor . . . >, last visited on Jan. 8, 2007, two pages.

Anonymous. (2003). "Treatment with Helina Technology Does Not Affect the Ability of Red Blood Cells to Overcome Oxidative Stress," Abstract *presented at: American Association of Blood Banks (AABB)*, 56th Annual Meeting, Nov. 1-4, 2003, located at <http://www.cerus.com/index.cfm/abstracts/2003/Treatment withHelinx174TechnologyDoesNotAffecttheAbilit . . . >, last visited on Jan. 8, 2007, two pages.

Anonymous. (2004). "Antibody Formulation to S-303-Treated RBCs in Setting of Chronic RBC Transfusion," Abstract *presented at:Ametican Society of Hematology (ASH)*, 46th Annual Meeting, Dec. 4-7, 2004, located at <http://www.cerus.com/index.cfm/abstracts/2004/AntibodyFormulationtoS303TreatedRBCsin SettingofChronic . . . >, last visited on Jan. 8, 2007, two pages.

Anonymous. (2004). "Elimination of Immunoreactivity of Red Cells Treated with a Modified S-303 Pathogen Inactivation Process," Abstract *presented at: American Society of Hematology (ASH)*, 46th Annual Meeting, Dec. 4-7, 2004, located at <http://www.cerus.com/index.cfm/abstracts/2004/EliminationofImmunoreactivityofRedCellsTreatedwithaMod . . . >, last visited on Jan. 8, 2007, two pages.

Anonymous. (2004). "Transfusion of S-303 Treated RBCs to Treat Acute Anemia During or Following Cardiac Surgery: Results of a Phase III Trial," Abstract *presented at:American Society of Hematology (ASH)*, 46th Annual Meeting, Dec. 4-7, 2004, located at <http://www.cerus.com/index.cfm/abstracts/2004/Transfusionof S303TreatedRBCsToTreatAcuteAnemiaduringor . . . >, last visited on Jan. 8, 2007, two pages.

Anonymous. (Dec. 3, 2004). "Cerus Corporation and Collaborators to Present at American Society of Hematology Meeting," *Press Release, Cerus Corporation*, located at <http://www.cerus.com/index.cfm/News/Press_ Release_ Archive?Year=2007&NID=8..>, last visited on Jan. 8, 2007, four pages.

Baxt, B. et al. (1976). "Mechanisms of Vesicular Stomatitis Virus-Induced Cytopathic Effects," *Virology* 72:383-392.

Begleiter, A. et al. (1996). "Chlorambucil in Chronic Lymphocytic Leukemia: Mechanism of Action," *Leukemia and Lymphoma* 23:187-201.

Beutler, E. et al. (Jun. 1982)."The Osmotic Fragility of Erythrocytes After Prolonged Liquid Storage and After Reinfusion," *Blood* vol. 59(6):1141-1147.

Bolton, M.G. et al. (May 1991). "Specificity of Isozymes of Murine Hepatic Gluthathione S-Transferase for the Conjugation of Glutathione with L-Phenylalanine Mustard," *Cancer Research* 51:2410-2415.

Bolton, M.G. et al. (1993). "Kinetic Analysis of the Reaction of Melphalan with Water, Phosphate, and Glutathione," *Drug Metab. Dispos.* 21:986-996.

Bonadonna, G. et al. (1964). "Protection Studies with Sodium Thiosulfate Against Methyl bis(3-Chloroethyl)amine Hydrochloride (HN2) and its Ethylenimonium Derivative," *Clin. Pharm. & Thera* 6(1):50-64.

Budowsky, E.I. et al. (1996). "Principles of Selective Inactivation of the Viral Genome: Dependence of the Rate of Viral RNA Modification on the Number of Protonizable Groups in Ethyleneimine Oligomers, "*Vaccine Res.* 5(1):29-39.

Chong, Y. et al. (1990). "Evaluation of Thiol Borth for the Culture of *Salmonella typhi* and Other Bacteria from Blood," *Yonsei Medical Journal* 31(2):163-167.

Colvin, M. et al. (Mar. 1976). "Alkylating Properties of Phosphoramide Mustard," *CancerRes.* 36:1121-1126..

Colvin, O. M. et al. (1993). "Role of Glutathione in Cellular Resistance to Alkylating Agents," *Adv. Enzyme Regul.* 33:19-26.

Davey, R.J. et al. (1992)."The Effect of Prestorage Irradiation on Posttransfusion Red Cell Survival," *Transfusion* 32(6):525-528.

Dern, R.J. et al. (1967). "Studies on the Preservation of Human Blood. II. The Relationship of Erythrocyte Adenosine Triphosphate Levels and other In Vitro Measures to Red Cell Storageability," *J. Lab. & Clin. Med.* 69:968-978.

Dirr, H. et al. (1994). "X-Ray Crystal Structures of Cytosolic Glutathione S-Transferases: Implications for Protein Architecture, Substrate Recognition and Catalytic Function," *Eur. J. Biochem* 220:645-661.

Dirven, H.A.A.M. et al. (Mar. 1996). "Glutathione Conjugation of Alkylating Cytostatic Drugs with a Nitrogen Mustard Group and the Role of Glutathione *S*-Transferases," *Chem. Res. Toxicol.* 9(2):351-360.

Dirven, H.A.A.M. et al. (1995). "Glutathione Conjugation of the Cytosatic Drug Ifosfamide and the Role of Human Glutathione S-Tramsferases." *Chem. Res. Toxicol.* 8(7):979-986.

Dirven, H.A.A.M. et al. (1994). "The Interaction of Glutathione with 4-Hydroxycyclophosphamide and Phosphoramide Mustard, Studied by $^{31}$P Nuclear Magnetic Resonance Spectroscopy," *Chem. Bio. Interact.* 93:185-196.

Dirven, H.A.A.M. et al. (Apr. 15, 1995). "The Role of Human Glutathione S-Tranferases Isoenzymes in the Formation of Glutathione Conjugates of the Alkylating Cytostatic Drug Thiotepa," *Cancer Res.* 55:1701-1706.

Dorr, R.T. (Feb. 1991). "Chemoprotectants for Cancer Chemotherapy," *Semin. Oncol.* 18(1-Suppl.2):48-58.

Dulik, D.M. et al. (1990). "Characterization of Glutathione Conjugates of Chlorambucil by Fast Atom Bombardment and Thermospray Liquid Chromatography/Mass Spectrometry," *Biomed Environ Mass Spectrom* 19:248-252.

Dulik, D.M. et al. (Oct. 1986). "Characterization of Melphalan-Glutathione Adducts Whose Formation is Catalyzed by Glutathione Transferases," *Biochem Pharmacol.* 35(19):3405-3409.

Dulik, D.M. et al. (1987). "Conversion of Melphalan to 4-(Glutathionyl)Phenylalanine. A Novel Mechanism for Conjugation by Glutathione-S-tranferases," *Drug Metab. Dispos.* 15(2):195-199.

Fasth, A. et al. (1973). "Protective Effect of Thiosulfate and Metabolic Thiosulfate Precursors Against Toxicity of Nitrogen Mustard ($HN_2$)," *Biochem Pharmacology* 22:1337-1351.

Gamcsik, M.P. et al. (1997). "Kinetics of the Conjugation of Aniline Mustards with Glutathione and Thiosulfate," *Chem. Biol. Interact.* 105:35-52.

Gao, X. et al. (1991). "A Novel Cationic Liposome Reagent for Efficient Transfection of Mammalian Cells," *Biochem. Biophys. Res. Commun.* 179(1):280-285.

Gao, X. et al. (1993). "Cytoplasmic Expression of a Reporter Gene by Co-Delivery of T7 RNA Polymerase and T7 Promoter Sequence with Cationic Liposomes," *Nucleic Acids Res.* 21(12):2867-2872.

Gao, X. et al. (1996). "Potentiation of Cationic Liposome-Mediated Gene Delivery by Polycations," *Biochemistry* 35(3):1027-1036.

Gourdie, T.A. (1991). "Synthesis and Evaluation of DNA-Targeted Spatially Separated Bis(aniline mustards) as Potential Alkylating Agents with Enhanced DNA Cross-Linking Capability," *J. Med. Chem.* 34(1):240-248.

Greenwalt, T.J. et al. (1990). "Studies in Red Blood Cell Preservation: 3. A Phosphate-Ammonium-Adenine Addictive Solution," *Vox Sang* 58:94-99.

Guenther, T.M. et al. (1992). "Direct Measurement of Melphalan Conjugation with Glutathione: Studies with Human Melanoma Cells and Mammalian Liver," *J. Pharmacol. Exp. Ther.*260(3):1331-1336.

Guillemain, B. et al. (2003). "Helinx® Technology Inactivates Human T-Cell Leukemia Virus (HTLV-I/II) in Human Red Blood Cells," Abstract *presented at the 56th Annual Meeting of the American Association of Blood Banks (AABB)*, San Diego, CA, Nov. 1-5, 2003, two pages.

Hageman, G.J. et al. (1997). "Reducing Effects of Garlic Constituents on DNA Adduct Formation in Human Lymphocytes In Vitro," *Nutrition and Cancer* 27(2):177-185.

Hanson, C.V. et al. (Sep. 1990). "Application of a Rapid Microplaque Assay for Determination of Human Immunodeficiency Virus Neutralizing Antibody Titers," *J. Clin. Microbio.* 28(9):2030-2034.

Högman, C.F. et al. (1991). "Storage of Saline-Adenine-Glucose-Mannitol-Suspended Red Blood Cells in a new Plastic Container: Polyvinylchloride Plasticized with Butyryl-n-Trihexyl-Citrate," *Transfusion* 31(1):26-29.

Högman C.F. et al. (1993). "Half-Strength Citrate CPD Combined with A New Additive Solution for Improved Storage of Red Blood Cells Suitable for Clinical Use," *Vox Sang* 65:271-278.

Hsiung, G.D. et al. (1957). "Morphologic Characteristics of Plaques Produced on Monkey Kidney Monolayer Cultures by Enteric Viruses (Poliomyelitis, Coxsackie, and Echo Groups)," *The Journal of Immunology* 78:128-136.

International Search Report mailed Apr. 5, 2006, for PCT Application No. PCT/US2005/039392 filed Oct. 31, 2005, five pages.

Kawabata, T.T. et al. (1990). "Mechanisms of in vitro Immunosuppression by Hepatocyte-Generated Cyclophosphamide Metabolites and 4-Hydroperoxycyclophosphamide," *Biochem. Pharmacol.* 40(5):927-935.

Koch, T. et al. (1996). "Effects of *N*-Acetylcysteine on Bacterial Clearance," *European J. Of Clinic Invest.* 26:884-892.

Lasic D.D. (1997). "Liposomes," Chapter 6 in *Liposomes in Gene Delivery*, CRC Press, Boca Ration, FL, pp. 67-112.

LoGrippo, G.A. et al. (1958). "Chemical and Combined Methods for Plasma Sterilization" in *Proceedings of the Sixth Congress of the International Society of Blood Transfusions*, S. Karger: New York, NY, pp. 225-230.

Malmberg, P.O. et al. (1979). "Effect of Increased Blood-Oxygen Affinity on Oxygen Transport in Hemorrhagic Shock," *J. Appl Physiol. Respirat. Environ Exercise Physiol* 47:889-895.

Mangels, J.I. et al. (1978). "Quantitative Evaluation of Three Commercial Blood Culture Media for Growth of Anaerobic Organisms," *J. of Clin Microbiology* 7(1):59-62.

Marcus, P.I. et al. (1994). "Cell Killing by Viruses: 1. Comparison of Cell-Killing, Plaque-Forming, and Defective-Interfering Particles of Vesicular Stomatitis Virus," *Virology* 57:321-338.

Mattes, W.B. (1992). "Use of [8-$^3$H]Guanine-Labeled Deoxyribonucleic Acid to Study Alkylating Agent Reaction Kinetics and Stability," *Anal. Biochem.* 206(1):161-167.

Mulder, G.J. et al. (1997). "Modulation of Glutathione Conjugation in Vivo: How to Decrease Glutathione Conjugation in Vivo or in Intact Cellular Systems in Vitro," *Chemico-Biological Interactions* 105:17-34.

Mullan, R.J. et al. (Jun. 23, 1989). "Guidelines for Prevention of Transmission of Human Immunodeficiency Virus and Hepatitis B Virus to Health-Care and Public Safety Workers," Morbidity and Mortality Weekly Report, 38(S-6):1, 3-37.

Ness, P.M. et al. (Oct. 2001). "An Animal Model for Delayed Hemolytic Transfusion Reactions,"*Trans. Med. Rev.* 15(4):305-317.

Petz, L.D. et al., eds. (1996). "K Irradiation of Cellular Blood Components for Prevention of TA-GVHD," in "Graft-Versus-Host-Disease" in *Clinical Practice of Transfusion Medicine*, Third Edition, Churchill Livingstone, pp. 939-940.

Popovic, M. et al. (May 4, 1984). "Detection, Isolation, and Continuous Production of Cytophatic Retroviruses (HTLV-III) from Patients with AIDS and Pre-AIDS," *Science* 224:497- 500.

Press Release (Sep. 4, 2003)."Baxter And Cerus Halt Red Blood Cell Clinical Trials for Investigational Pathogen Inactivation System," Cerus Corporation, two pages.

Press Release (Nov. 17, 2003). "Vitex Halts Enrollment in Phase III Chronic Trial of the INACTINE™ Pathogen Reduction System," V.I. Technologies, Inc., two pages.

Roth, Jr., E.F. et al. (1987). "Survival Rates and Properties of Sickel Cell Anemia Red Cells Treated with Nitrogen Mustard," *Pathophysiological Aspects of Sickle Cell Vaso-Occlusion* pp. 245-261.

Rywkin, S. et al. (1992). "Importance of Type I and Type II Mechanisms in the Photodynamic Inactivation of Viruses in Blood with Aluminum Phthalocyanine Derivatives," *Photochemistry and Photobiology* 56(4):463-469.

Schott, M.A. et al. (2005). "Modification of the S-303 RBC Pathogen Inactivation Process Results in Normal S-303 RBC Viability in Rabbits Hyper-immunized to S-303," *presented at the: International Society of Blood Transfusion (ISBT)*, XV Regional Congress, Europe, Athens, Greece, Jul. 2-6, 2005, two pages.

Schott, M.A. et al. (2005). "Retention of RBC Viability After Pathogen Inactivation with S-303: Use of a Hyperimmune (Anti-S-303) Rabbit Transfusion Model," *presented at the 10th Congress of the European Hematology Association (EHA)*, Stockholm, Sweden, Jun. 2-5, 2005, two pages.

Simon, E.R. (Jul.-Aug. 1977). "Adenine in Blood Banking," *Transfusion* 17(4):317-325.

Song, P.-S. et al. (Jun. 1979). "Review Article: Photochemistry and Photobiology of Psoralens," *Photochem. and Photobio.* 29:1177-1197.

Stassinopoulos, A. et al. (2004). "Elimination of Immunoreactivity of Red Cells Treated with a Modified S-303 Pathogen Inactivation Process," Abstract *presented at the 46th Annual Meeting of the American Society of Hematology (Ash)*, San Diego, CA, Dec. 4-7, 2004, two pages.

Stassinopoulos, A. et al. (2005) "A Modified S-303 pathogen Inactivation Process Eliminates Immunoreactivity of S-303 RBC Detected in Pivotal Clinical Trials" Abstract No. 0774 *presented at:European Hematology Association (EHA)*, 10th Congress, Concord, United States of America, Jun. 5, 2005, located at <http://www.parthenimpact.com/cgi-bin/pco/6_05EHA/public/index. cgi?unit=pub_search_r...> last visited on Jan. 8, 2007, two pages.

Stassinpoulos, A. et al., (2005). "Retention of RBC Viability After pathogen Inactivation with S-303: Use of a hyperimmune (Anti-S-303) rabbit transfusion model," Abstract No. 0614 *presented at:European Hematology Assocation (EHA)*,10th Congress, Stockholm, Sweden, Jun. 2-5, 2005, located at <http://www.parthenimpact.com/cgi-bin/pco/6_05EHA/public/index. cgi?unit=pub_search_r...>, last visited on Jan. 8, 2007, two pages.

Suzuki, T. et al. (Sep. 1987)."Biotinylated erythrocytes: In Vivo Survival and In Vitro Recovery," *Blood* 70(3):791-795.

Szinicz, L. et al. (1981). "Effect of Various Compounds on the Reaction of tris-(2-Chloroethyl)amine with Ribonucleic Acid in Vitro and on its Toxicity in Mice," *Arzneimittel-Forshung* 31:1713-1717.

Tew, K.D. (Aug. 15, 1994). "Glutathione-Associated Enzymes in Anticancer Drug Resistance," *Cancer Research* 54:4313-4320.

Wagner, Jr., S.J. et al. (1993). "Red Cell Alterations Associated with Virucidal Methylene Blue Phototreatment," *Transfusion* 33(1):30-36.

Watson, E. et al. (Dec. 1985). "Kinetics of Phosphoramide Mustard Hydrolysis in Aqueous Solution," *J. Pharm. Sci.* 74(12):1283-1292.

Wedner, H.J. et al. (1985). "Inhibition of Lectin-Induced Lymphocyte Activation by 2-cyclohexene-1-One: Analysis of DNA Synthesis in Individual Cells by BUdR Quenching of Hoechst 33258," (1985). *Int. J. lmmunopharmac.* 7(1):25-30.

Weinberg, E. et al. (Feb. 1984). "Effectiveness of the Antimicrobial Removal Device, BACTEC 16B Medium, and Thiol Broth in Neutralizing Antibacterial Activities of Imipenem, Norfloxacin, and Related Agents," *J. of Clin. Microbiology* 19(2):207-209.

Woodson, R.D. (1979). "Physiological Significance of Oxygen Dissociation Curve Shifts," *Critical Care Medicine* 7(9):368-373.

Written Opinion mailed Apr. 5, 2006, for PCT Application No. PCT/US2005/039392 filed Oct. 31, 2005, five pages.

Yuan Z. et al. (1991). "Glutathione Conjugation with Phosphoramide Mustard and Cyclophosphamide. A Mechanistic Study Using Tandem Mass Spectometry," *Drug Metab. Dispos.* 19(3):625-629.

Castro, G.M. at al. (2005). "A Modified S-303 Pathogen Inactivation Process Eliminates lmmunoreactivity of S-303 RBC Detected in Pivotal Clinical Trials," *presented at the: European Hematology Association(ASH)*, 10th Congress, Stockholm, Sweden, Jun. 2-5, 2005, sixteen pages.

US 6,331,387, 12/2001, Hei (withdrawn)

QUENCHING METHODS FOR RED BLOOD CELL INACTIVATION PROCESS

CROSS REFERENCE TO RELATED APPLICATIONS

This application claims the priority benefit of U.S. Provisional Application Ser. No. 60/623,177, filed Oct. 29, 2004, which is hereby incorporated by reference herein in its entirety.

FIELD OF THE INVENTION

The field of this invention relates to methods of quenching reactive electrophilic compounds used in treating blood products to inactivate possible pathogen contaminants. In particular, nucleophilic compounds, such as thiols, are used to quench the reactive electrophilic compounds in red blood cell compositions.

BACKGROUND OF THE INVENTION

The transmission of disease by blood products and other biological materials remains a serious health problem. While significant advances in blood donor screening and blood testing have occurred, viruses such as hepatitis B (HBV), hepatitis C (HCV), and human immunodeficiency virus (HIV) may escape detection in blood products during testing due to low levels of virus or viral antibodies. In addition to the viral hazard, there are currently no adequate, licensed tests to screen for the presence of non-viral microbes, such as bacteria or protozoans, in blood intended for use in transfusions. The risk also exists that a hitherto unknown pathogen may become prevalent in the blood supply and present a threat of disease transmission, as in fact occurred before the recognition of the risk of HIV transmission via blood transfusions.

Chemical agents have been introduced into blood or blood plasma to inactivate pathogens prior to clinical use of the blood product. Typically, for blood products having little or no red blood cell content, such as platelets and plasma, photochemically activated compounds such as psoralens are used. For red blood cell containing blood products, compounds have been developed for pathogen inactivation, which do not require photoactivation. These compounds typically have electrophilic groups that react with pathogens, more specifically with pathogen nucleic acid. For example, U.S. Pat. No. 5,055,485 describes the inactivation of viruses in cell and protein containing compositions using aryl diol epoxides. Other compounds that generate electrophiles in situ may be used. LoGrippo et al. evaluated the use of nitrogen mustard, $CH_3$—$N(CH_2CH_2Cl)_2$, for viral inactivation. LoGrippo et al., Proceedings of the Sixth Congress of the International Society of Blood Transfusion, Bibliotheca Haematologica (Hollander, ed.), 1958, pp. 225-230. More significantly, U.S. Pat. Nos. 6,410,219 and 5,691,132, the disclosures of which are hereby incorporated by reference, describe the use of compounds that have a nucleic acid targeting component as well as an electrophilic component that reacts with the nucleic acid in order to inactivate the pathogen. U.S. Pat. No. 6,514,987, the disclosure of which is hereby incorporated by reference, describes similar compounds, wherein the nucleic acid targeting component of the compound is linked to the reactive electrophilic component via a hydrolysable linker. U.S. Pat. Nos. 6,136,586 and 6,617,157, the disclosures of which are hereby incorporated by reference, describe using ethyleneimine oligomers and related compounds for pathogen inactivation. These ethyleneimine derived compounds typically have an aziridine group, which provides the reactive electrophilic component, and a polyamine component, which provides nucleic acid targeting of the compound. The general class of nucleic acid targeted compounds having an electrophilic or similar group reactive with the nucleic acid are used to inactivate pathogens in blood, blood products, and a variety of samples of biological origin.

There is some concern that, while these compounds are designed to react specifically with nucleic acids, they may still react with other components of the blood, such as proteins or cellular membranes. These side reactions are unfavorable, and may cause adverse effects, such as modifications of the proteins and cell membranes that may be recognized by the immune system. When such treated blood products are used repeatedly, they may result in an immune response of the recipient to the treated blood product. U.S. Pat. No. 6,709,810, the disclosure of which is hereby incorporated by reference, describes methods of quenching such pathogen inactivating compounds in order to reduce the level of any such adverse side reactions. However, while such methods significantly reduce unwanted side reactions, a further reduction of unwanted immune responses is desirable. Recent clinical trials using such compounds for the treatment of red blood cells have indicated the possibility of such adverse events. In a V.I. Technologies, Inc. press release dated Nov. 17, 2003, it was recommended that their Phase III chronic trial of the INACTINE™ Pathogen Reduction System for red blood cells be halted due to a concern with antibody responses to INACTINE™ treated red blood cells. In a Cerus Corporation press release dated Sep. 4, 2003, it was indicated they voluntarily halted a Phase III trial for their pathogen inactivated red blood cell program after two study patients developed antibodies to red blood cells treated with S-303, the compound used in their pathogen inactivation system for red blood cells. Such antibodies are typically detected with the use of an Indirect Antiglobulin Test that can be performed without a detailed knowledge of the nature or homogeneity of the actual antibody. Such assays are well known to those skilled to the art and are very sensitive, allowing the detection of as low as 500 molecules per RBC. The most common method of detecting these antibodies is through the mixing of patient sera with the RBC preparation that is a candidate for infusion and detecting whether an agglutination reaction occurs. This is called a cross match of the RBC unit to the patient serum. More sensitivity is provided by the inclusion of an anti-human immunoglobulin cross reacting with the antibody. This enhances the reactivity between IgGs or other antibodies on the surface of RBC. Finally, even more detection sensitivity can be obtained by the inclusion of potentiators in the reaction medium which enhance the on-rate of antibodies with one another (AABB manual $13^{th}$ edition). Such assays are more sensitive than, for example, flow cytometry assays and may be observed even when other methods indicate the absence of any potential antibody. Such phenomena occur in clinical trials and many times are associated with specific patient populations that may have a higher tendency to develop these antibodies.

Thus, there is a need for methods to further reduce unwanted electrophilic side reactions of pathogen inactivating compounds that react with pathogens via an electrophilic group, while preserving the ability of the pathogen inactivating compound to inactivate harmful pathogens. Specifically, there is a need for improved methods of quenching pathogen inactivating compounds in red blood cells. Such a new method is needed to significantly reduce the risk of an adverse immune response to the red blood cells due to the treatment with a pathogen inactivating compound.

BRIEF SUMMARY OF THE INVENTION

The present invention provides a variety of methods of treating red blood cell compositions with pathogen inactivating compounds under improved conditions for quenching an undesired side reaction of the pathogen inactivating compound with the red blood cells. In some embodiments, the quenching is improved by adjustment of the pH and/or increases in the concentration of the quencher.

In one aspect, the present invention provides a method of treating a red blood cell composition comprising a) providing i) a pathogen inactivating compound comprising a reactive electrophilic group, ii) a quencher comprising a thiol group, and iii) a composition comprising red blood cells, wherein there is a possibility that the red blood cell composition is contaminated with a pathogen, and b) mixing the pathogen inactivating compound and quencher with the composition comprising red blood cells, wherein the resulting mixture is in a pH range suitable to provide adequate quenching of binding of the pathogen inactivating compound to the red blood cells. In a further embodiment, the method includes step c) adjusting the pH of the composition comprising red blood cells. In some embodiments, the treatment results in the inactivation of at least 1 log, also at least 2 log, or at least 3 log of a pathogen contaminant. In some embodiments, the red blood cell composition contains leukocytes, and the treatment results in the inactivation of at least 1 log, also at least 2 log, or at least 3 log of the leukocytes. In some embodiments, the quencher is mixed with the composition comprising red blood cells prior to adding the pathogen inactivating compound. In some embodiments, the pH of the composition comprising red blood cells is adjusted prior to mixing with the pathogen inactivating compound and quencher. In some embodiments, the pH of the composition comprising red blood cells is adjusted after addition of the pathogen inactivating compound. In some embodiments, the pH of the composition comprising red blood cells is adjusted by the addition of the quencher. In some embodiments, the mixture of the quencher, pathogen inactivating compound and composition comprising red blood cells has a pH at room temperature in the range of about 6.8 to 8.5, also about 7.0 to 8.5, also about 7.2 to 8.5, or about 7.2 to 8.0 once all three components have been mixed. In some embodiments, the mixture of the quencher, pathogen inactivating compound and composition comprising red blood cells is incubated for a suitable time interval, such as for about 30 minutes to 48 hours, also about 2 to 24 hours, also about 8 to 24 hours. In a further embodiment, the incubation is in a temperature range of about 1° C. to 30° C., also about 18° C. to 25° C., or about room temperature. In some embodiments, the concentration of quencher once all three components have been mixed is in the range of about 2 mM to about 40 mM, also about 4 mM to about 40 mM, also about 4 mM to about 30 mM, also about 5 mM to about 30 mM, also about 10 mM to about 30 mM, also about 20 mM. In some embodiments, the concentration of the quencher in the resulting mixture is greater than about 2 mM, at least about 4 mM, at least about 5 mM, at least about 10 mM, or at least about 15 mM. In some embodiments, the molar ratio of quencher to pathogen inactivation compound once all three components have been mixed is about 10:1 to about 400:1, also about 10:1 to about 200:1, also about 20:1 to about 200:1, also about 50:1 to about 200:1, also about 100:1. In some embodiments, the quencher comprises cysteine or a derivative of cysteine. In some embodiments, the quencher is a peptide comprising at least one cysteine or a derivative of cysteine. In a preferred embodiment, the quencher is glutathione. In some embodiments, the quencher is neutralized and addition of the neutralized quencher effects the adjustment of pH of the red blood cell composition. In some embodiments, the neutralized quencher comprises cysteine or a derivative of cysteine. In some embodiments, the neutralized quencher is a peptide comprising cysteine or a derivative of cysteine. In some embodiments, the pathogen inactivating compound comprises a nucleic acid binding group. In some embodiments, the nucleic acid binding group is an intercalator, such as an acridine group. In some embodiments, the nucleic acid binding group is a polyamine. In some embodiments, the pathogen inactivating compound comprises a nucleic acid binding group linked to the reactive electrophilic group via a hydrolysable bond. In some embodiments, the nucleic acid binding group is an intercalator and the reactive electrophilic group is selected from the group consisting of a mustard, a mustard intermediate, and a mustard equivalent. In a preferred embodiment, the quencher is neutralized glutathione, wherein protonated glutathione is neutralized with about 2 equivalents of a suitable base, and the pathogen inactivating compound is β-alanine, N-(acridin-9-yl), 2-[bis(2-chloroethyl)amino]ethyl ester.

In an additional aspect, the invention provides a method for treating a red blood cell composition comprising, a) providing i) a pathogen inactivating compound comprising a nucleic acid binding group and a reactive electrophilic group, ii) a quencher comprising a cysteine or suitable cysteine derivative, and iii) a composition comprising red blood cells, wherein there is a possibility that the red blood cell composition is contaminated with a pathogen, b) mixing the quencher with the composition comprising red blood cells, wherein addition of the quencher effects the adjustment of the pH of the mixture to a suitable pH, and c) mixing the pathogen inactivating compound with the composition comprising red blood cells, wherein a pathogen, if present in the composition comprising red blood cells, is inactivated by at least 1 log, also at least 2 log, also at least 3 log. In some embodiments, the red blood cell composition contains leukocytes, and the treatment results in the inactivation of at least 1 log, also at least 2 log, or at least 3 log of the leukocytes. In some embodiments, the quencher is mixed with the composition comprising red blood cells prior to mixing with the pathogen inactivating compound. In some embodiments, the quencher is mixed with the composition comprising red blood cells subsequently to mixing with the pathogen inactivating compound. In some embodiments, the quencher and pathogen inactivating compound are mixed with the composition comprising red blood cells simultaneously, or essentially simultaneously, such as within about 1 minute of each other. In some embodiments, the mixture of the quencher and composition comprising red blood cells is incubated for about 1 to 30 minutes prior to mixing with the pathogen inactivating compound. In some embodiments, this incubation is at a temperature in the range of about 1° C. to 30° C., also about 18° C. to 25° C., or about room temperature. In some embodiments, the mixture of the quencher, pathogen inactivating compound and composition comprising red blood cells is incubated for a suitable time interval, such as for about 30 minutes to 48 hours, also about 2 to 24 hours, also about 8 to 24 hours. In a further embodiment, the incubation is in a temperature range of about 1° C. to 30° C., also about 18° C. to 25° C., or about room temperature. In some embodiments, a suitable pH upon mixing the quencher with the composition comprising red blood cells is in the range of about 6.8 to 8.5, also about 7.0 to 8.5, also about 7.2 to 8.5, or about 7.2 to 8.0, as measured at room temperature. In some embodiments, once all three components have been mixed, the pH of the mixture is in the range of about 6.8 to 8.5, also about 7.0 to 8.5, also about 7.2 to 8.5, or about 7.2 to 8.0, as measured at room temperature. In some embodiments, the concentration of quencher once all three components have been mixed is in the range of about 2 mM to about 40 mM, also about 4 mM to about 40 mM, also about 4 mM to about 30 mM, also about 5 mM to about 30 mM, also about 10 mM to about 30 mM, also about 20 mM. In some embodiments, the molar ratio of quencher to pathogen inactivation compound once all three components have been mixed is about 10:1 to about 400:1, also about 10:1 to about 200:1, also about 20:1 to about 200:1, also about 50:1 to about 200:1, also about 100:1. In some embodiments, the quencher is a peptide comprising at least one cysteine or a derivative of cysteine. In a preferred embodiment, the quencher is glutathione. In some embodiments, the quencher is neutralized or is in a form that effects the desired adjustment in pH of the composition. In some embodiments, the quencher is neutralized by addition of 1 equivalent, also about 2 equivalents of base to the quencher. In some embodiments, the quencher is in a neutralized form, such as a suitable salt. In some embodiments, the quencher is neutralized. In some embodiments, the neutralized quencher is a neutralized peptide comprising cysteine or a derivative of cysteine. In a preferred embodiment, the neutralized peptide is neutralized glutathione. In some embodiments, the nucleic acid binding group of the pathogen inactivating compound is an intercalator, such as an acridine group. In some embodiments, the nucleic acid binding group is a polyamine. In some embodiments, the nucleic acid binding group is linked to the reactive electrophilic group via a hydrolysable bond. In some embodiments, the nucleic acid binding group is an intercalator and the reactive electrophilic group is selected from the group consisting of a mustard, a mustard intermediate, and a mustard equivalent. In some embodiments, the nucleic acid binding group is a polyamine and the electrophilic group is an aziridine group or an aziridinium group. In a preferred embodiment, the quencher is neutralized glutathione and the pathogen inactivating compound is β-alanine, N-(acridin-9-yl), 2-[bis(2-chloroethyl)amino]ethyl ester.

In another aspect, the invention provides a method for treating a red blood cell composition comprising, in the following order, a) providing i) β-alanine, N-(acridin-9-yl), 2-[bis(2-chloroethyl)amino]ethyl ester, ii) neutralized glutathione, and iii) a composition comprising red blood cells, wherein there is a possibility that the red blood cell composition is contaminated with a pathogen, b) mixing the neutralized glutathione with the composition comprising red blood cells, c) incubating the mixture for an appropriate time interval, and d) mixing the β-alanine, N-(acridin-9-yl), 2-[bis(2-chloroethyl)amino]ethyl ester with the mixture of neutralized glutathione and the composition comprising red blood cells, wherein a pathogen, if present in the composition comprising red blood cells, is inactivated by at least 1 log, also at least 2 log, also at least 3 log. In some embodiments, the red blood cell composition contains leukocytes, and the treatment results in the inactivation of at least 1 log, also at least 2 log, or at least 3 log of the leukocytes. In some embodiments, the neutralized glutathione is provided as a suitable salt. In some embodiments, the neutralized glutathione is provided by neutralizing protonated glutathione with about 1 equivalent of base, also about 2 equivalents of base. In some embodiments, the neutralized glutathione is in solution. In some embodiments, the neutralized glutathione is a solid, such as a lyophilized powder are a suitable salt. In some embodiments, the time interval for incubating the red blood cells mixed with glutathione is about 1 to 30 minutes, also about 5 to 20 minutes, wherein the incubation is at a temperature in the range of about 1° C. to 30° C., also about 18° C. to 25° C., or about room temperature. In some embodiments, after mixing with the β-alanine, N-(acridin-9-yl), 2-[bis(2-chloroethyl)amino]ethyl ester, the mixture is incubated for a suitable time interval, such as for about 30 minutes to 48 hours, also about 2 to 24 hours, also about 8 to 24 hours. In a further embodiment, the incubation is in a temperature range of about 1° C. to 30° C., also about 18° C. to 25° C., or about room temperature. In some embodiments, upon mixing of the β-alanine, N-(acridin-9-yl), 2-[bis(2-chloroethyl)amino]ethyl ester, the concentration of glutathione in the mixture is in the range of about 5 mM to about 30 mM and the concentration of β-alanine, N-(acridin-9-yl), 2-[bis(2-chloroethyl)amino]ethyl ester is in the range of about 0.05 mM to about 0.5 mM. In some embodiments, upon mixing of the β-alanine, N-(acridin-9-yl), 2-[bis(2-chloroethyl)amino]ethyl ester, the concentration of glutathione in the mixture is in the range of about 10 mM to about 30 mM and the concentration of β-alanine, N-(acridin-9-yl), 2-[bis(2-chloroethyl)amino]ethyl ester is in the range of about 0.05 mM to about 0.3 mM. In some embodiments, upon mixing of the β-alanine, N-(acridin-9-yl), 2-[bis(2-chloroethyl)amino]ethyl ester, the concentration of glutathione in the mixture is about 20 mM and the concentration of β-alanine, N-(acridin-9-yl), 2-[bis(2-chloroethyl)amino]ethyl ester is about 0.2 mM.

In another aspect, the invention provides a method of treating a red blood cell composition comprising: (a) providing i) a pathogen inactivating compound comprising a functional group which is, or which forms, a reactive electrophilic group, ii) a quencher comprising a thiol group, wherein the thiol is capable of reacting with the reactive electrophilic group of the pathogen-inactivating compound, and iii) a composition comprising red blood cells, wherein there is a possibility that the red blood cell composition is contaminated with a pathogen; and (b) mixing the pathogen inactivating compound and quencher with the composition comprising red blood cells, wherein the concentration of the quencher in the resulting mixture is greater than 2 mM, wherein the pH of the resulting mixture at room temperature is in the range of about 6.7 or higher. In some embodiments, the pH of the resulting mixture at room temperature is in the range of about 7.0 to 8.5.

In another aspect, the invention provides a method of treating a red blood cell composition, comprising mixing the following with the red blood cell composition: (a) a pathogen-inactivating compound, wherein the pathogen-inactivating compound comprises a nucleic acid binding ligand and a functional group which is, or which forms, an electrophilic group capable of reacting with nucleic acids; (b) a quencher comprising a thiol, wherein the thiol is capable of reacting with the electrophilic group; and (c) a sufficient amount of a suitable base to reduce the level of an unwanted reaction of the pathogen inactivating compound with red blood cells in the mixture which comprises the red blood cell composition, the pathogen-inactivating compound, the quencher, and the base, relative to the mixture without the base. In some embodiments, the unwanted reaction of the pathogen inactivating compound with red blood cells is modification of the surface of the red blood cells by the pathogen inactivating compound.

In still another embodiment, the invention provides a method of treating a red blood cell composition, comprising mixing the following with the red blood cell composition: (a) a pathogen-inactivating compound, wherein the pathogen-inactivating compound comprises a nucleic acid binding ligand and a functional group which is, or which forms, an electrophilic group capable of reacting with nucleic acids; (b) a quencher comprising a thiol, wherein the thiol is capable of reacting with the electrophilic group; and (c) a sufficient amount of a suitable base to increase the pH of the mixture comprising the red blood cell composition, the pathogen-inactivating compound, the quencher, and the base, relative to the mixture without the base. In some embodiments (e.g., in some embodiments, where the quencher is an acidic compound), a sufficient amount of the suitable base is added to increase the pH of the mixture to at least about the pH of the mixture without either the base or the quencher.

In an additional aspect, the invention provides a method of improving the quenching of an unwanted side reaction of a pathogen-inactivating compound with red blood cells during treatment of a composition comprising the red blood cells with the pathogen-inactivating compound in the presence of a quencher, wherein the quencher comprises a thiol, and wherein the pathogen-inactivating compound comprises a functional group which is, or which forms, an electrophile reactive with the thiol of the quencher, wherein the method comprises increasing the pH of the reaction mixture comprising the red blood cell composition, the pathogen-inactivating compound, and the quencher. In some embodiments, the method further comprises the step of increasing the concentration of the quencher in the reaction mixture. In some embodiments, the unwanted reaction of the pathogen inactivating compound with red blood cells is modification of the surface of the red blood cells by the pathogen inactivating compound.

In some embodiments of each of the aforementioned methods, as well as other methods described herein, the method further comprises the step of reducing the concentration of pathogen inactivating compound in the mixture.

In some embodiments of each of the aforementioned methods, as well as other methods described herein, the red blood cell composition is treated ex vivo. In some other embodiments of each of the aforementioned methods, as well as other methods described herein, the red blood cell composition is treated in vitro.

Red blood cell compositions produced by each of the aforementioned methods, as well as other methods described herein, are also provided.

In further aspect, the invention provides kits, such as disposable kits for use in the processing of a red blood cell composition. These kits may be used for either manual processing, automated processing or both manual and automated processing. In some embodiments, the kit comprises a pathogen inactivating compound comprising a reactive electrophilic group, including any salts thereof, a quencher comprising a thiol group, including any salts thereof, and 1 or 2 equivalents of a suitable base, where an equivalent means a molar amount that is equivalent to the molar amount of quencher in the kit. In a preferred embodiment, the kit comprises β-alanine, N-(acridin-9-yl), 2-[bis(2-chloroethyl)amino]ethyl ester, including any salts thereof, glutathione, including any salts thereof, and 1 or 2 equivalents of a suitable base, where an equivalent means a molar amount that is equivalent to the molar amount of glutathione in the kit. In some embodiments, the β-alanine, N-(acridin-9-yl), 2-[bis(2-chloroethyl)amino]ethyl ester or any salt thereof is in solid form. In some embodiments, the β-alanine, N-(acridin-9-yl), 2-[bis(2-chloroethyl)amino]ethyl ester or any salt thereof is in solution. In some embodiments, the glutathione or any salt thereof is in solid form. In some embodiments, the glutathione or any salt thereof is in solution. In some embodiments, the 1 or 2 equivalents of base is in solid form. In some embodiments, the 1 or 2 equivalents of base is in solution. In some embodiments, the glutathione or any salt thereof and the 1 or 2 equivalents of base are present as a mixture. In some embodiments, mixture of glutathione or any salt thereof and 1 or 2 equivalents of base is a homogeneous mixture. In some embodiments, this homogeneous mixture is in solid form. In some embodiments this homogeneous mixture is in solution. In some embodiments, the kit comprises a solution for dissolving the β-alanine, N-(acridin-9-yl), 2-[bis(2-chloroethyl)amino]ethyl ester, or any salt thereof, which is in solid form. In some embodiments, the kit comprises a solution for dissolving the glutathione, or any salt thereof, which is in solid form. In some embodiments, the kit comprises a solution for dissolving the 1 or 2 equivalents of base, which is in solid form. In some embodiments, the kit comprises a solution for dissolving both the quencher, or any salt thereof, and the 1 or 2 equivalents of base, which are in solid form. In some embodiments the kit comprises a solution for dissolving the mixture of quencher and 1 or 2 equivalents of base. In some embodiments, the solids or solutions of the kit further comprise acceptable excipients, adjuvants, diluents, or stabilizers.

In one aspect, the invention provides a kit useful, e.g., for treating red blood cell compositions to inactivate pathogens, comprising a pathogen-inactivating compound comprising anucleic acid binding ligand and a functional group which is, or which forms, an electrophilic group (including any salt thereof) a quencher comprising a thiol group (including any salt thereof), and at least about 1 equivalent base, wherein an equivalent means a molar amount that is equivalent to the molar amount of quencher in the kit. In some embodiments, the kit comprises about 1 or about 2 equivalents of a suitable base.

In one aspect, the invention provides a kit for treating red blood cell compositions to inactivate pathogens, comprising a nucleic acid binding ligand and a functional group which is, or which forms, an electrophilic group (e.g., PIC-1), including any salt thereof, and a neutralized quencher comprising a thiol group (e.g., neutralized glutathione), including any salt thereof.

In still further aspects, the invention includes a composition comprising red blood cells, a pathogen inactivating compound comprising a reactive electrophilic group, and a quencher comprising a nucleophilic group that is capable of reacting with the electrophilic group, wherein the quencher is at a concentration in the range of about 2 mM to 40 mM, also about 4 mM to 40 mM, also about 5 mM to 30 mM, or about 10 mM to 30 mM, and the pH of the composition is in the range of about 6.8 to 8.5, also about 7.0 to 8.5, also about 7.2 to 8.5, or about 7.2 to 8.0. In some embodiments, the pathogen inactivating compound comprises a nucleic acid binding ligand and the quencher comprises a thiol group. A preferred embodiment includes a composition comprising red blood cells, β-alanine, N-(acridin-9-yl), 2-[bis(2-chloroethyl)amino]ethyl ester, and glutathione at a concentration in the range of about 2 mM to 40 mM, wherein the pH of the composition is in the range of about 6.8 to 8.5, also about 7.0 to 8.5, also about 7.2 to 8.5, or about 7.2 to 8.0. In some embodiments, the composition is at a red blood cell hematocrit in the range of about 1 to 100%, also about 10 to 90%, also about 35 to 80%, or about 40 to 70%. In some embodiments, the concentration of β-alanine, N-(acridin-9-yl), 2-[bis(2-chloroethyl)amino]ethyl ester is in the range of about 0.05 mM to 4 mM, also about 0.05 mM to 2 mM, also about 0.05 mM to 0.5 mM, or about 0.1 mM to 0.3 mM and the glutathione is in the range of about 5 mM to 40 mM, also about 5 mM to 30 mM, or about 10 mM to 30 mM.

In an additional aspect, the invention provides a composition comprising red blood cells, a pathogen inactivating compound comprising a nucleic acid binding ligand and a reactive electrophilic group, and a quencher comprising a thiol group that is capable of reacting with the electrophilic group, wherein the quencher is at a concentration greater than 2 mM, and the pH of the composition is at about 6.7 or higher. In some embodiments, the composition has a pH in the range of about 6.8 to 8.5, about 7.0 to 8.5, about 7.2 to 8.5 and about 7.2 to 8.0. For example, in some embodiments, the pH of the composition is in the range of about 7.0 to 8.5. In some embodiments, the composition comprises at least about 4 mM quencher or at least about 10 mM quencher. In some embodiments, the quencher is at a concentration in the range of about 4 to 40 mM or about 10 to 30 mM. For instance, in some embodiments, the quencher is at a concentration in the range of about 4 mM to 40 mM, and the pH of the composition is in the range of about 6.8 to 8.5. In some embodiments, the quencher is at a concentration of at least about 4 mM, and the pH of the composition is in the range of about 6.8 to 8.5.

Additional aspects are also provided by the present invention.

BRIEF DESCRIPTIONS OF THE DRAWINGS

FIG. 1 shows serum antibody titer during repeated transfusion in Phase 1 of Example 12. For clarity, error bars are shown for KLH-Acridine immunizations only. Error bars for RBC infusion groups were approximately ±1.

Figure 2:
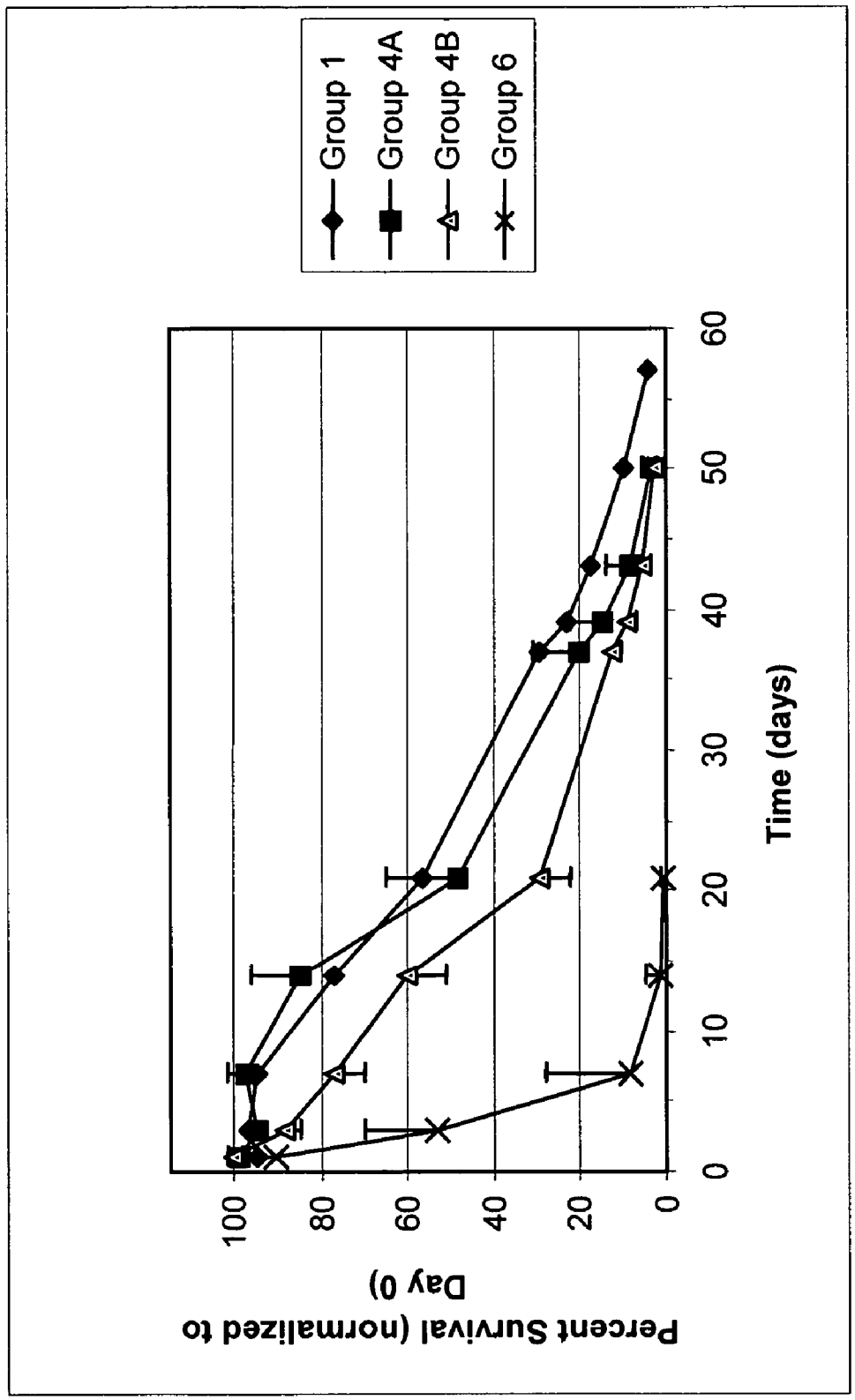

FIG. 2 shows the lifespan of Original S-220 RBC in Groups 4A, 4B and 6 in Phase 2 of Example 12. Lifespan was determined by extrapolating early time points to 100% at day 0. Group 1 animals received biotinylated Control RBC. Error bars are shown for Groups 4A, 4B and 6 only, for clarity.

Figure 3:
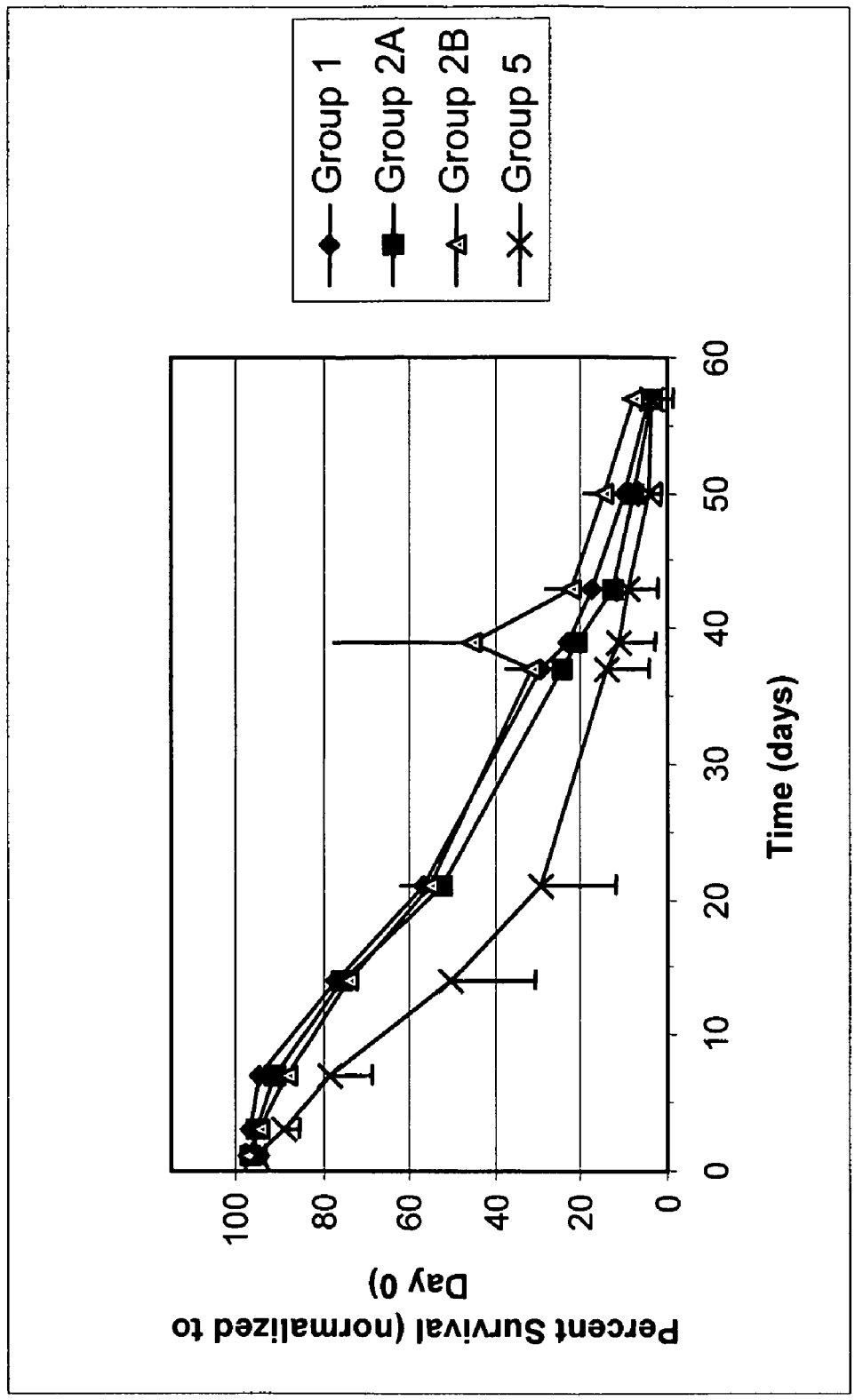

FIG. 3 shows lifespan of Original S-303 (PIC-1) RBC in Groups 2A, 2B and 5 in Phase 2 of Example 12. Lifespan was determined by extrapolating early time points to 100% at day 0. Group 1 animals received biotinylated Control RBC. Error bars are shown for Groups 2B and 5 only, for clarity.

Figure 4:
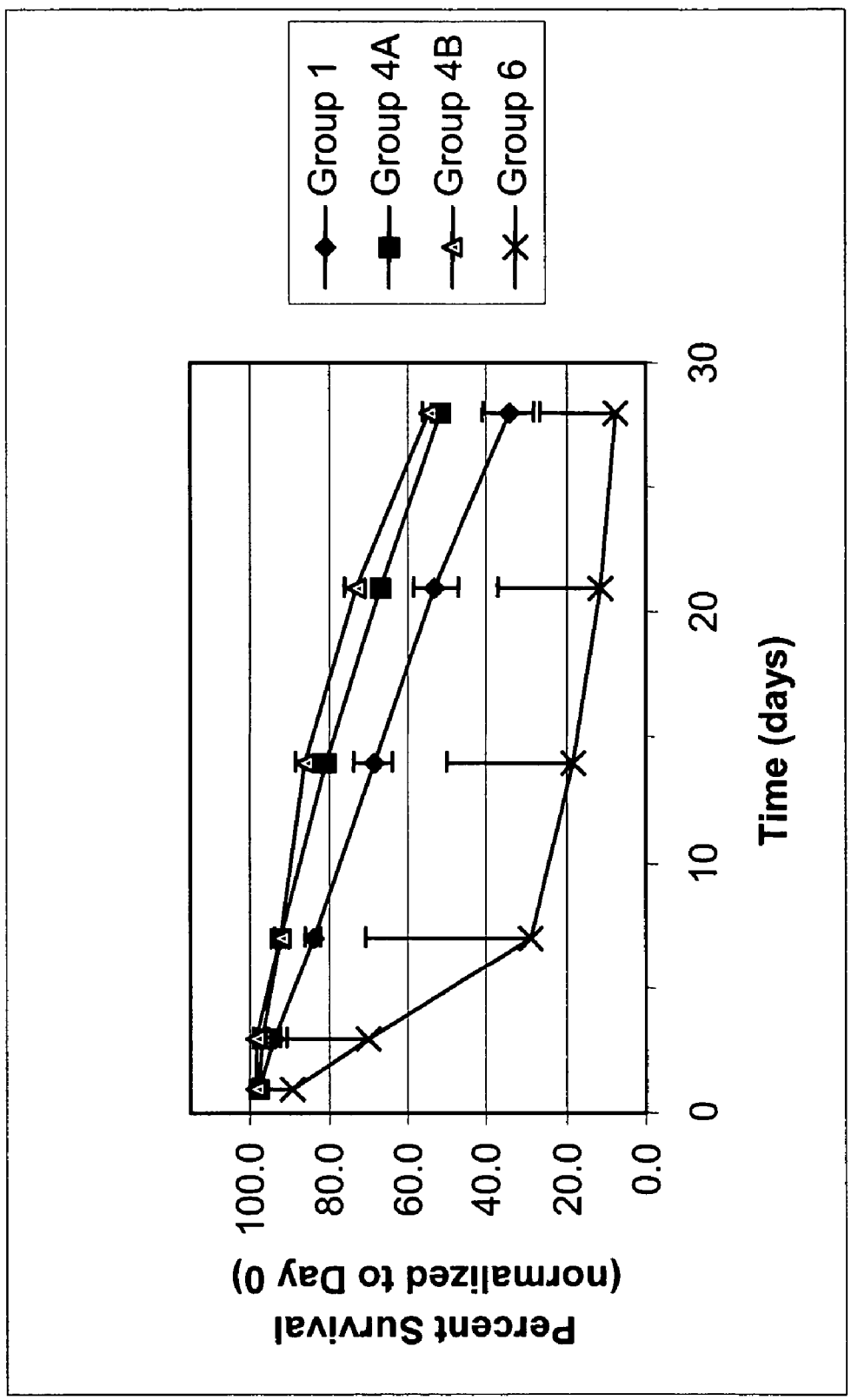

FIG. 4 shows the lifespan of Modified S-220 RBC in Groups 4A, 4B and 6 in Phase 2 of Example 12. Lifespan was determined by extrapolating early time points to 100% at day 0. Group 1 animals received biotinylated Control RBC. Error bars are shown for Groups 1, 4B and 6 only, for clarity.

Figure 5:
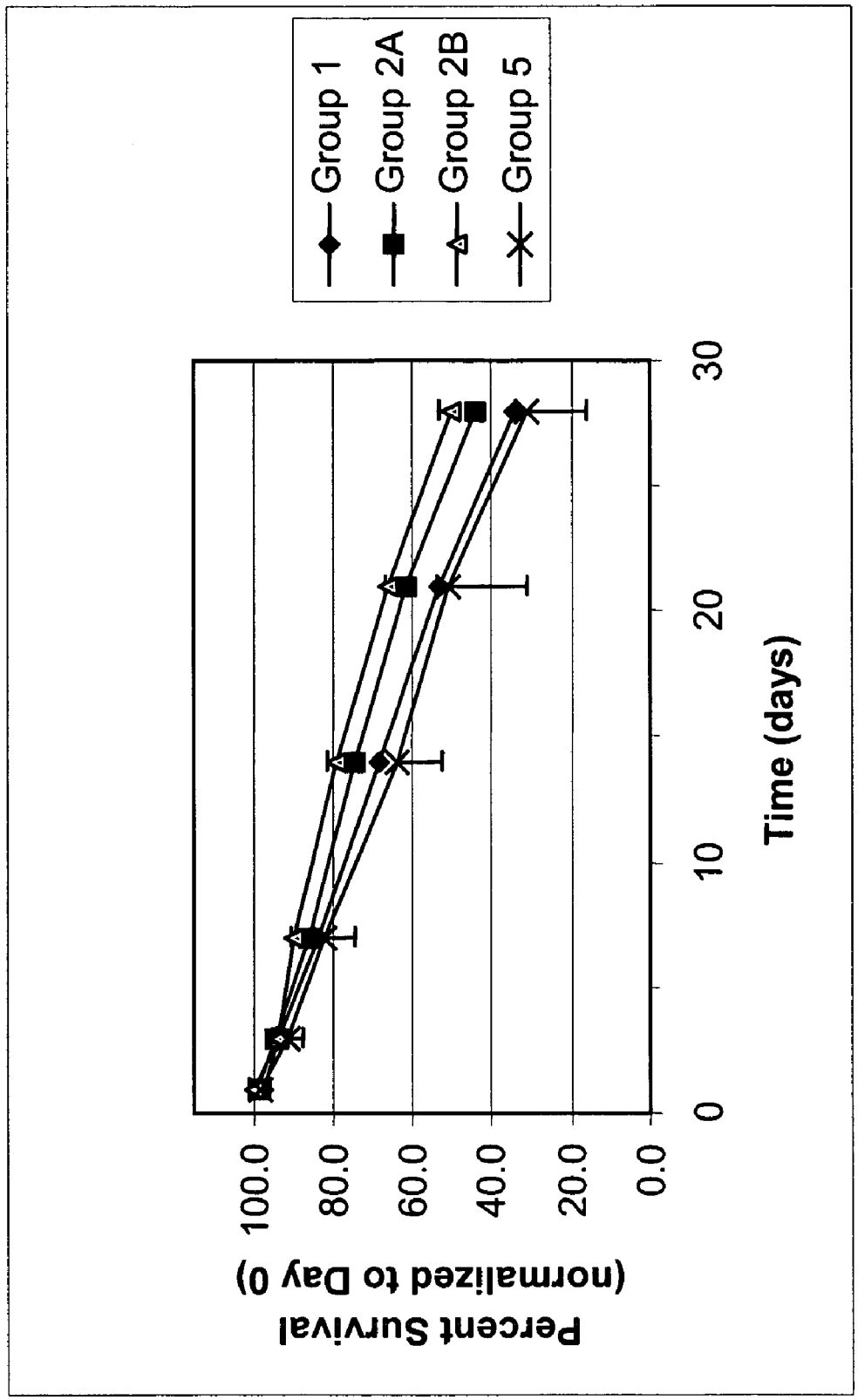

FIG. 5 shows the lifespan of Modified S-303 RBC in Groups 2A, 2B and 5 in Phase 2 of Example 12. Lifespan was determined by extrapolating early time points to 100% at day 0. Group 1 animals received biotinylated Control RBC. Error bars are shown for Groups 2B and 5 only, for clarity.

Figure 6:
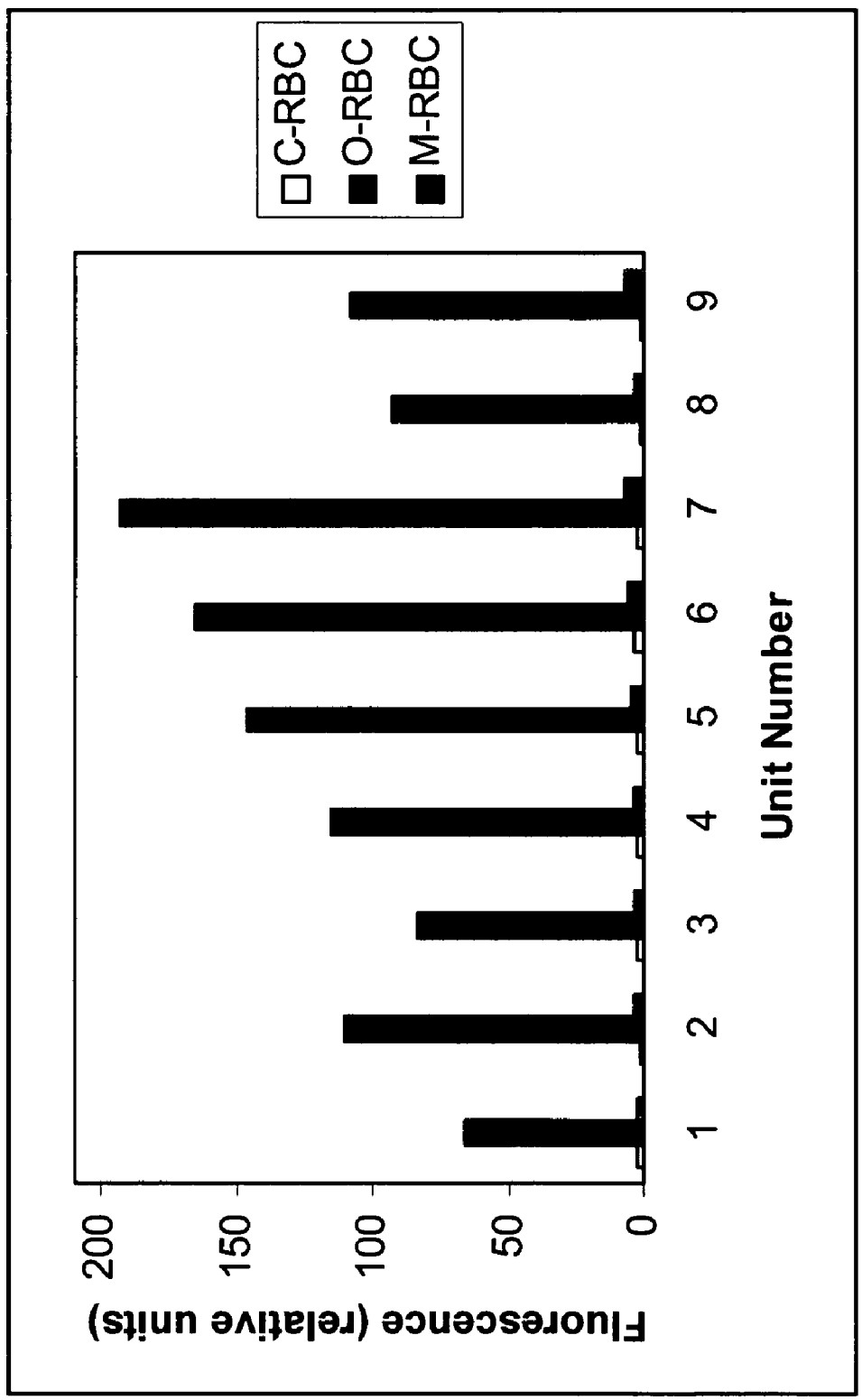

FIG. 6 shows the results of FACScan Analysis of S-303 Treated RBC.

DETAILED DESCRIPTION OF THE INVENTION

Existing methods for quenching of reactive electrophilic species in red blood cell compositions are provided, for example, in U.S. Pat. No. 6,709,810. As a non-limiting example of these methods, glutathione is used in combination with β-alanine, N-(acridin-9-yl), 2-[bis(2-chloroethyl) amino]ethyl ester (hereinafter referred to alternatively as "pathogen inactivating compound I," "PIC-1," or "S-303"). The glutathione is typically isolated in the acidic form (i.e. protonated), and this is the form used in these known methods. As such, when referring to known quenching methods, glutathione will be referred to as acidic or protonated glutathione. As used herein, the standard condition for inactivation of pathogens in red blood cells involves treating a red blood cell composition with protonated glutathione at 2 mM and PIC-1 at 0.2 mM. The protonated glutathione concentration may be increased, providing a higher ratio of quencher to pathogen inactivating compound, in an attempt to provide better quenching of unwanted side reactions. However, as the protonated glutathione concentration is increased, the overall pH of the red blood cell composition decreases due to the acidity of the glutathione. It has been determined that this lower pH results in insufficient quenching of the reaction of the pathogen inactivating compound with the red blood cells, particularly the surface of the red blood cells. It has also been determined that the standard condition does not provide adequate quenching of the modification of the red blood cell surface. As such, the present invention provides improved quenching methods, wherein the pH of a red blood cell composition comprising a pathogen inactivating compound and a quencher is adjusted to a suitable range to provide improved quenching, wherein the concentration of quencher used is greater than 2 mM, such as about 5 to 40 mM, also about 10 to 30 mM, or about 20 mM. For example, methods are provided such that upon mixing a composition comprising red blood cells with a pathogen inactivating compound and a quencher, the pH is in a suitable range, such as a pH of about 6.8 to 8.5, also about 7.0 to 8.5, also about 7.2 to 8.5, or about 7.2 to 8.0, wherein the quencher concentration is in the range of about 5 to 40 mM.

In some embodiments of each of the methods described herein, an undesired (also referred to herein as "unwanted") side reaction of the pathogen inactivating compound with the red blood cells is reduced. In some embodiments, the undesired side reaction that is reduced is modification of the red blood cell surface by the pathogen inactivating compound. In some embodiments, the level of side reaction is reduced by at least about 5%, at least about 10%, at least about 25%, at least about 50%, at least about 75%, or at least about 90%. The decrease in the side reaction (relative to a second method) may be evidenced, for example, by measuring the amount of binding to the treated red blood cells of antibodies specific to the pathogen inactivating compound and/or measuring the life span of the treated red blood cells in vivo, and comparing these measurements to red blood cells treated by a second, different method. For instance, in some embodiments of the improved methods, the level of anti-pathogen inactivating compound antibody binding to the treated blood cells is decreased by at least about 10%, at least about 25%, at least about 50%, at least about 75%, or at least about 90%, relative to a method without the improvements.

In some embodiments of each of the aspects of the invention described herein, the pH range suitable to provide adequate quenching of binding of the pathogen inactivating compound to the red blood cells is the pH range which provides improved quenching of the binding of the pathogen inactivating compound to the red blood cells relative to the standard treatment of a red blood cell composition with protonated glutathione at 2 mM and PIC-1 at 0.2 mM. In some embodiments, the improvement in quenching is evidenced by a decrease in the immunogenicity of the treated red blood cells relative to those treated by the standard method. In some embodiments, the improvement in quenching provided by a given method relative to the standard method is evidenced by a decrease in the amount of binding of antibodies specific to the pathogen inactivating compound to the treated red blood cells in vitro and/or by the increased life span of the treated red blood cells in vivo.

In one aspect, the invention provides a method of treating a red blood cell composition comprising: a) providing i) a pathogen inactivating compound comprising a reactive electrophilic group, ii) a quencher comprising a thiol group, and iii) a composition comprising red blood cells, wherein there is a possibility that the red blood cell composition is contaminated with a pathogen; and b) mixing the pathogen inactivating compound and quencher with the composition comprising red blood cells, wherein the resulting mixture is in a pH range suitable to provide adequate quenching of binding of the pathogen inactivating compound to the red blood cells. In some embodiments, the method further comprises a step of adjusting the pH of the composition comprising red blood cells. In some embodiments, the pH of the composition comprising red blood cells is adjusted prior to mixing with the pathogen inactivating compound and quencher. In some embodiments, the pH of the composition comprising red blood cells is adjusted by the addition of the quencher. In some embodiments, the quencher is neutralized with at least about one equivalent of a suitable base prior to addition of the quencher to the red blood cell composition. In some embodiments, the quencher is mixed with the composition comprising red blood cells prior to adding the pathogen inactivating compound. In some embodiments of the methods, the suitable pH range at room temperature is about 6.8 to 8.5, about 7.0 to 8.5, about 7.2 to 8.5, or about 7.2 to 8.0. In some embodiments, the concentration of quencher in the resulting mixture is in the range of about 2 mM to about 40 mM. In some embodiments, the concentration of the quencher in the resulting mixture is in the range of about 4 mM to about 40 mM, about 10 to about 30 mM. In some embodiments of the method, the concentration of quencher in the resulting mixture is at least about 4 mM or at least about 10 mM. In some embodiments, the quencher used in the method comprises cysteine or a derivative of cysteine. For instance, in some embodiments, the quencher is glutathione. The reactive electrophilic group is, in some embodiments, selected from the group consisting of a mustard, a mustard intermediate, and a mustard equivalent. In some embodiments, the pathogen inactivating compound is β-alanine, N-(acridin-9-yl), 2-[bis(2-chloroethyl)amino]ethyl ester. In some embodiments, the treatment results in an inactivation of at least 1 log of a pathogen contaminant in the red blood cell composition.

In another aspect, the invention provides a method of treating a red blood cell composition comprising: (a) providing i) a pathogen inactivating compound comprising a functional group which is, or which forms, a reactive electrophilic group, ii) a quencher comprising a thiol group, wherein the thiol is capable of reacting with the reactive electrophilic group of the pathogen-inactivating compound, and iii) a composition comprising red blood cells, wherein there is a possibility that the red blood cell composition is contaminated with a pathogen; and (b) mixing the pathogen inactivating compound and quencher with the composition comprising red blood cells, wherein the concentration of the quencher in the resulting mixture is greater than 2 mM, wherein the pH of the resulting mixture at room temperature is in the range of about 6.7 or higher. In some embodiments, the resulting mixture has a pH at room temperature of about 7.0 or higher, or about 7.2 or higher. In some embodiments, the pH of the resulting mixture is in a range of about 6.8 to 8.5, about 7.0 to 8.5, about 7.2 to 8.5, or about 7.2 to 8.0. For instance, in some embodiments, the pH of the resulting mixture at room temperature is in the range of about 7.0 to 8.5. In some embodiments, the method further comprises the step of (c) adjusting the pH of the composition comprising red blood cells so that the pH of the resulting mixture at room temperature is in the indicated range (e.g., in the range of about 7.0 to 8.5). In some embodiments, the pH of the composition comprising red blood cells is adjusted by the addition of at least about 0.5 equivalents, at least about 1 equivalent, or at least about 2 equivalents of base to the red blood cell composition, wherein an equivalent means a molar amount that is equivalent to the molar amount of quencher in the mixture. In some embodiments, the quencher is neutralized with at least about one equivalent of a suitable base prior to addition of the quencher to the red blood cell composition and the pH of the composition comprising red blood cells is adjusted by the addition of the neutralized quencher. In some embodiments, the concentration of quencher in the resulting mixture is at least about 4 mM or at least about 10 mM. In some embodiments, the concentration of the quencher in the resulting mixture is about 4 to 40 mM or about 10 to 30 mM. For instance, in some embodiments, the concentration of the quencher is at least about 4 mM, wherein the mixture has a pH at room temperature in the range of about 6.8 to 8.5. In some embodiments, the concentration of the quencher is about 4 to 40 mM and the pH at room temperature is in the range of about 7.2 to 8.5. In some embodiments, the quencher is neutralized with at least about one equivalent of a suitable base prior to addition of the quencher to the red blood cell composition. In some embodiments, the quencher is mixed with the composition comprising red blood cells prior to addition of the pathogen inactivating compound. In some embodiments, the quencher compound is acidic. In some embodiments, the quencher comprises cysteine or a derivative of cysteine. For instance, in some embodiments, the quencher is glutathione. In some embodiments, the functional group is selected from the group consisting of a mustard, a mustard intermediate, and a mustard equivalent. In some embodiments, the pathogen inactivating compound is β-alanine, N-(acridin-9-yl), 2-[bis(2-chloroethyl)amino]ethyl ester. In some embodiments, the treatment results in an inactivation of at least 1 log of a pathogen contaminant in the red blood cell composition. In some embodiments, the treatment results in an inactivation of at least 1 log, at least about 2 log, or at least about 3 log of a pathogen contaminant in the red blood cell composition.

In another aspect, the invention provides a method of treating a red blood cell composition, comprising mixing the following with the red blood cell composition: (a) a pathogen-inactivating compound, wherein the pathogen-inactivating compound comprises a nucleic acid binding ligand and a functional group which is, or which forms, an electrophilic group capable of reacting with nucleic acids; (b) a quencher comprising a thiol, wherein the thiol is capable of reacting with the electrophilic group; and (c) a sufficient amount of a suitable base to reduce the level of an unwanted side reaction of the pathogen inactivating compound with red blood cells in the mixture which comprises the red blood cell composition, the pathogen-inactivating compound, the quencher, and the base, relative to the mixture without the base (i.e., a second mixture comprising the same components as the first except that the base of (c) has not been added). In some embodiments, the unwanted reaction of the pathogen inactivating compound with red blood cells is modification of the surface of the red blood cells by the pathogen inactivating compound. In some embodiments, the base and quencher are combined with the red blood cell composition prior to, at the same time, or no more than about one hour, about 30 minutes, about 20 minutes, about 10 minutes, about 5 minutes, about 2 minutes, or about 1 minute after combining the pathogen-inactivating compound with the red blood cell composition. In some embodiments, the base and quencher are mixed with the red blood cell composition prior to mixing the pathogen-inactivating compound with the red blood cell composition. In some embodiments, the base and the quencher are mixed together prior to mixing either the base or the quencher with the red blood cell composition. In some embodiments, a basic salt comprising the quencher provides both the quencher and the base are both provided by a basic salt comprising the quencher. In some embodiments, the base is NaOH. In some embodiments, the base is a basic buffer. In some embodiments, at least about 0.5 equivalents, at least about 1.0, or at least about 2 equivalents of base are added, wherein an equivalent means a molar amount that is equivalent to the molar amount of quencher in the mixture. In some embodiments, the base comprises at least about 1 equivalent of base. In some embodiments of the methods, the suitable pH range at room temperature is about 6.8 to 8.5, about 7.0 to 8.5, about 7.2 to 8.5, or about 7.2 to 8.0. In some embodiments, the resulting mixture has a pH at room temperature of about 7.0 to 8.5. In some embodiments, the concentration of the quencher in the resulting mixture is greater than 2 mM, greater than about 4 mM, or greater than about 10 mM. In some embodiments, the concentration of quencher in the resulting mixture is in the range of about 2 mM to about 40 mM. In some embodiments, the concentration of the quencher in the resulting mixture is in the range of about 4 mM to about 40 mM, about 10 to about 30 mM. For instance, in some embodiments, the concentration of the quencher in the resulting mixture is in the range of about 10 mM to 30 mM. In some embodiments, the quencher is acidic. In some embodiments, the quencher comprises cysteine or a derivative of cysteine, such as glutathione. In some embodiments, the functional group is selected from the group consisting of a mustard, a mustard intermediate, and a mustard equivalent. For instance, in some embodiments, the pathogen inactivating compound is β-alanine, N-(acridin-9-yl), 2-[bis(2-chloroethyl)amino]ethyl ester. In some embodiments, the treatment results in an inactivation of at least 1 log of a pathogen contaminant in the red blood cell composition.

In still another embodiment, the invention provides a method of treating a red blood cell composition, comprising mixing the following with the red blood cell composition: (a) a pathogen-inactivating compound, wherein the pathogen-inactivating compound comprises a nucleic acid binding ligand and a functional group which is, or which forms, an electrophilic group capable of reacting with nucleic acids; (b) a quencher comprising a thiol, wherein the thiol is capable of reacting with the electrophilic group; and (c) a sufficient amount of a suitable base to increase the pH of the mixture comprising the red blood cell composition, the pathogen-inactivating compound, the quencher, and the base, relative to the mixture without the base (i.e., a second mixture comprising the same components as the first except that the base of (c) is not added to the mixture). In some embodiments (e.g., in some embodiments, where the quencher is an acidic compound), a sufficient amount of the suitable base is added to increase the pH of the mixture to at least about the pH of the mixture without either the base or the quencher. In some embodiments, the base and quencher are combined with the red blood cell composition prior to, at the same time, or no more than about one hour, about 30 minutes, about 20 minutes, about 10 minutes, about 5 minutes, about 2 minutes, or about 1 minute after combining the pathogen-inactivating compound with the red blood cell composition. In some embodiments, the base and quencher are mixed with the red blood cell composition prior to mixing the pathogen-inactivating compound with the red blood cell composition. In some embodiments, the base and the quencher are mixed together prior to mixing either the base or the quencher with the red blood cell composition. In some embodiments, a basic salt comprising the quencher provides both the quencher and the base are both provided by a basic salt comprising the quencher. In some embodiments, the base is NaOH. In some embodiments, the base is a basic buffer. In some embodiments, at least about 0.5 equivalents, at least about 1.0, or at least about 2 equivalents of base are added, wherein an equivalent means a molar amount that is equivalent to the molar amount of quencher in the mixture. In some embodiments, the base comprises at least about 1 equivalent of base. In some embodiments of the methods, the suitable pH range at room temperature is about 6.8 to 8.5, about 7.0 to 8.5, about 7.2 to 8.5, or about 7.2 to 8.0. In some embodiments, the resulting mixture has a pH at room temperature of about 7.0 to 8.5. In some embodiments, the concentration of the quencher in the resulting mixture is greater than 2 mM, greater than about 4 mM, or greater than about 10 mM. In some embodiments, the concentration of quencher in the resulting mixture is in the range of about 2 mM to about 40 mM. In some embodiments, the concentration of the quencher in the resulting mixture is in the range of about 4 mM to about 40 mM, about 10 to about 30 mM. For instance, in some embodiments, the concentration of the quencher in the resulting mixture is in the range of about 10 mM to 3 0 mM. In some embodiments, the quencher is acidic. In some embodiments, the quencher comprises cysteine or a derivative of cysteine, such as glutathione. In some embodiments, the functional group is selected from the group consisting of a mustard, a mustard intermediate, and a mustard equivalent. For instance, in some embodiments, the pathogen inactivating compound is β-alanine, N-(acridin-9-yl), 2-[bis(2-chloroethyl)amino]ethyl ester. In some embodiments, the treatment results in an inactivation of at least 1 log of a pathogen contaminant in the red blood cell composition.

In an additional aspect, the invention provides a method of improving the quenching of an unwanted side reaction of a pathogen-inactivating compound with red blood cells during treatment of a composition comprising the red blood cells with the pathogen-inactivating compound in the presence of a quencher, wherein the quencher comprises a thiol, and wherein the pathogen-inactivating compound comprises a functional group which is, or which forms, an electrophile reactive with the thiol of the quencher, wherein the method comprises increasing the pH of the reaction mixture comprising the red blood cell composition, the pathogen-inactivating compound, and the quencher. In some embodiments, the method further comprises the step of increasing the concentration of the quencher in the reaction mixture. In some embodiments, the quencher is acidic. In some embodiments, the unwanted reaction of the pathogen inactivating compound with red blood cells is modification of the surface of the red blood cells by the pathogen inactivating compound.

In a further aspect, the invention provides a method for treating a red blood cell composition comprising, in the following order: a) providing i) β-alanine, N-(acridin-9-yl), 2-[bis(2-chloroethyl)amino]ethyl ester, ii) neutralized glutathione, and iii) a composition comprising red blood cells, wherein there is a possibility that the red blood cell composition is contaminated with a pathogen; b) mixing the neutralized glutathione with the composition comprising red blood cells; c) incubating the mixture for an appropriate time interval; and d) mixing the β-alanine, N-(acridin-9-yl), 2-[bis(2-chloroethyl)amino]ethyl ester with the mixture of neutralized glutathione and the composition comprising red blood cells, wherein a pathogen, if present in the composition comprising red blood cells, is inactivated by at least 1 log. In some embodiments, the neutralized glutathione comprises glutathione to which has been added at least about one equivalent of base, wherein an equivalent means a molar amount that is equivalent to the molar amount of quencher. In some embodiments, the neutralized glutathione comprises glutathione (e.g., the free acid of glutathione) to which has been added about two equivalents of base.

Red blood cell compositions produced by each of the methods described herein are also provided. In some embodiments, the red blood cell compositions comprise reduced levels of modification of the surface of the red blood cells by the pathogen inactivating compound, relative to red blood cells produced by other methods involving treatment with the pathogen inactivating compound. In some embodiments, the red blood cell compositions produced by the treatment of the methods comprise degradation products of the pathogen inactivating compound (e.g., the reaction product of the quencher with the pathogen inactivating compound). In some embodiments, the red blood cell compositions produced by the treatments of the methods described herein comprise a reduced amount of pathogen inactivating compound comprising the reactive electrophilic group after completion of the treatment, relative to a red blood cells composition produced by another method involving treatment with the pathogen inactivating compound. In some embodiments, the amount of pathogen inactivating compound comprising the reactive electrophilic group in the composition has been reduced by about 10%, about 25%, about 50%, about 75%, about 90%, about 95%, or about 99%, relative to a composition treated by another method involving the pathogen inactivating compound (e.g., a method in which no quencher and/or base is added to the reaction mixture or a treatment at a lower pH).

In an additional aspect, the invention provides a composition comprising red blood cells, a pathogen inactivating compound comprising a nucleic acid binding ligand and a reactive electrophilic group, and a quencher comprising a thiol group that is capable of reacting with the electrophilic group, wherein the quencher is at a concentration greater than 2 mM, and the pH of the composition is at about 6.7 or higher. In some embodiments, the composition has a pH in the range of about 6.8 to 8.5, about 7.0 to 8.5, and about 7.2 to 8.0. In some embodiments, the composition comprises at least about 4 mM quencher or at least about 10 mM quencher. In some embodiments, the quencher is at a concentration in the range of about 4 to 40 mM or about 10 to 30 mM. For instance, in some embodiments, the quencher is at a concentration in the range of about 4 mM to 40 mM, and the pH of the composition is in the range of about 6.8 to 8.5. In some embodiments, the quencher is at a concentration of at least about 4 mM, and the pH of the composition is in the range of about 6.8 to 8.5.

With respect to the sequences herein which comprise amino acid substituents, as is evident to one skilled in the art, each amino acid substituent may be independently selected. The invention also provides sequences comprising amino acid substituents in which one or more of the amino acid substituents are eliminated.

A pathogen contaminant to be inactivated in the methods of the invention includes any nucleic acid-containing agent capable of causing disease in a human, other mammals, or vertebrates. The pathogenic agent may be unicellular or multicellular. Examples of pathogens are bacteria, viruses, protozoa, fungi, yeasts, molds, and mycoplasmas which cause disease in humans, other mammals, or vertebrates. The genetic material of the pathogen may be DNA or RNA, and the genetic material may be present as single-stranded or double-stranded nucleic acid. Table 1 lists examples of viruses, and is not intended to limit the invention in any manner.

TABLE 1

Non-limiting examples of viruses

| Family: | Virus: |
|---|---|
| Adeno | Adenovirus 2 |
| | Canine hepatitis |
| Arena | Pichinde |
| | Lassa |
| Bunya | Turlock |
| | California encephalitis |
| Herpes | Herpes simplex 1 |
| | Herpes simplex 2 |
| | Cytomegalovirus |
| | Pseudorabies |
| Orothomyxo | Influenza |
| Papova | SV-40 |
| Paramyxo | Measles |
| | Mumps |
| | Parainfluenza 2 and 3 |
| Picorna | Poliovirus 1 and 2 |
| | Coxsackie A-9 |
| | Echo 11 |
| Pox | Vaccinia |
| | Fowl Pox |
| Reo | Blue tongue |
| | Colorado tick fever |
| Retro | HIV |
| | Avian sarcoma |
| | Murine sarcoma |
| | Murine leukemia |
| Rhabdo | Vesicular stomatitis virus |
| Toga | Western equine encephalitis |
| | Dengue 2 |
| | Dengue 4 |
| | St. Louis encephalitis |
| Hepadna | hepatitis B |
| Bacteriophage | Lambda |
| | R17 |
| | T2 |
| (Rickettsia) | *R. akari* (rickettsialpox) |

In addition to inactivating possible pathogen contaminants, the methods of the present invention also inactivate leukocytes that may be present in the red blood cell composition. Leukoreduction methods are used to preferably remove most of the leukocytes from red blood cell compositions intended for infusion, as they may result in unwanted immune responses in the recipient. However, not all blood is leukoreduced, or leukoreduction methods do not remove all of the leukocytes. Therefore, inactivation of any residual leukocytes by the methods of the invention may further reduce the risk of such immune responses.

The methods of the invention include the ex vivo use of a pathogen inactivating compound and a quencher. The ex vivo use involves using the compounds for treatment of a red blood cell composition, outside of a living human, mammal, or vertebrate, where the treated biological material is intended for use inside of a living human, mammal, or vertebrate. For example, removal of blood from a human, and introduction of a compound into that blood to inactivate pathogens, is defined as an ex vivo use of the compound if the blood is intended for reintroduction into that human or another human. Reintroduction of the human blood into that human or another human would be in vivo use of the blood, as opposed to the ex vivo use of the compound. If the compound is still present in the blood when it is reintroduced into the human, then the compound, in addition to its ex vivo use, is also introduced in vivo. Some embodiments of the present invention involve the ex vivo use of a quencher, where the red blood cell composition is intended for in vivo use. In some instances, some level of quencher remains in the red blood cell composition such that the quencher is also introduced in vivo. The in vitro use of a material or compound involves a use of the material or compound outside of a living human, mammal, or vertebrate, where the material or compound is not intended for reintroduction into a living human, mammal, or vertebrate. An example of an in vitro use would be the diagnostic analysis of components of a red blood cell sample. The methods of the invention may be applied to the in vitro use of the red blood cell compositions, as modification of the red blood cells or other constituents may effect the in vitro analysis of the components of the blood sample. Thus, the methods of the invention may provide safety in handling of such in vitro samples with adequate quenching of modifications of the sample that might otherwise interfere with diagnostic testing of the sample.

Red blood cell compositions of the invention include, but are not limited to, any blood product comprising red blood cells, wherein the blood product provides, or is processed to provide, red blood cells suitable for human use, such as for infusion. Red blood cell compositions include, for example, whole blood and red blood cell concentrates, such as packed red blood cells. The red blood cell compositions may be described by their hematocrit, a measure of the concentration of red blood cells in the composition. Red blood cell compositions may have a hematocrit in the range of about 1 to 100%, more likely about 10 to 90%, also about 35 to 80%, or about 40 to 70%. Such red blood cell compositions may include chemicals, such as pathogen inactivating compounds and quenchers. They may also include buffers and other solutions, such as red blood cell additive solutions, including salts or buffered solutions. Any red blood cell composition that will come into contact with, or be introduced into, a living human, mammal, or vertebrate, where such contact carries a risk of transmitting disease due to contaminating pathogens may be treated as disclosed herein.

The inactivation of pathogens involves rendering pathogens in a material incapable of reproducing. Inactivation is expressed as the negative logarithm of the fraction of remaining pathogens capable of reproducing. Thus, if a compound at a certain concentration renders 90% of the pathogens in a material incapable of reproduction, 10% or one-tenth (0.1) of the pathogens remain capable of reproduction. The negative logarithm of 0.1 is 1, and that concentration of compound is said to have inactivated the pathogens present by 1 log. Alternatively, the compound is said to have 1 log inactivation or reduction at that concentration. Inactivating all but 1% or 0.1% of the pathogens would correspond to a 2 log or 3 log, respectively, reduction of pathogen at that concentration of the compound. Methods of determining the level of a particular pathogen in a material such as a composition comprising red blood cells are well known, and examples of such methods are provided in the examples.

In some embodiments of each of the methods and compositions described herein, the treatment of the red blood cell composition will result in an inactivation of at least about 1 log, at least about 2 log, or at least about 3 log of a pathogen contaminant, if present, in the red blood cell composition. In some embodiments, the pathogen is a bacterium, such as *Staphylococcus epidermidis, Serratia marcescens*, or *Yersinia enterocolitica*. In some other embodiments, the pathogen is a virus, such as vesicular stomatitis virus. In other embodiments, the treatment of the red blood cell composition does result in an inactivation of at least about 1 log, at least about 2 log, or at least about 3 log of a pathogen contaminant in the composition.

The inactivation of the pathogen in the red blood cell compositions is effected by contacting the pathogen in the red blood cell composition with a pathogen inactivating compound. Pathogen inactivating compounds that may be quenched by the methods of the invention include compounds that comprise a functional group which is, or which is capable of forming and has formed, e.g. in situ, a reactive group, such as an electrophilic group. The pathogen inactivating compounds of the present invention do not require photoactivation to be reactive. For example, the functional group may be a mustard group, a mustard group intermediate, a mustard group equivalent, an epoxide, a formaldehyde or a formaldehyde synthon. Such functional groups are capable of forming in situ a reactive group, such as an electrophilic aziridine, aziridinium, thiirane or thiiranium ion. A mustard group may be a mono- or bis-(haloethyl)amine group or a mono (haloethyl)sulfide group. A mustard equivalent is a group that reacts by a mechanism similar to the mustards, for example by forming reactive intermediates such as aziridinium and aziridine groups or thiirane and thiiranium groups. Examples include aziridine derivatives, mono or bis-(mesylethyl)amine groups, mono-(mesylethyl)sulfide groups, mono or bis-(tosylethyl)amine groups and mono-(tosylethyl)sulfide groups. A formaldehyde synthon is any compound that breaks down to a formaldehyde, which includes a hydroxylamine such as hydroxymethylglycine. The reactive group of the pathogen inactivating compound is capable of reacting with the nucleic acids of pathogens, for example with nucleophilic groups on the nucleic acid. The reactive group is also capable of reacting with a nucleophilic group of the quencher. Pathogen inactivating compounds may also include a component that targets the compound to nucleic acids, such as an anchor portion. The anchor portion comprises a moiety which is capable of binding non-covalently to a nucleic acid biopolymer, such as DNA or RNA, and is also referred to as a nucleic acid binding ligand, nucleic acid binding group, or nucleic acid binding moiety. Examples of such compounds are described in U.S. Pat. Nos. 5,691,132, 6,410,219, 6,136,586, 6,617,157, and 6,709,810, each of which is incorporated by reference herein. Another class of pathogen inactivating compounds that may be quenched by the methods of the invention comprise the above-mentioned reactive groups linked to a nucleic acid binding group via a hydrolysable linker, as described in U.S. Pat. No. 6,514,987, incorporated by reference herein. The anchor portion of the pathogen inactivating compounds has an affinity for nucleic acids. This affinity may be due to any of several modes of binding to the nucleic acid non-covalently, including, but not limited to, intercalation, minor groove binding, major groove binding, electrostatic binding (i.e. phosphate backbone binding), and sequence specific binding. Detailed examples of such nucleic acid binding moieties can be found in the above-mentioned patents.

In some embodiments of each of the methods, compositions, and kits described herein, the pathogen inactivating compound comprises a functional group which is, or which forms, a reactive electrophilic group reactive with the nucleophile of the chosen quencher. In some embodiments, the pathogen inactivating group comprises a nucleic acid binding ligand and a functional group which is, or which forms an electrophilic group.

A particular example of a suitable pathogen inactivating compound for use in the present invention is β-alanine, N-(acridin-9-yl), 2-[bis(2-chloroethyl)amino]ethyl ester (also alternatively referred to herein as "PIC-1" or "S-303"), the structure of which is as follows, including salts thereof.

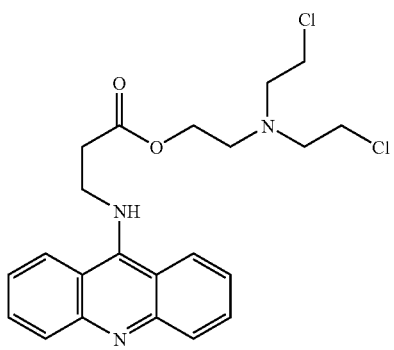

In some embodiments, the concentration of the pathogen inactivating compound, such as PIC-1, in the mixture with the red blood cell composition and the quencher is in the range of about 0.05 mM to 4 mM, about 0.05 mM to 2 mM, about 0.05 mM to 0.5 mM, or about 0.1 mM to 0.3 mM. In some embodiments, the molar ratio of quencher to pathogen inactivation compound once both components have been mixed with the red blood cell composition is about 10:1 to about 400:1, also about 10:1 to about 200:1, also about 20:1 to about 200:1, also about 50:1 to about 200:1, also about 100:1.

Quenchers for use in methods of the present invention are intended to reduce unwanted side reactions of the reactive electrophilic species used to inactivate pathogens. Suitable quenchers comprise a nucleophilic group that is capable of reacting with the electrophilic group of the pathogen inactivating compound, and are described in detail in U.S. Pat. No. 6,709,810, incorporated by reference herein in its entirety. The quenchers are capable of significantly reducing the unwanted side reactions in a red blood cell composition while allowing the pathogen inactivating compound to sufficiently inactivate a pathogen that may be contaminating the red blood cell composition. The improved methods of the present invention provide an effective amount of quencher in combination with an effective amount of pathogen inactivating compound under conditions which provide optimal reduction in unwanted side reactions combined with sufficient inactivation of pathogens. A variety of unwanted side reactions may be reduced, such as reaction with proteins and red blood cell components. In some embodiments, the quencher provides optimal reduction in the modification of the red blood cells, such as the binding of IgG to the red blood cells or binding of the pathogen inactivating compound to the red blood cells. While the methods of the invention involve the ex vivo treatment of red blood cell compositions, some quencher remains in the composition upon introduction into an individual. As such, the quenchers of the invention need to be suitable for infusion. Suitable quenchers include, but are not limited to, compounds comprising a thiol group, such as quenchers comprising the amino acid cysteine or a suitable derivative of cysteine, such as N-acetyl cysteine. Examples of such quenchers include cysteine and peptides comprising at least one cysteine, such as glutathione. In some embodiments, the suitable quenchers comprise a derivative of cysteine that can form a thiol group in situ, with or without the use of additional chemicals or added enzymes, such as S-acetyl cysteine or other suitable thiol derived prodrugs of cysteine, or peptides comprising S-acetyl cysteine or other suitable thiol derived prodrugs of cysteine. Suitable derivatives of cysteine are those which either comprise, or are capable of forming in situ, a cysteinyl thiol which is capable of reacting with the electrophilic group of the pathogen-inactivating compound.

Generally, due to the targeting of the pathogen inactivating compound to nucleic acids, sufficient amounts of pathogen inactivating compound are able to penetrate into the pathogen and react with the pathogen nucleic acid before it is quenched. The pathogen inactivating compound remaining in the extracellular environment, however, is adequately quenched to reduce unwanted side reactions. Thus, an effective amount of quencher in combination with an effective amount of pathogen inactivating compound is provided by the methods of the invention. In some embodiments, the quencher is able to quench unwanted side reactions in the extracellular environment of the red blood cell composition but does not significantly enter cells, such as red blood cells, viruses and bacteria. As such, the effective amount of pathogen inactivating compound may be provided so that sufficient pathogen inactivating compound penetrates into the pathogen before it is quenched in the extracellular environment. In some embodiments, the quencher comprises cysteine or a suitable derivative of cysteine and does not significantly penetrate into a pathogen, such as a virus or bacteria. Such quenchers include peptides wherein at least one of the amino acids is cysteine, N-acetyl cysteine, S-acetyl cysteine, or other suitable derivative of cysteine. In some embodiments, the quencher comprises a peptide (e.g., 2-10 amino acids) comprising cysteine.

In some embodiments, the quencher is a peptide of 2 to 10 amino acids, wherein at least one of the amino acids is cysteine, N-acetyl cysteine, S-acetyl cysteine, or other suitable derivative of cysteine. In some embodiments, the quencher is a peptide of at least 3 amino acids, such as about 3-10 amino acids, also about 3-6 amino acids, wherein at least one of the amino acids is cysteine, N-acetyl cysteine, S-acetyl cysteine, or other suitable derivative of cysteine. In some embodiments the quencher is a peptide of at least 3 amino acids, such as about 3-10 amino acids, also about 3-6 amino acids, wherein at least one of the amino acids is cysteine, N-acetyl cysteine, S-acetyl cysteine, or other suitable derivative of cysteine, also wherein at least 2 or at least 3 of the amino acids is cysteine, N-acetyl cysteine, S-acetyl cysteine, or other suitable derivative of cysteine. A preferred quencher is glutathione (also known as L-glutathione and γ-L-glutamyl-L-cysteinyl-glycine).

In some embodiments, the quencher is glutathione in its reduced form. Glutathione disulfide, the oxidized form of glutathione, may also be used, so long as the glutathione disulfide is sufficiently reduced in solution prior to addition of the solution to the mixture comprising the red blood cell composition or sufficiently reduced after addition to the mixture comprising the red blood cell composition.

In some embodiments, the quencher is a derivative of glutathione, such as a glutathione monoalkyl ester or dialkyl ester, wherein the alkyl group is a straight or branched group having 1 to 10 carbon atoms. Specific examples of alkyl groups include, but are not limited to methyl group, ethyl group, propyl group, isopropyl group, butyl group, isobutyl group, tert-butyl group, pentyl group, isopentyl group, neopentyl group, tert-pentyl group, 1-methylbutyl group, hexyl group, isohexyl group, 2-methylpentyl group, 1-ethylbutyl group, heptyl group, octyl group, nonyl group, and decyl group. For instance, non-limiting examples of glutathione derivatives include glutathione methyl ester, glutathione monoethyl ester, and glutathione monoisopropyl ester. In some embodiments, glutathione oxidized diethyl ester (GSSG-(glycyl)-diethyl-ester) is used. In some embodiments, a thioester of glutathione is hydrolyzed after addition to the red blood cell compositions to form the thiol.

It is understood that in some embodiments, the quencher will be provided in the form of a free acid or base, whereas, in other embodiments, the quencher will be provided in the form of a salt. If the quencher is in the form of a salt, the salt is preferably a pharmaceutically acceptable salt. The pharmaceutically-acceptable salts of compounds (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-napthalensulfonate, nicotinate, oxalate, pamoate, pectinate, persulfate, 3-phenylpropionate, phosphate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, didbutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

For example, in some embodiments, the quencher is in the form of a pharmaceutically acceptable salt formed from glutathione. In some embodiments, the quencher is in the form of a pharmaceutically acceptable salt formed from glutathione and one or more cations such as sodium, aluminum, calcium, lithium, magnesium, zinc, or tetramethylammonium. In some embodiments, the quencher is glutathione (reduced) and is provided in the form of glutathione monosodium salt (available, e.g., from Biomedica Foscama, Italy). In some other embodiments, the glutathione (reduced) is provided in the form of glutathione hydrochloride salt. In some other embodiments, the glutathione is provided in the form of a glutathione (reduced) disodium salt. In further embodiments, a glutathione monoalkyl ester sulfate is used. In some embodiments, glutathione is provided in the form of glutathione oxidized disodium salt.

In some embodiments, the quencher is mixed with the red blood cell composition and/or pathogen-inactivating compound in neat form. In some embodiments, the quencher that is mixed with the red blood cell composition and/or pathogen-inactivating compound is in aqueous solution. In some embodiments, the quencher is a neutralized quencher in aqueous solution. For example, in some embodiments, the quencher may be an acidic compound in aqueous solution to which at least one equivalent (e.g., about one or two equivalents) of base has been added.

The quenching methods of the present invention involve the combination of a red blood cell composition with a pathogen inactivating compound and a quencher under conditions where, upon mixing the composition with the pathogen inactivating compound and quencher, the pH of the resulting composition is in a suitable range to provide adequate pathogen inactivation with improved reduction of unwanted side reactions, such as modification of the red blood cells. The improved methods include three features that may be important to the quenching methods. The first feature is the thiol group, or other suitable nucleophilic group. The second is the adjustment of the pH of the solution. It is possible to provide some level of quenching just by suitably adjusting the pH of the solution. As such, the quenchers of the invention provide some buffering capacity to the composition comprising red blood cells, where the buffering capacity itself provides improved quenching. For example, using a cysteine analog such as methionine as a quencher, when appropriately modified to provide a suitable pH change in the red blood cell composition, will result in some level of quenching of binding of the pathogen inactivating compound to the red blood cells. As the sulfur atom in methionine is not nucleophilic, methionine does not provide any quenching other than providing the necessary pH of the solution. Thus, the combination of pH adjustment and a thiol group provides further improvement to the quenching methods of the invention. A third feature that may be important for providing improved quenching in some embodiments are preferred quenchers that do not substantially penetrate inside of pathogens such as viruses and bacteria. Such quenchers provide adequate quenching in the extracellular environment, where detrimental reactions such as binding to red cell surfaces occur, without additional quenching of pathogen inactivating compound once it has penetrated inside of the pathogen.

With respect to the feature of adjusting the pH of the red blood cell composition, the existing methods of quenching such pathogen inactivating compounds fail to realize the importance of the pH of the resulting mixture. While higher amounts of quencher are demonstrated in known methods as providing adequate pathogen inactivation, these methods do not adequately describe the effects on the modification of the red blood cells when higher amounts of quenchers such as protonated glutathione are used. As the examples herein demonstrate, use of higher amounts of quenchers such as acidic glutathione do not adequately reduce the level of modification of the red blood cells. Because the glutathione is acidic, the higher levels bring the pH of the red blood cell composition to unacceptably low levels, at which quenching of the unwanted side reactions of the pathogen inactivating compound is ineffective. Thus, one aspect of the present invention involves ensuring that the pH of the red blood cell composition is maintained at a suitable level upon adding the pathogen inactivating compound and quencher. In some embodiments, upon mixing the pathogen inactivating compound and quencher with the red blood cell composition, the pH of the mixture is in the range of about 6.8 to 8.5, also about 7.0 to 8.5, also about 7.2 to 8.5, or about 7.2 to 8.0. While the pH in a red blood cell composition may change with time, it is desirable that the pH is in a desired range when quencher is added to the red blood cell composition, whether or not it already contains pathogen inactivating compound. The methods of the present invention involve adding pathogen inactivating compound and quencher to a red blood cell composition. The desired pH range is necessary upon the addition of both the pathogen inactivating compound and quencher regardless of the order of addition of the pathogen inactivating compound an/or quencher to the red blood cell composition. In other words, once all three components have been mixed, the pH is within the desired range. In some embodiments, quencher is added prior to pathogen inactivating compound. In some embodiments, pathogen inactivating compound is added prior to quencher. In some embodiments, quencher and pathogen inactivating compound are added essentially simultaneously. Thus, upon addition of pathogen inactivating compound and quencher means at the point when both of the quencher and pathogen inactivating compound have been mixed with the red blood cell composition. The desired pH can be achieved by several means, and is not limited as to when the pH of the red blood cell composition is adjusted, or in some embodiments is not significantly adjusted from the natural pH of the blood product. For example, the desired pH of the red blood cell composition can be achieved by adjusting the pH. The pH adjustment may be done, for example, by addition of a suitable additive solution, such as a buffering solution, prior to adding the pathogen inactivating compound and quencher. In some embodiments, the red blood cell composition may be washed one or more times with a suitable buffer before suspending in the same or other suitable buffer. Alternatively, the pH of the red blood cell composition can be adjusted simultaneously with the addition of either the pathogen inactivating compound, the quencher, or both. In some embodiments, the pH is adjusted simultaneously with addition of the quencher. In a preferred embodiment, the quencher is neutralized, such that addition of the neutralized quencher provides the desired pH range in the red blood cell composition. As an example, the neutralization of glutathione can be used to effect the necessary pH adjustments. Because glutathione comprises glutamic acid, the pH of the protonated form is acidic. Without being bound by theory, the probable neutralization of protonated glutathione is shown in the following scheme:

aqueous solution prior to mixing with the red blood cell composition, or may be added directly to the red blood cell composition in solid form. In some embodiments, the basic salt comprises the quencher and provides both the quencher and the base to the mixture. In some embodiments, the base used in the method is a strong base, such as NaOH. Typically, a strong base like NaOH will be dissolved first in aqueous solution prior to mixing with the red blood cell composition. In some embodiments, the strong base (in solution or in solid form) is mixed with the quencher prior to mixing the quencher with the red blood cell composition. In some embodiments, the base is a basic buffer (added in sufficient quantities and having an appropriate pKa to bring the mixture to the desired pH range). If a basic buffer is used, the buffer will, in some embodiments, be a pharmaceutically acceptable buffer. In some embodiments, the buffer will have a titratable proton with a pKa in the range of about 7 to 8. Examples of buffers which can be used as basic buffers include, but are not limited to, N-(2-hydroxyethyl)-piperazine-N'-2-ethanesulfonic acid (HEPES), phosphate buffered saline (PBS), and sodium phosphate buffer. Other suitable basic buffers will be readily identifiable by one of ordinary skill in the art.

In some embodiments of each of the methods and compositions described herein, the pH of the mixture of red blood cells, quencher, pathogen inactivating compound, and any added base is greater than about 6.7, greater than about 7.0, or greater than about 7.2. In some embodiments of each of the methods and compositions described herein, the pH of the mixture of red blood cells, quencher, pathogen inactivating

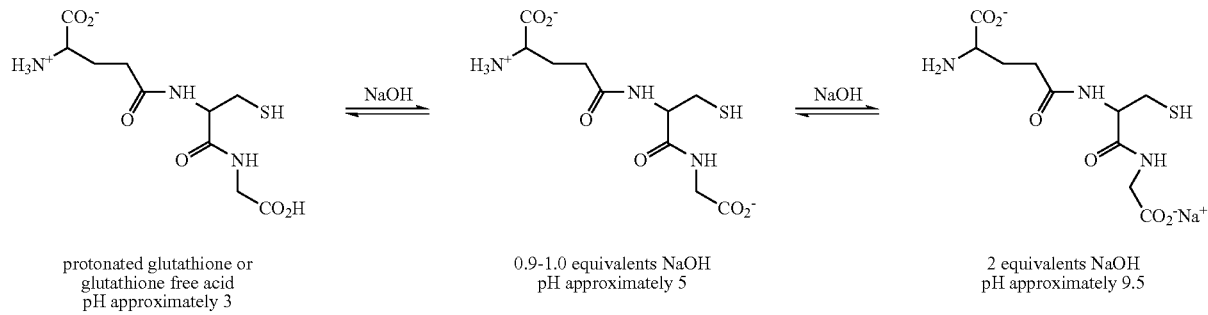

protonated glutathione or
glutathione free acid
pH approximately 3

0.9-1.0 equivalents NaOH
pH approximately 5

2 equivalents NaOH
pH approximately 9.5

As such, an appropriate level of neutralization of the glutathione can be used, for example by addition of 2 equivalents of base, to provide a quencher that, upon addition to a red blood cell composition, will provide the necessary pH adjustment of the composition. The appropriate neutralization will depend upon the quencher used. For example, when a peptide is used it will depend on the amino acid components of the peptide. In some embodiments, a quencher can be used that does not significantly affect the pH of the red blood cell composition. For example, use of a peptide comprising a cysteine that may further comprise one or more amino acids that result in a more neutral pH for a solution of the naturally isolated peptide. In some embodiments, the peptide further comprises at least one basic amino acid, such as arginine or lysine.

In some embodiments of the methods described herein where a base is mixed with the red blood cell composition along with the pathogen-inactivating compound and quencher to increase the pH of the mixture to a desired level and/or to improve quenching of undesired side reactions, the base is a basic salt. The basic salt may first be dissolved in an compound, and base (if any is added) is in the range of about 6.8 to 8.5, also about 7.0 to 8.5, also about 7.2 to 8.5, or about 7.2 to 8.0. In some preferred embodiments, the indicated pH is the pH at room temperature. For example, in some embodiments, the composition comprising the red blood cells are treated with the pathogen-inactivating compound in the presence of the quencher and any added base, wherein the pH of the mixture is in the range of about 7.2 to about 8.0.

In some embodiments, the pH of the mixture of red blood cells, quencher, and the base (if base is added as part of the method) is in the range of about 6.8 to 8.5, about 7.0 to 8.5, about 7.2 to 8.5, or about 7.2 to 8.0, prior to mixing the pathogen inactivating compound with the red blood cell composition. In some other embodiments, the pH is achieved at the same time as or within about 1 hour, within about 30 minutes, within about 20 minutes, within about 10 minutes, within about 5 minutes, or within about 2 minutes of mixing the pathogen inactivating compound with the composition comprising the red blood cells. In some embodiments of those methods where the pH is adjusted, the pH is adjusted to the desired pH range prior to, at the same time as, within about 1 hour, within about 30 minutes, within about 20 minutes, within about 10 minutes, within about 5 minutes, or within about 2 minutes of mixing the pathogen inactivating compound with the composition comprising the red blood cells. In those embodiments, where the quencher is glutathione and the pathogen-inactivating compound is PIC-1, the pH of the mixture comprising the red blood cell composition and the quencher is preferably adjusted to the desired pH range (e.g., pH 7.2 to 8.0) prior to mixing the PIC-1 with the red blood cell composition.

In some embodiments, the resulting pH of the final composition is not necessarily an adjustment of the pH of the starting red blood cell composition. For example, a red blood cell composition may have a pH in the desired range of 6.8-8.5, and the pH of the composition does not change significantly on addition of quencher, and subsequently pathogen inactivating compound. In such embodiments, the quencher either naturally provides the desired pH, or is neutralized accordingly to provide the desired pH. It is the combination of adding high amounts of quencher, such as about 5 mM to about 40 mM, with a resulting pH in the desired range that is important. Known methods using such concentrations of glutathione, for example, have not been used with the desired pH range of the present invention. Thus, for peptides, regardless of the peptide quencher, it can be effectively neutralized as needed to provide a suitable pH range when added to a red blood cell composition, and further may be selected to provide a suitable amount of buffering in the desired pH range. As such, a neutralized quencher means that the quencher is suitably titrated with acid or base as needed such that on addition to a red blood cell composition, the resulting mixture has a pH that provides better quenching of unwanted side reactions, such as a pH in the range of about 6.8 to 8.5, also about 7.0 to 8.5, also about 7.2 to 8.5, or about 7.2 to 8.0. In some embodiments, the peptide as isolated naturally is suitably neutralized, i.e. requires no addition of acid or base to provide the desired pH in the final mixture. Further, preferred quenchers will provide buffering capacity to maintain the pH in the desired range for a time necessary to quench unwanted side reactions.

In some embodiments of each of the methods and compositions described herein, the quencher is neutralized. A quencher is said to be "neutralized" by a base, if a sufficient amount of the base has been combined with the quencher, such that the quenching of an undesired side reaction between the pathogen inactivating compound and the red blood cells is improved in a mixture comprising the composition comprising the red blood cells, the pathogen inactivating compound, and quencher. A "neutralized quencher" does not necessarily have a neutral pH. In some embodiments, where the quencher is very acidic, the pH of the neutralized quencher may still be lower than 7.0. In some embodiments, the pH of solution of the neutralized quencher may be greater than 7.0. In some embodiments, the pH of the solution of the neutralized quencher will be detectably higher than that of the quencher prior to addition of the base. In some embodiments, the quencher is neutralized with at least about 0.25 equivalents, at least about 0.5 equivalents, at least about 0.75 equivalents, at least about 1 equivalent, or at least about 2 equivalents of a base. In some embodiments, the quencher is neutralized with about 1 to about 2 equivalents of base. In some embodiments, the quencher is neutralized with about 1 equivalent of base. In other embodiments, the quencher is neutralized with about 2 equivalents of base. For example, in some embodiments of the invention, glutathione is neutralized with about 2 equivalents of a suitable base, such as sodium hydroxide. In this instance, a solution of the protonated glutathione has a pH of approximately 3, while the solution neutralized with 2 equivalents of sodium hydroxide has a pH of approximately 9.5. Any appropriate peptide quencher comprising at least one cysteine can be suitably adjusted to provide the desired pH upon addition to the red blood cell composition. In addition to providing a quencher that is suitably pH adjusted or neutralized, in some embodiments, preferred quenchers are not able to significantly enter into the pathogens, such that they optimally quench unwanted reactions in the extracellular environment, but do not interfere with pathogen inactivation once the pathogen inactivating compound has penetrated inside of the pathogen.

In some embodiments of each of the methods described herein, the quencher is an acidic compound. In some embodiments, the quencher is provided in the free acid form. In some embodiments, the quencher is acidic and at least about 1 equivalent of base is added to neutralize the quencher. A solution comprising such a neutralized quencher may, in some instances, be basic, neutral, or even still acidic. In some embodiments about 1 equivalent of base is added to neutralize the quencher. In some embodiments, about 2 equivalents of base are added. In some embodiments, the quencher is acidic and about 1 to about 2 equivalents of base are used to neutralize the quencher. In some embodiments, about 1 or about 2 equivalents of base are used.

In some embodiments, the quencher is neutralized prior to addition to the red blood cell composition and/or pathogen-inactivating compound. In other embodiments, the quencher is neutralized after combining the quencher with either the red blood cell composition and/or pathogen-inactivating compound.

In some embodiments, the quencher is glutathione and is provided in the form of glutathione monosodium salt and is neutralized with about 1 equivalent of base. In some other embodiments, the quencher is glutathione and is provided in the form of glutathione hydrochloride salt and is neutralized with about 2 equivalents of base.

In some embodiments, the concentration of the quencher in the mixture comprising the red blood cell composition, quencher, pathogen-inactivating compound, and any added base is greater than 2 mM, greater than about 4 mM, or greater than about 10 mM. In some embodiments, the quencher concentration in the mixture is in the range of about 2 mM to 100 mM, about 2 mM to 40 mM, about 4 mM to 40 mM, about 5 mM to 40 mM, about 5 mM to 30 mM, or about 10 mM to 30 mM. In some embodiments, the quencher concentration in the mixture is about 20 mM. In some embodiments of each of the methods and compositions described herein, the concentration of quencher in the mixture is greater than 2 mM, greater than about 4 mM, or greater than about 10 mM, and the pH of the mixture of red blood cells, quencher, and the concentration of the pathogen inactivating compound is greater than about 6.7, greater than about 7.0, or greater than about 7.2. In some embodiments of each of the methods and compositions described herein, In some embodiments, the concentration of the quencher in the mixture is in the range of about 2 mM to 40 mM, about 4 mM to 40 mM, about 5 mM to 40 mM, about 5 mM to 30 mM, or about 10 mM to 30 mM, and the pH of the mixture of red blood cells, quencher, and pathogen inactivating compound is in the range of about 6.8 to 8.5, also about 7.0 to 8.5, also about 7.2 to 8.5, or about 7.2 to 8.0. In some embodiments of each of the methods and compositions described herein, the concentration of quencher in the mixture is greater than 2 mM, greater than about 4 mM, or greater than about 10 mM, and the pH of the mixture of red blood cells, quencher, and pathogen inactivating compound is in the range of about 6.8 to 8.5, also about 7.0 to 8.5, also about 7.2 to 8.5, or about 7.2 to 8.0. In some embodiments, the concentration of quencher (e.g., glutathione) in the mixture is in the range of about 4 mM to about 40 mM, and the pH of the mixture is in the range of about 7.2 to 8.0. In some embodiments, the concentration of quencher in the mixture is in the range of about 10 mM to about 30 mM, and the pH of the mixture is in the range of about 6.8 to 8.5.

In a preferred embodiment, the quencher is neutralized glutathione. Glutathione has many properties that make it particularly useful as a quencher. It is normally present in all cell types. It is not believed to be able to passively penetrate into a pathogen, such as by passing through cell membranes or lipid coats, of bacteria and lipid-enveloped viruses, or by passing through the viral capsid of non-enveloped viruses. At pH 7, glutathione is charged and in the absence of active transport does not penetrate lipid bilayers to any significant extent. This is consistent with inactivation of lipid enveloped viruses such as HIV and VSV being substantially unaffected by glutathione, including using concentrations of neutralized glutathione greater than 2 mM. The use of glutathione does have some effect on inactivation of *Yersinia enterocolitica*, *Staphylococcus epidermidis* and *Serratia marcescens*. However, this can be managed by using effective amounts of neutralized glutathione and pathogen inactivating compound. As such, preferred methods of quenching are provided wherein contamination of a red blood cell composition by a viral or bacterial pathogen is inactivated by at least 2 log, preferably at least 3 log. In some embodiments, *Staphylococcus epidermidis* may be inactivated by up to at least 3 log, also about 4 log, or about 5 log and VSV can be inactivated by up to at least 4 log, also about 5 log, or about 6 log. Further, the inactivation is within about 3 log, also about 2 log, preferably about 1 log that of the standard treatment of the red blood cell composition with 2 mM acidic glutathione and 0.2 mM PIC-1. In some embodiments, the inactivation of *Staphylococcus epidermidis* with PIC-1 is within about 3 log, also about 2 log, or about 1 log that of a similar composition inactivated with 2 mM acidic glutathione and 0.2 mM PIC-1. In some embodiments, the inactivation of VSV with PIC-1 is within about 2 log, or about 1 log, or essentially equal to that of a similar composition inactivated with 2 mM acidic glutathione and 0.2 mM PIC-1. Glutathione is also compatible with in vitro storage of red blood cells and the resulting red blood cell composition is suitable for introduction in vivo.

Appropriate methods for neutralizing glutathione and other quenchers will be readily apparent to those of ordinary skill in the art. In some embodiments, sodium hydroxide is used to neutralize the quencher. In some embodiments, solid pellets of NaOH are first dissolved in water to generate a concentrated solution of the base, such as a 1 N, 5 N, 10 N, or 20 N NaOH solution. In some embodiments, an appropriate amount of that NaOH solution is then added to the quencher either prior to, at the same time as, or following addition of the quencher to the mixture. Alternatively, the NaOH is added to the red blood cell composition or the pathogen-inactivating compound, or the combination of the two, prior to the addition of the quencher to the mixture.

The quencher and/or added base (or the neutralized quencher) used in the methods described herein may be mixed with the red blood cell composition prior to, at the same time as, or after addition of the pathogen inactivating compound to the red blood cell composition. If the quencher and base (or neutralized quencher) are mixed with the red blood cell composition after the pathogen-inactivating solution is mixed with the red blood cell composition, the quencher and/or base (or neutralized quencher) are preferably added to the red blood cell composition before a significant amount of side reaction of the pathogen inactivating compound with the red blood cells has occurred, so that adequate quenching of the undesired side reaction can be achieved. In some embodiments, the quencher and/or base (or neutralized quencher) are mixed with the red blood cell composition within about an hour, within about 30 minutes, within about 20 minutes, within about 10 minutes, within about 5 minutes, within about 2 minutes, or within about 1 minute after mixing the pathogen inactivating compound with the red blood cell composition. In some embodiments, the quencher and/or base (or neutralized quencher) are mixed with the red blood cell composition prior to mixing the pathogen inactivating compound with the red blood cell composition. For instance, in some embodiments where neutralized glutathione and PIC-1 are used in the methods, the neutralized glutathione is mixed with the red blood cells prior to, at the same time as, or within about 10 minutes after mixing the PIC-1 with the red blood cell composition.

In some embodiments, the quencher and/or base (or neutralized quencher) are mixed with the red blood cell composition prior to mixing the pathogen inactivating compound with the red blood cell composition.

In some embodiments of each of the methods described herein, the quencher and the added base (or the neutralized quencher) are incubated with the red blood cell composition for a suitable time interval prior to addition of the pathogen inactivating compound, such as for about 30 minutes to 48 hours, also about 2 to 24 hours, also about 8 to 24 hours. In some further embodiments, the incubation is in a temperature range of about 1° C. to 30° C., also about 18° C. to 25° C., or about room temperature.

In some embodiments of each of the methods described herein, the pathogen inactivating compound is incubated with the red blood cell composition in the presence of the quencher and the added base (or the neutralized quencher) for a suitable time interval, such as for about 30 minutes to 48 hours, also about 2 to 24 hours, also about 8 to 24 hours. In some further embodiments, the incubation is in a temperature range of about 1° C. to 30° C., also about 18° C. to 25° C., or about room temperature.

In addition to comparing the log inactivation as discussed above, the efficacy of the improved quenching methods may be evaluated by several other methods. The quenching methods may be assessed by evaluating the modification of the red blood cell composition, both in terms of the function of the red blood cells, and in terms of the reactivity of the treated red blood cells with the immune system, such as with antibodies. If the treated red blood cell composition is intended for human use, such as infusion, the quenching methods should not substantially damage red blood cell function. The lack of a substantially damaging effect on red blood cell function may be measured by methods known in the art for testing red blood cell function. For example, the levels of indicators such as intracellular ATP (adenosine 5'-triphosphate), intracellular 2,3-DPG (2,3-diphosphoglycerol) or extracellular potassium may be measured, and compared to an untreated control. Additionally hemolysis, intracellular and extracellular pH, hematocrit, hemoglobin, osmotic fragility, glucose consumption and lactate production may be measured. The improved methods of the present invention can be compared to the standard condition of 2 mM acidic glutathione in combination with 0.2 mM PIC-1, as well as conditions with increasing glutathione, where the known methods utilize acidic glutathione, as described in U.S. Pat. No. 6,709,810. While increasing the glutathione concentration in the methods of the invention may result in a slight reduction in the level of inactivation of some pathogens, adequate levels of inactivation are still obtained, and the improved reduction in the modification of the red blood cells, while maintaining adequate function of the red blood cells, results in an overall better product.

Methods for determining ATP, 2,3-DPG, glucose, hemoglobin, hemolysis, and potassium are available in the art. See for example, Davey et al., *Transfusion*, 32:525-528 (1992), the disclosure of which is incorporated herein. Methods for determining red blood cell function are also described in Greenwalt et al., *Vox Sang*, 58:94-99 (1990); Hogman et al., *Vox Sang*, 65:271-278 (1993); and Beutler et al., *Blood, Vol.* 59 (1982) the disclosures of which are incorporated herein by reference. For example, intracellular ATP and intracellular 2,3-DPG are measured using a Sigma ATP kit or 2,3-DPG kit (Sigma, St. Louis, Mo.). The ATP kit is used following Sigma procedure No. 366-UV, the disclosure of which is hereby incorporated by reference. Extracellular potassium levels may be measured using a Ciba Corning Model 614 $K^+/Na^+$ Analyzer (Ciba Corning Diagnostics Corp., Medford, Ma.). The extracellular pH is measured by centrifuging the cells at 4° C. for 15 minutes at 12,000×g and removing the supernatant, for which the pH is measured using a standard pH meter at room temperature (e.g. Beckman, Epoxy Calomel electrode). For the intracellular pH, the remaining pellet is capped in the centrifuge tube and stored at about −80° C. for at least 2 hours. This is then lysed by the addition of deionized water. The lysed sample is mixed well and the pH of the solution is measured either at room temperature using a standard pH meter or at room temperature using a Ciba Corning Model 238 Blood Gas Analyzer (Ciba Corning Diagnostics Corp., Medford, Ma.). Measurements can be made shortly after treatment and as a function of post treatment storage, for example storage for up to 42 days. The methods of the present invention provide a red blood cell composition wherein hemolysis of the treated red blood cells is less than 3% after 28 day storage, more preferably less than 2% after 42 day storage, and most preferably less than or equal to about 1% after 42 day storage at 4° C. Preferred methods provide a red blood cell composition wherein the intracellular ATP level is higher than that of a similar composition treated with the standard condition of 2 mM acidic glutathione and 0.2 mM PIC-1. In some embodiments, the quenching methods of the present invention provide ATP levels that are about 20%, also 30%, also 40% or about 50% higher than a composition treated with 2 mM acidic glutathione and 0.2 mM PIC-1, wherein the higher level of ATP is maintained after 7, 14, 21, 28, 35, or 42 days of storage.

The reduction in modification of red blood cells in the methods of the present invention can be evaluated by several assays. In one assay, rabbit polyclonal sera that is reactive with acridine is produced by injecting New Zealand White rabbits with an acridine compound conjugated to KLH. The acridine compound S-197 was used and has the following structure:

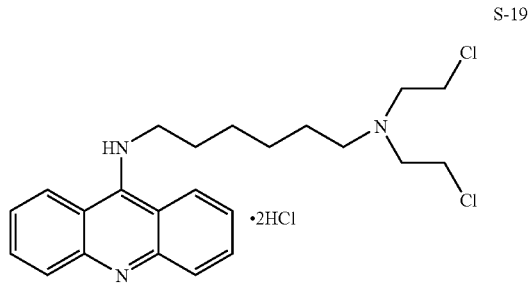

S-197

This is conjugated to KLH by adding 10 µL of the compound (10 mM in de-ionized water) to 990 µL of a buffered solution of KLH (10 mg/mL in 50 mM Phosphate, 150 mM NaCl, PBS pH=7.2 with proprietary stabilizer, Pierce Cat # 77600) and incubating at room temperature for over 20 hours. Following this incubaton, the conjugated KLH is isolated from the unreacted S-197 and S-197 by-products by passing through a desalting column (e.g. D-salt columns, Pierce) and eluting in PBS buffer. The colored fractions of the solutions are then combined and the KLH conjugates are characterized by the ratio of absorbance at 210 and 410 nm. The acridine-KLH conjugate solutions are mixed with Complete Freund's Adjuvant for intramuscular injection into the rabbits at multiple sites to immunize the rabbits. The resulting rabbit sera will have a high titer of polyclonal antibody that is reactive with the acridine structure. The rabbit sera can be incubated with red blood cell compositions that have been treated with, for example, PIC-1 and glutathione. The unbound rabbit antibody is washed out and the solution is reacted with a goat anti-rabbit antibody. The resulting solution can be assayed for agglutination by passing through a Buffer Gel Card (Micro Typing Systems, Pompano Beach, Fla.). The gel cards are designed to allow non-agglutinated red blood cells to pass through, while cells agglutinated by reaction with the rabbit sera and cross reacting with the anti-rabbit antibody will remain at the top of the gel. The cards are scored as 0, 1+, 2+, 3+, or 4+, where 0 indicates all cells are intact and are at the bottom of the gel, while 4+ indicates complete agglutination, with all cells at the top of the gel. The quenching methods of the present invention will result in a score of 1+ or lower, preferably 0, when assayed using a 1:100 dilution of the rabbit sera, whereas a similar composition treated with 2 mM acidic glutathione and 0.2 mM PIC-1 results in scores of 2+ or higher.

Further, the quenching methods of the present invention will result in lower scores when compared to a similar composition treated with acidic glutathione at the same concentration of quencher as the preferred quenching method and the same concentration of pathogen inactivating compound. For example, a red blood cell composition treated with 10 mM neutralized glutathione and 0.2 mM PIC-1 will result in a lower score, preferably a score of 1+ or 0, than a red blood cell composition treated with 10 mM acidic glutathione and 0.2 mM PIC-1.

In another assay, the rabbit polyclonal sera may be reacted with treated red blood cells. After washing off unbound antibody, a FITC labeled goat anti-rabbit Fab'$_2$ fragment (anti H+L chains, Caltag) is added. The binding of FITC label to the red blood cells correlates with the amount of acridine bound to the red blood cell surface, and is assessed by FACScan™ analysis (Becton, Dickinson and Co., NJ). The relative modification of the red blood cells is determined from the FACScan™ mean fluorescence value. The quenching methods of the present invention, when compared with treatment using 2 mM acidic glutathione and 0.2 mM PIC-1, will result in reduction of the mean fluorescence by at least 50%, also at least 75%, or at least 90%. Further, the quenching methods of the present invention will result in a lower level of mean fluorescence when compared to a similar composition treated with acidic glutathione at the same concentration of quencher as the preferred quenching method and the same concentration of pathogen inactivating compound. For example, a red blood cell composition treated with 10 mM neutralized glutathione and 0.2 mM PIC-1 will result in a lower level of mean fluorescence than a red blood cell composition treated with 10 mM acidic glutathione and 0.2 mM PIC-1. The quenching methods of the present invention, when compared with such similar treatment with acidic glutathione, will result in reduction of the mean fluorescence by at least 10%, also at least 25%, also at least 50%, also at least 75%, or at least 90% as compared to the acidic glutathione treatment.

Finally, serum samples from patients infused with red blood cells that have been treated with 2 mM glutathione and 0.2 mM PIC-1 that appear to have developed anti-PIC-1 antibody can be used to assess cross reactivity with treated red blood cell compositions of the present invention. This assay is similar to the Gel Card assay using rabbit polyclonal sera. In this assay, the gel contains rabbit anti-human IgG, such that red blood cells reactive with the patient sera will agglutinate at the top of the gel. The cards are scored as indicated above. The quenching methods of the present invention will result in scores of 1+ or lower, preferably 0, for this assay, whereas a similar composition treated with 2 mM acidic glutathione and 0.2 mM PIC-1 results in scores of 2+ or higher. Further, the quenching methods of the present invention will result in lower scores when compared to a similar composition treated with acidic glutathione at the same concentration of quencher as the preferred quenching method and the same concentration of pathogen inactivating compound. For example, a red blood cell composition treated with 10 mM neutralized glutathione and 0.2 mM PIC-1 will result in a lower score, preferably a score of 1+ or 0, than a red blood cell composition treated with 10 mM acidic glutathione and 0.2 mM PIC-1.

The quenching methods of the invention can also be compared to existing methods by determining the level of modification of nucleic acids in a sample. Typically, a red blood cell composition may contain leukocytes, and the nucleic acid from the leukocytes can be isolated. A pathogen inactivating compound having a radioactive isotope that, upon reaction of the compound with nucleic acid, will remain bound to the nucleic acid. This can be used to assess the amount of compound reacted with the nucleic acid for a variety of quenching methods, and provides a measure that can be directly correlated to expected leukocyte inactivation. The number of adducts formed per 1,000 nucleic acid base pairs can be used as a model to assess the expected impact of the various methods on pathogen inactivation. Alternatively, a suitable amount of a pathogen can be added to a red blood cell composition and the nucleic acid of the pathogen can be isolated after treatment. However, in this case the sample needs to be leukoreduced such that the levels of any residual leukocytes will not interfere with the measurement of pathogen nucleic acid.

In addition to providing adequate pathogen inactivation while reducing the levels of unwanted side reactions, the quenching methods of the present invention also provide, in at least some embodiments, a reduction in the concentration of reactive electrophilic species after pathogen inactivation. If the red blood cell compositions are intended for infusion, it is important that the level of reactive electrophilic species is as low as possible, preferably essentially no longer detectable. The presence of the reactive electrophilic species may be determined using methods available in the art, such as chromatographic methods including liquid chromatography-mass spectroscopy (LC-MS). In addition, the residual activity of a sample may be assessed by evaluating its ability to react with a guanine residue of a nucleic acid, such as using the general alkylator assay described by Matties (Matties, W R, Anal. Biochem. October 1992; 206(1):161-7). In this assay, the RBC are extracted after a suitable incubation time with the pathogen inactivating compound and quencher. Any residual pathogen inactivating compound, as well as the quencher and other small species, are separated from the proteins. These species are then incubated with ds DNA synthesized with 8-$^3$H guanine residues. The residual pathogen inactivating compound reacts with ds DNA at the N7 position of guanine, which acidifies the 8-H reside and releases the $^3$H into solution, where it can be isolated and measured. The amount of tritium released can be quantified, and has a 1:1 correlation with the amount of residual alkylator present in the extracted samples tested. The level of electrophilic species as determined by these methods can be assessed using the improved methods of the invention and comparing to known methods.

In some embodiments of each of the methods described herein, the method further comprises the step of reducing the concentration of a compound in the mixture, wherein the compound is selected from the group consisting of the pathogen inactivating compound or a degradation product of the pathogen inactivating compound. In some embodiments, the method comprises the step of reducing the concentration of the pathogen-inactivating compound in the mixture. In some embodiments, the method comprises the step of reducing the concentration of the electrophilic species in the mixture. In some embodiments, the method comprises the step of reducing the concentration of the quencher in the mixture. The concentration of the pathogen inactivating compound and/or the quencher (and related products) in a biological material, such as a blood product, can be reduced after the treatment, for example by adsorption in a batch or flow removal process. Methods and devices which may be used are described in U.S. Pat. Nos. 6,544,727 and 6,331,387 and U.S. Patent Publication Nos. 2002/0192632, 2005/0142542, 2004/0185544, and 2001/0009756, the disclosures of each of which are incorporated herein by reference in their entirety. Accordingly, in some embodiments, the concentration of the pathogen-inactivating compound is reduced by contacting the mixture with an adsorption medium comprising adsorbent particles having an affinity for the pathogen-inactivating compound. In some embodiments, the adsorption system would be configured to remove the pathogen-inactivating compound in a batch process. In some embodiments, the concentration of the pathogen-inactivating compound in the mixture is reduced by washing the red blood cells.

The methods of the invention result in adequate inactivation of possible pathogen contaminants in red blood cell compositions with improved quenching as compared to known methods. In preferred methods, as discussed above, the pathogen inactivating compound comprises a nucleic acid targeting portion and a reactive electrophilic group and the quencher comprises cysteine, wherein the quencher provides for a suitable pH when added to the red blood cell composition. In some embodiments, the quencher is acidic and is neutralized with 1 to 2 equivalents of a suitable base, such as sodium hydroxide. In a preferred embodiment, the quencher is glutathione neutralized with 2 equivalents of base. In a preferred embodiment, the pathogen inactivating compound comprises an acridine group linked to a mustard group via an ester bond. In a preferred embodiment, the pathogen inactivating compound is β-alanine, N-(acridin-9-yl), 2-[bis(2-chloroethyl)amino]ethyl ester, and salts thereof and the quencher is glutathione neutralized with 2 equivalents of base. The quencher may be added to the red blood cell composition before, after, or simultaneously with the pathogen inactivating compound. In some embodiments, the quencher is added in the time range of about 30 minutes prior to pathogen inactivating compound up to about 10 minutes following pathogen inactivating compound. In some embodiments, the quencher and pathogen inactivating compound may be added essentially simultaneously but separately. For example, in the preferred embodiment where the pathogen inactivating compound is β-alanine, N-(acridin-9-yl), 2-[bis(2-chloroethyl)

amino]ethyl ester and the quencher is neutralized glutathione, these can not easily be formulated in solution together for addition to the red blood cell composition. Because of the high concentration of glutathione required for adequate quenching, the pathogen inactivating compound precipitates when these are in the same solution in high concentrations. Once added to the red blood cell composition, they are sufficiently diluted and buffered as to both be completely soluble.

In a preferred embodiment of the invention, a red blood cell composition is mixed with β-alanine, N-(acridin-9-yl), 2-[bis(2-chloroethyl)amino]ethyl ester and glutathione neutralized with 2 equivalents of base. In a further embodiment, the neutralized glutathione is mixed with the red blood cell composition and the β-alanine, N-(acridin-9-yl), 2-[bis(2-chloroethyl)amino]ethyl ester is subsequently added within about 30 minutes of the glutathione, preferably within about 10 minutes. In another embodiment, the β-alanine, N-(acridin-9-yl), 2-[bis(2-chloroethyl)amino]ethyl ester and neutralized glutathione are mixed with the red blood cell composition essentially simultaneously, or within about 1 minute of each other. In another embodiment, the β-alanine, N-(acridin-9-yl), 2-[bis(2-chloroethyl)amino]ethyl ester is added to the red blood cell composition first, with the neutralized glutathione added within about 30 minutes, also within about 10 minutes, also within about 5 minutes, also within about 1 minutes. In some embodiments, upon mixing of all three of the components, e.g. within about 1 to 5 minutes of mixing, the glutathione is at a concentration in the range of about 5 mM to 30 mM, preferably about 10 mM to 30 mM, preferably about 20 mM, and the β-alanine, N-(acridin-9-yl), 2-[bis(2-chloroethyl)amino]ethyl ester is at a concentration in the range of about 0.05 mM to 0.5 mM, preferably about 0.1 mM to 0.3 mM, preferably about 0.2 mM, and the pH of the mixture is in the range of about 7.2 to 8.0.

The present invention also provides the red blood cell compositions resulting from each of the treatment methods described herein.

In some embodiments of each of the methods and compositions described herein, the red blood cells in the red blood cell composition are mammalian blood cells. For instance, the red blood cells may be rodent (e.g., mouse or rat or rabbit), ape (e.g., chimpanzee), or human red blood cells. For example, in some embodiments, the red blood cells are human. In some embodiments, the red blood cells have been leukoreduced. In some other embodiments, the red blood cells have not been leukoreduced. In some embodiments, there is a possibility that the composition comprising red blood cells is contaminated with a pathogen. In some embodiments, the red blood cell composition is contaminated with a pathogen.

In addition to the improved methods of quenching, the present invention provides disposable kits for the processing of a red blood cell composition, where the processing may be done manually or automatically. In some embodiments, the present invention provides kits comprising the pathogen-inactivating compound, quencher, and/or base used in the each of the methods described herein.

In some embodiments, the kit comprises β-alanine, N-(acridin-9-yl), 2-[bis(2-chloroethyl)amino]ethyl ester, including any salts thereof and neutralized glutathione, including any salts thereof. The β-alanine, N-(acridin-9-yl), 2-[bis(2-chloroethyl)amino]ethyl ester may be in solid form or in solution. Similarly, the neutralized glutathione may be in solid form or in solution. These solids or solutions may further comprise acceptable excipients, adjuvants, diluents, or stabilizers. In some embodiments, the β-alanine, N-(acridin-9-yl), 2-[bis(2-chloroethyl)amino]ethyl ester is the hydrochloride salt and the neutralized glutathione is neutralized with about 2 equivalents of sodium hydroxide. In some embodiments, the β-alanine, N-(acridin-9-yl), 2-[bis(2-chloroethyl)amino]ethyl ester and neutralized glutathione are in solid form and the kit further comprises a suitable solution for dissolving the β-alanine, N-(acridin-9-yl), 2-[bis(2-chloroethyl)amino]ethyl ester and a suitable solution for dissolving the neutralized glutathione. In some embodiments, the invention provides a kit comprising a pathogen inactivating compound, a quencher and a solution for dissolving the quencher, wherein the solution neutralizes the quencher. The methods and kits discussed herein encompass any suitable pharmaceutical formulation of the pathogen inactivating compound and quencher, which can be formulated as a mixture or separately. Pharmaceutically acceptable formulations are known to those skilled in the art, and examples of suitable excipients, adjuvants, diluents or stabilizers can be found, for example, in Gennaro, ed., Remington's The Science and Practice of Pharmacy, 20$^{th}$ edition, Lippincott Williams & Wilkins. The invention also includes the resulting compositions of the methods described above, comprising red blood cells, a pathogen inactivating compound and quencher as described above, wherein the composition is in a suitable pH range to effect improved quenching of the pathogen inactivating compound.

In another aspect, the invention provides a kit useful, e.g., for treating red blood cell compositions to inactivate pathogens, comprising a pathogen-inactivating compound comprising anucleic acid binding ligand and a functional group which is, or which forms, an electrophilic group (including any salt thereof) a quencher comprising a thiol group (including any salt thereof), and at least about 1 equivalent base, wherein an equivalent means a molar amount that is equivalent to the molar amount of quencher in the kit. In some embodiments, the kit comprises about 1 or about 2 equivalents of a suitable base.

In still another aspect, the invention provides a kit for treating red blood cell compositions to inactivate pathogens, comprising a nucleic acid binding ligand and a functional group which is, or which forms, an electrophilic group (e.g., PIC-1), including any salt thereof, and a neutralized quencher comprising a thiol group (e.g., neutralized glutathione), including any salt thereof.

The invention is further illustrated by the following non-limiting examples. In these examples, all bacteria and viruses were obtained from American Type Cell Culture (ATCC), Rockville, Md., or are clinical isolates.

EXAMPLE 1

Comparison of Inactivation of *Serratia marcescens*, *Staphylococcus epidermidis* and *Yersinia enterocolitica* to Standard Conditions The bacteria *S. marcescens* was grown overnight by addition of a single colony from a master plate to 500 mL of LB media at 37° C. The overnight culture was diluted 1:1000 in fresh media. The growth at 37° C. was monitored by the OD of the suspension at 600 nm. The preparation was used when the suspension reached 0.5 OD. Whole blood (Blood Source, Sacramento, Calif.) was used to prepare a red blood cell (RBC) composition by centrifuging to provide packed RBC (34 mL of approximately 90% hematocrit), then adding 17 mL Erythrosol to a hematocrit of approximately 60%. Erythrosol is a red blood cell additive (Baxter Healthcare Corp., Deerfield, Ill.) that may be prepared by combining sodium citrate dihydrate (7.82 g); sodium acid phosphate dihydrate (0.73 g); sodium phosphate dihydrate (3.03 g); adenine (0.22 g); mannitol (7.74 g); and glucose (9 g) in 1 liter of distilled water. The bacterial preparation was then added (1/100$^{th}$ of the total volume) to the RBC/Erythrosol to provide contaminated RBC. The contaminated RBC was divided into several samples and treated according to Table 2, where PIC-1 is β-alanine, N-(acridin-9-yl), 2-[bis(2-chloroethyl)amino] ethyl ester. The PIC-1 and glutathione (Aldrich, St. Louis, Mo.) were dissolved in a solution of 8% dextrose monohydrate at about 15× the desired concentration in the final red blood cell composition when added together, or 30× when added separately. Also, the glutathione was neutralized with the indicated equivalents of sodium hydroxide, prepared by adding an appropriate amount of 5 N Na OH to the glutathione. For each sample 4.67 mL of RBC was mixed with either 330 μL of PIC-1/glutathione or 165 μL of each PIC-1 and glutathione separately. For example, a standard treatment of 2 mM glutathione and 0.2 mM PIC-1 was prepared by dissolving 7.6 mg of PIC-1 and 46 mg of glutathione in 5 mL of 8% dextrose and adding 330 μL of this to 4.67 mL of RBC. A sample at 20 mM neutralized glutathione and 0.2 mM PIC-1 was prepared by dissolving 7.6 mg of PIC-1 and 460 mg of glutathione in 4.4 mL of 8% dextrose and mixing with 0.6 mL of 5N NaOH, then adding 330 μL of this to 4.67 mL of RBC. For separate addition using 20 mM neutralized glutathione, PIC-1 is prepared by dissolving 7.6 mg in 2.5 mL of 8% dextrose, glutathione is prepared by dissolving 460 mg in 1.9 mL of 8% dextrose and mixing with 0.6 mL of 5N NaOH, then adding 165 μL of each solution to 4.67 mL RBC in the appropriate order. Volumes of the various components are adjusted accordingly to provide the appropriate samples indicated in the tables. Following treatment, the samples were incubated for 2 hours, and 100 μL of each was serially diluted and plated on LB plates. These were incubated overnight at 37° C. in order to assess bacterial growth. The bacterial titer was determined by counting colonies on the plates and based on the dilution of the plate, the titer was determined. For example, with 10-fold serial dilutions, 30 colonies counted on the 5$^{th}$ dilution of the original solution, where 0.1 mL are plated, would indicate an initial titer of $(30 \times 10^5)/0.1 = 3 \times 10^7$, or 7.47 log. An untreated control sample (i.e. no PIC-1 or glutathione added) is used as the baseline to assess the log reduction in titer after treatment. Table 2A and 2B indicate both the log titer and log reduction for the various samples. Note that for most samples in Table 2A the PIC-1 and glutathione were formulated together. For samples 4-6, where the glutathione was neutralized with varying amounts of sodium hydroxide, the PIC-1 precipitated out of solution, with increasing precipitate as the amount of added base increased. As such, these results do not provide a good indication of the level of inactivation as the actual concentration of PIC-1 in solution is not known. The study was repeated with sequential addition of the two components, as indicated in Table 2B (time delay of 0 indicates they were added in the same solution). For comparison to the standard condition in Table 2A (samples 1 and 10), only sample 7, where the components were added separately, provides a reasonable comparison. In this case, also shown in Table 2B, quenching with 20 mM glutathione neutralized with 2 equivalents of base results in less log reduction by about 1-1.5 log compared to the standard condition (2 mM acidic glutathione and 0.2 mM PIC-1).

Additional studies were done using *S. epidermidis*, where the overnight culture was used without dilution. In these studies, the PIC-1 and glutathione were added in the sequence indicated in the Table 3, with results shown in the table. The inactivation of *S. epidermidis* is not significantly reduced when 20 mM neutralized glutathione is used as quencher. PIC-1 is at 0.2 mM in all samples.

A similar study was done using *Y. enterocolitica*, where, in addition to neutralized glutathione, neutralized cysteine was used as quencher, where the cysteine (Aldrich) was neutralized with either 1 or 2 equivalents of sodium hydroxide. In this study, 2 mM acidic glutathione is compared to 20 mM neutralized glutathione, or 20 mM neutralized cysteine, with 0.2 mM PIC-1 in all samples. The results are indicated in Table 4. The results indicate that appropriately neutralized cysteine is as effective as neutralized glutathione, with a reduction of about 2.5 log inactivation relative to the standard condition.

TABLE 2A

Inactivation of Serratia marcescens in RBC under various quenching conditions.

| Sample | mM of PIC-1 | Glutathione mM | Eq. base added | Log titer | S. marcescens reduction |
|---|---|---|---|---|---|
| Control | 0 | 0 | 0 | 7.0 | NA |
| 1 | 0.2 | 2 | 0 | 2.9 | 4.14 |
| 2 | 0.2 | 2 | 0.9 | 2.8 | 4.27 |
| 3 | 0.2 | 20 | 0 | 4.6 | 2.40 |
| 4 | 0.2 | 20 | 0.9 | 4.8 | 2.26 |
| 5 | 0.2 | 20 | 1.5 | 5.4 | 1.66 |
| 6 | 0.2 | 20 | 2 | 6.3 | 0.76 |
| 7 (sequential)* | 0.2 | 20 | 2 | 4.0 | 3.02 |
| 8 | 0 | 20 | 0 | 7.0 | 0.02 |
| 9 | 0 | 20 | 2 | 7.4 | 0.31 |
| 10 | 0.2 | 2 | 0 | 2.5 | 4.50 |

*For this sample, PIC-1 was added first, with glutathione added shortly after. For all other samples, the PIC-1 and glutathione were formulated together and added to the RBC.

TABLE 2B

Inactivation of Serratia marcescens in RBC including sequential addition of PIC-1 and glutathione.
(PIC-1 is at 0.2 mM in all samples.)

| Sample | Sequence of addition | Glutathione mM | Eq. base | Time delay (minutes) | Log S. marcescens titer | reduction |
|---|---|---|---|---|---|---|
| control | NA | 0 | 0 | 0 | 6.76 | NA |
| 1 | PIC-1/glutathione | 20 | 2 | 1 | 3.40 | 3.36 |
| 2 | PIC-1/glutathione | 20 | 2 | 5 | 2.87 | 3.89 |
| 3 | PIC-1/glutathione | 20 | 2 | 10 | 1.80 | 4.96 |
| 4 | PIC-1/glutathione | 20 | 2 | 20 | 0.00 | 6.76 |
| 5 | Glutathione/PIC-1 | 20 | 2 | 1 | 3.10 | 3.66 |
| 6 | Glutathione/PIC-1 | 20 | 2 | 10 | 3.08 | 3.68 |
| 7 | simultaneous | 2 | 0 | 0 | 1.51 | 5.25 |
| 8 | simultaneous | 20 | 0 | 0 | 6.05 | 0.71 |

TABLE 3

Inactivation of *Staphylococcus epidermidis* in RBC including sequential addition of PIC-1 and glutathione. (PIC-1 is at 0.2 mM in all samples.)

| Sample | Sequence of addition | Glutathione mM | Eq. base | Time delay (minutes) | *S. epidermidis* titer | Log reduction |
|---|---|---|---|---|---|---|
| control | NA | 0 | 0 | 0 | 6.62 | NA |
| 1 | PIC-1/glutathione | 20 | 2 | 1 | −0.08 | 6.70 |
| 2 | PIC-1/glutathione | 20 | 2 | 5 | −0.08 | 6.70 |
| 3 | PIC-1/glutathione | 20 | 2 | 10 | −0.08 | 6.70 |
| 4 | PIC-1/glutathione | 20 | 2 | 20 | −0.08 | 6.70 |
| 5 | Glutathione/PIC-1 | 20 | 2 | 1 | 0.52 | 6.10 |
| 6 | Glutathione/PIC-1 | 20 | 2 | 10 | 0.70 | 5.92 |
| 7 | simultaneous | 2 | 0 | 0 | −0.08 | 6.70 |
| 8 | simultaneous | 20 | 0 | 0 | 6.40 | 0.22 |

TABLE 4

Inactivation of *Yersinia enterocolitica* in RBC including sequential addition of PIC-1 and glutathione. (PIC-1 is at 0.2 mM in all samples.)

| Sample | Sequence of addition | Quencher mM | Eq. base | Time delay (minutes) | *Y. enterocolitica* titer | Log reduction |
|---|---|---|---|---|---|---|
| control | NA | 0 | 0 | 0 | 8.49 | NA |
| 1 | NA | 2 | 0 | 0 | 0.00 | 8.49 |
| 2 | Glutathione/PIC-1 | 20 | 2 | 10 | 2.54 | 5.95 |
| 3 | Cysteine/PIC-1 | 20 | 1 | 10 | 4.45 | 4.04 |
| 4 | Cysteine/PIC-1 | 20 | 2 | 10 | 2.70 | 5.79 |

TABLE 5A

Inactivation of *Serratia marcescens* in RBC with PIC-1 and glutathione or cysteine or a combination of the two. (PIC-1 is at 0.2 mM in all samples.)

| Sample | Sequence of addition | Quencher mM | Eq. base | Time delay (minutes) | *S. marcescens* titer | Log reduction |
|---|---|---|---|---|---|---|
| RBC | untreated | NA | NA | NA | 7.5 | NA |
| 1 | PIC-1/GSH | 20 | 2 | 1 | 4.8 | 2.7 |
| 2 | GSH/PIC-1 | 20 | 2 | 10 | 4.1 | 3.4 |
| 3 | Cys/PIC-1 | 20 | 2 | 10 | 4.4 | 3.1 |
| 5 | Cys, GSH/PIC-1 | 10, 10 | 2, 2 | 10 | 4.5 | 3.0 |
| 6 | Cys, GSH/PIC-1 | 15, 5 | 2, 2 | 10 | 3.8 | 3.7 |

TABLE 5B

Inactivation of *Serratia marcescens* in RBC with PIC-1 and glutathione or cysteine. (PIC-1 is at 0.2 mM in all samples.)

| Sample | Sequence of addition | Quencher mM | Eq. base | Time delay (minutes) | *S. marcescens* titer | Log reduction |
|---|---|---|---|---|---|---|
| RBC | untreated | NA | NA | NA | 7.6 | NA |
| 1 | PIC-1 + GSH | 2 | 0 | 0 | 3.5 | 4.1 |
| 2 | GSH/PIC-1 | 20 | 2 | 10 | 4.4 | 3.2 |
| 3 | Cys/PIC-1 | 2.5 | 2 | 10 | 3.9 | 3.7 |
| 4 | Cys/PIC-1 | 5 | 2 | 5 | 4.4 | 3.2 |
| 5 | Cys/PIC-1 | 5 | 2 | 10 | 4.4 | 3.2 |
| 6 | Cys/PIC-1 | 5 | 2 | 20 | 4.7 | 2.9 |
| 7 | Cys/PIC-1 | 10 | 2 | 10 | 4.9 | 2.7 |
| 8 | Cys/PIC-1 | 15 | 2 | 10 | 4.5 | 3.1 |
| 9 | Cys/PIC-1 | 20 | 2 | 5 | 4.4 | 3.2 |
| 10 | Cys/PIC-1 | 20 | 2 | 10 | 4.6 | 3.0 |
| 11 | Cys only | 20 | 2 | NA | 7.3 | 0.3 |

TABLE 5C

Inactivation of *Staphylococcus epidermidis* in RBC with PIC-1 and glutathione or cysteine. (PIC-1 is at 0.2 mM in all samples.)

| Sample | Sequence of addition | Quencher mM | Eq. base | Time delay (minutes) | *S. epidermidis* titer | Log reduction |
|---|---|---|---|---|---|---|
| RBC | untreated | NA | NA | NA | 7.2 | NA |
| 1 | PIC-1 + GSH | 2 | 0 | 0 | 0 | 7.2 |
| 2 | GSH/PIC-1 | 20 | 2 | 10 | 0 | 7.2 |
| 4 | Cys/PIC-1 | 2.5 | 1 | 10 | 0 | 7.2 |
| 5 | Cys/PIC-1 | 5 | 1 | 10 | 0 | 7.2 |
| 6 | Cys/PIC-1 | 10 | 1 | 10 | 2.3 | 4.9 |
| 3 | Cys/PIC-1 | 20 | 1 | 10 | 3.2 | 4.0 |
| 7 | Cysteine only | 20 | 1 | NA | 7.1 | 0.1 |

Additional studies were done using cysteine as the quencher. Samples were prepared and assessed as described above, with cysteine (Cys) neutralized with either 1 or 2 equivalents of sodium hydroxide. For these samples, the NaOH stock was prepared at 10N and appropriate volumes of the various components were used following the procedures above. Standard conditions and/or 20 mM neutralized glutathione (GSH) were run for comparison. In the study shown in Table 5A, a combination of cysteine and glutathione was also used. The results are shown in Tables 5A, 5B, and 5C showing at least about 3 log inactivation under all conditions. Generally, cysteine and glutathione result in similar reduction in pathogen inactivation relative to the standard condition, where inactivation is within about 1-1.5 log of the standard condition. The combination of the two is of interest in that cysteine is able to go into the cells while glutathione does not enter the cells in any substantial amount. This shows that under appropriate conditions of quenching both inside and outside of the cells, similar inactivation results are observed.

EXAMPLE 2

Comparison of Inactivation of Vesicular Stomatitis Virus (VSV) to Standard Conditions A 100× stock of VSV (approximately $1.78 \times 10^8$ titer) is used to contaminate a red blood cell composition prepared as per Example 1. The contaminated RBC were treated as indicated in Table 5A-B, incubating for 2 hours. The components were added as shown for similar experiments described above. A volume of 5 mL contaminated RBC was treated for each sample. The RBC were frozen in liquid $N_2$ after the end of the incubation and analyzed at a later time. The titer of VSV remaining was determined by plaque assay in African Green Monkey cells Vero 76, grown in EMEM supplemented with 10% fetal calf serum and other essential elements. The titer was calculated by determination of the number of plaques obtained upon application of diluted samples on confluent preparations of cells as previously published (Hsiung G D and Melnick J L, Journal of Immunology 78, 128-136. 1957) The results are shown in Table 6A, indicating that the quenching methods all provide essentially complete inactivation of a high titer of VSV. An additional study was done using cysteine as the quencher, with or without neutralization with 2 equivalents of sodium hydroxide. The results are shown in Table 6B, with standard condition and 20 mM neutralized glutathione for comparison. The cysteine at 20 mM, either acidic or neutralized, reduces the level of inactivation by about 2-3 log, with the neutralized sample showing the lowest level of inactivation. The glutathione sample at 20 mM also reduced the level of inactivation, by about 2 log. All of the results indicate that inactivation of the extracellular virus VSV is not very sensitive to quenching conditions.

TABLE 6A

Inactivation of VSV in RBC including sequential addition of PIC-1 and glutathione. (PIC-1 is at 0.2 mM in all samples.)

| Sample | Sequence of addition | Glutathione Eq. mM | base | Time delay (minutes) | Log VSV titer | reduction |
|---|---|---|---|---|---|---|
| RBC | untreated | 0 | 0 | NA | 7.58 | NA |
| 1 | PIC-1 + glutathione | 2 | 0 | 0 | <-0.11 | >6.32 |
| 2 | PIC-1 + glutathione | 20 | 2 | 0 | 5.68 | 0.54* |
| 3 | PIC-1 + glutathione | 20 | 0 | 0 | <-0.11 | >6.32 |
| 4 | PIC-1/glutathione | 20 | 0 | 1 | <-0.11 | >6.32 |
| 5 | PIC-1/glutathione | 20 | 2 | 1 | -0.11 | 6.32 |
| 6 | PIC-1/glutathione | 20 | 2 | 5 | <-0.11 | >6.32 |
| 7 | PIC-1/glutathione | 20 | 2 | 10 | <-0.11 | >6.32 |
| 8 | Glutathione/PIC-1 | 20 | 2 | 10 | <-0.11 | >6.32 |
| 9 | Glutathione/PIC-1 | 20 | 0 | 10 | <-0.11 | >6.32 |
| 10 | Glutathione only | 20 | 2 | NA | 6.25 | -0.04 |
| 11 | Untreated control | 0 | 0 | NA | 6.22 | NA |

*Co-addition with neutralized glutathione precipitates PIC-1 from solution.

TABLE 6B

Inactivation of VSV in RBC with PIC-1 and glutathione or cysteine. (PIC-1 is at 0.2 mM in all samples.)

| Sample | Sequence of addition | Glutathione Eq. mM | base | Time delay (minutes) | Log VSV titer | reduction |
|---|---|---|---|---|---|---|
| RBC | untreated | 0 | 0 | NA | 6.56 | NA |
| 1 | PIC-1 + glutathione | 2 | 0 | 0 | -0.3 | >6.86 |
| 2 | Glutathione/PIC-1 | 20 | 2 | 10 | 1.41 | 4.99 |
| 3 | Cysteine/PIC-1 | 2 | 2 | 10 | <-0.3 | >6.86 |
| 4 | Cysteine/PIC-1 | 2 | 0 | 10 | <-0.3 | >6.86 |
| 5 | Cysteine/PIC-1 | 5 | 2 | 5 | 0.7 | 5.86 |
| 6 | Cysteine/PIC-1 | 5 | 0 | 5 | <-0.3 | >6.86 |
| 7 | Cysteine/PIC-1 | 5 | 2 | 10 | <-0.3 | >6.86 |
| 8 | Cysteine/PIC-1 | 5 | 0 | 10 | <-0.3 | >6.86 |
| 9 | Cysteine/PIC-1 | 20 | 2 | 10 | 2.75 | 3.8 |
| 10 | Cysteine/PIC-1 | 20 | 0 | 10 | 1.95 | 4.61 |

EXAMPLE 3

Determination of PIC-1 Adduct Frequency on Human Leukocyte Genomic DNA after Treatment of RBC with PIC-1 and Glutathione or cysteine Whole blood which had not been leukoreduced was used to prepare RBC in Erythrosol as described in Example 1. Aliquots of 20 mL each were treated either with 0.2 mM PIC-1, 0.2 mM PIC-1 and 2 mM acidic glutathione, 20 mM neutralized glutathione (2 equivalents of base), with PIC-1 added to 0.2 mM 10 minutes later, or 20 mM each of neutralized glutathione (2 equivalents of NaOH) and neutralized cysteine (1 equivalent of NaOH), with PIC-1 added to 0.2 mM 10 minutes later. The PIC-1 used included radiolabeled PIC-1, where the reactive group included a $^{14}C$ label (ViTrax, Inc., Placentia, Calif.). The specific activity of the PIC-1 used was 1.08 µCi/pmole. All samples were incubated at room temperature for 20 hours. After the incubation, 20 mL of RBC were diluted with a 20 mL volume of PBS and 20 mL of the mixture were added to each of two tubes containing 10 mL of Ficoll. The suspension was then centrifuged at 400×g for 30 minutes. The white blood cell portion was separated and the centrifuge step repeated after adding another 20 mL of PBS. The pellets obtained were combined and the combined pellet was resuspended in 5 mL Lysis buffer (100 mM NaCl, 10 mM Tris HCl, 25 mM EDTA, 5% SDS, 0.1 mg/mL Proteinase K, Sigma, St. Louis, Mo.) and was incubated at 50° C. for at least two hours. The resulting solution was then extracted with 5 mL of phenol:chloroform:isoamyl alcohol 24:25:1, followed by 5 mL of chloroform, and then 5 mL of ether. The genomic DNA was isolated in the aqueous layer and precipitated by addition of 0.5 mL of 3 M NaOAc, 10 mL of 100% ethanol, followed by incubation of the final mixture in a dry ice/ethanol bath. The DNA was isolated by centrifugation at 6,000×g for 10'. The supernatant was removed, and the pellet air-dried and resuspended in 1 mL of TE buffer (100 mM Tris HCl, 1 mM EDTA, pH=7.4) The amount of DNA isolated was quantified by UV absorption at 260 nm and the amount of PIC-1 adducts was quantified by liquid scintillation counting (Perkin Elmer-Wallac, Winspectral 1414 Liquid Scintillation Counter, Shelton, Conn.) of the solution of DNA, using the specific activity of the PIC-1 to assess the molar ratio of PIC-1 to DNA base pairs. The number of adducts per 1000 bp (kbp) are shown in Table 7 below, indicating that the modification of leukocyte nucleic acid is comparable in the samples quenched with 20 mM neutralized glutathione compared to the standard condition or the unquenched sample. Glutathione is indicated as "GSH" and cysteine as "Cys" in the table, as well as elsewhere herein. The determination of adduct frequency was used as a surrogate measurement for the inactivation of leukocytes. It is known that under the standard pathogen inactivation conditions, leukocytes are inactivated to the level of detection of a limiting dilution assay, which corresponds to 5.3 log of inactivation. The mechanism of inactivation is through formation of adducts on the genomic nucleic acids. The results therefore indicate that the improved quenching methods should not impact the inactivation of leukocytes significantly. Similar studies could be done with a suitable pathogen using leukoreduced red blood cells in order to assess the binding to the pathogen nucleic acid under various conditions.

TABLE 7

PIC-1 Adduct frequency in genomic DNA after various treatment conditions.

| Sample | Quencher | CPM | Recovered DNA (ug) | Adducts per kbp | Adduct frequency* |
|---|---|---|---|---|---|
| 1 | None | 39321 | 487 | 28 | 36 |
| 2 | None | 46293 | 547.5 | 28 | 35 |
| 3 | 2 mM acidic GSH | 46181 | 502 | 34 | 29 |
| 4 | 2 mM acidic GSH | 47204 | 692.5 | 23 | 44 |
| 5 | 20 mM neut.** GSH | 89836 | 872 | 37 | 27 |
| 6 | 20 mM neut. GSH | 60829 | 527.5 | 36 | 28 |
| 7 | 20 mM each neut. GSH and Cys | 83392 | 952.5 | 30 | 33 |

*Average number of base pairs between adducts.
**neutralized with 2 equivalents

EXAMPLE 4

Effect of pH Adjustment of RBC on Quenching as Assessed by Anti-Acridine Antibody Binding to Red Blood Cells It is possible to adjust the pH of the RBC composition prior to the addition of glutathione, as is demonstrated in this example by washing the RBC using various solutions of different pH. A 20 mL sample of leukoreduced whole blood (Blood Source, Sacramento, Calif.) was centrifuged at 4,100×g for 5 minutes at room temperature in each of four 50 mL centrifuge tubes. The supernatant was removed from each tube to provide red cell concentrate (RCC). For sample 1, 5 mL of Erythrosol (pH 7.3) was added to 10 mL of the RCC. For samples 2-4, the RCC was washed three times with 10 mL of the indicated solution, centrifuging as above and removing the supernatant after each wash. For each washed RCC, cells were resuspended in 5 mL of the solution used for washing. This is now referred to as the RBC test sample. The solutions used in samples 2-4 were Erythrosol (pH 7.3), PBS pH 8 (50 mM phosphate, 100 mM NaCl, pH 8.0), and CHES pH 9 (50 mM CHES (Aldrich), 100 mM NaCl, pH 9.0), respectively. For each RBC test sample, 1.5 mL was mixed with 100 µL of PIC-1 plus glutathione (2 mM acidic or 20 mM neutralized with 0.9, 1.5 or 2 equivalents of sodium hydroxide) to give the final concentrations of 0.2 mM PIC-1 and 2 mM or 20 mM glutathione. These samples were incubated for 20 hours at room temperature. After incubation, the RBC were washed in BBS (Blood Bank Saline, 0.9% saline, unbuffered, Fisher Scientific) and were diluted to a final hematocrit of 4%. A 25 µL aliquot of each was mixed with 15 µL of rabbit polyclonal anti-acridine sera diluted 1:100 in BBS and the mixture was incubated at 37° C. for 30 minutes. The cells were subsequently washed with 1.5 mL BBS. After washing was complete, the cells were mixed with 50 µL of FITC labeled goat anti-rabbit Fab'$_2$ fragment (1:64 dilution in BBS) and incubated at 37° C. for 30 minutes. After incubation, the cells were washed again with 3×1.5 mL BBS. The red blood cells were then analyzed by FACScan, and the mean fluorescence observed for each sample is given in Table 8. This value correlates with binding of PIC-1 acridine to the red blood cell surface, such that a lower value indicates improved quenching of the side reaction of PIC-1 with RBC. The binding of PIC-1 to RBC was significantly reduced by just washing the cells in higher pH buffer, with the neutralized glutathione providing even better quenching. Note that the quenching improves as glutathione is neutralized with increasing amounts of sodium hydroxide. This example demonstrates the importance of adjusting the pH of the red blood cell composition to provide improved quenching. Washing with CHES pH 9 in combination with glutathione neutralized with 1.5 or 2 equivalents of sodium hydroxide reduces the binding of PIC-1 to almost background levels.

TABLE 8

Treatment of RBC with 0.2 mM PIC-1 under various quenching conditions, FACScan analysis of anti-acridine antibody binding.

| | | Mean fluorescence intensity | | | | |
|---|---|---|---|---|---|---|
| | | untreated | 2 mM | 20 mM GSH + NaOH | | |
| Sample | RBC prep | control | GSH | 0.9 eq. | 1.5 eq. | 2 eq. |
| 1 | Erythrosol (pH 7.3) no wash | 1.67 | 108 | 17.0 | 8.1 | 6.0 |
| 2 | Erythrosol (pH 7.3) 3x wash | 1.69 | 199 | 26.7 | 4.9 | 3.4 |
| 3 | PBS pH 8 3x wash | 1.70 | 25 | 7.2 | 5.1 | 5.1 |
| 4 | CHES pH 9 3x wash | 1.62 | 12.1 | 3.9 | 1.9 | 1.9 |

EXAMPLE 5

Comparison of Various Quenching Conditions with Respect to Binding of Anti-Acridine Antibody Binding to Red Blood Cells The FACScan analysis of the binding of rabbit anti-acridine sera to treated red cells was used to assess a variety of quenching conditions. RBC samples were prepared as described in Example 1, and quenchers were prepared as described in the examples above. The sequence of component addition and final compound concentrations upon mixing with the RBC are indicated in Tables 9A and 9B. The tables represent data from two different experiments, each with samples treated under standard conditions or with 20 mM neutralized glutathione. PIC-1 is at 0.2 mM in all samples. The data within an experiment provides the relative efficacy of the various treatments. Because the assay may depend on the lot of red blood cells used, the absolute values of mean fluorescence may vary from one study to the next, such that relative values should only be compared within a given experiment. For example, note that the standard condition results in a mean fluorescence of 114 in Table 9A and 151-182 in Table 9B. Neutralized cysteine effectively quenches to essentially background signal (i.e. essentially no binding) at 15 or 20 mM. Neutralized glutathione at 20 mM results in close to background levels. From Table 9B, the results for cysteine indicate that, while increasing quencher concentration provides better quenching of the reaction with RBC, as the cysteine concentration increases, neutralization of the cysteine provides the optimal quenching of the unwanted side reaction. Note that at 2.5 mM cysteine, there is little difference between neutralized and acidic cysteine, while at 5 mM or higher, 1 equivalent of NaOH further reduces the signal compared to the acidic cysteine sample at the same concentration.

TABLE 9A

Relative anti-acridine antibody binding to treated RBC measured as FACScan mean fluorescence. (PIC-1 is at 0.2 mM in all samples.)

| | | Quencher | | |
|---|---|---|---|---|
| Sample | Sequence of addition | mM | Eq. NaOH | Time delay (minutes) | Mean Fluorescence |
| 1 | PIC-1 + GSH | 2 | 0 | 0 | 114 |
| 2 | GSH/PIC-1 | 20 | 2 | 10 | 2.6 |
| 3 | Control Cys only | 20 | 2 | NA | 1.9 |
| 4 | Cys/PIC-1 | 2.5 | 2 | 10 | 37 |
| 5 | Cys/PIC-1 | 5 | 2 | 5 | 8 |
| 6 | Cys/PIC-1 | 5 | 2 | 10 | 10.8 |
| 7 | Cys/PIC-1 | 5 | 2 | 20 | 8 |
| 8 | Cys/PIC-1 | 10 | 2 | 10 | 2.9 |
| 9 | Cys/PIC-1 | 15 | 2 | 10 | 1.9 |
| 10 | Cys/PIC-1 | 20 | 2 | 5 | 1.9 |
| 11 | Cys/PIC-1 | 20 | 2 | 10 | 1.9 |
| 12 | Cys/PIC-1 | 20 | 2 | 20 | 2 |

TABLE 9B

Relative anti-acridine antibody binding to treated RBC measured as FACScan mean fluorescence. (PIC-1 is at 0.2 mM in all samples.)

| | | Quencher | | |
|---|---|---|---|---|
| Sample | Sequence of addition | mM | Eq. NaOH | Time delay (minutes) | Mean Fluorescence |
| 1a | PIC-1 + GSH | 2 | 0 | 0 | 151 |
| 1b | PIC-1 + GSH | 2 | 0 | 0 | 182 |
| 1c | PIC-1 + GSH | 2 | 0 | 0 | 160 |
| 2a | GSH/PIC-1 | 20 | 2 | 10 | 6.06 |
| 2b | GSH/PIC-1 | 20 | 2 | 10 | 5.62 |
| 2c | GSH/PIC-1 | 20 | 2 | 10 | 5.6 |
| 3 | Control Cys only | 20 | 2 | NA | 1.99 |
| 4 | Cys/PIC-1 | 2.5 | 0 | 10 | 44 |
| 5 | Cys/PIC-1 | 2.5 | 1 | 10 | 49.5 |
| 6 | Cys/PIC-1 | 2.5 | 2 | 10 | 49 |
| 7 | Cys/PIC-1 | 5 | 0 | 10 | 49 |
| 8 | Cys/PIC-1 | 5 | 1 | 10 | 19.28 |
| 9 | Cys/PIC-1 | 5 | 2 | 10 | 14.1 |
| 10 | Cys/PIC-1 | 10 | 0 | 10 | 11.6 |
| 11 | Cys/PIC-1 | 10 | 1 | 10 | 5.1 |
| 12 | Cys/PIC-1 | 10 | 2 | 10 | 3.6 |
| 13 | Cys/PIC-1 | 20 | 0 | 10 | 4.3 |
| 14 | Cys/PIC-1 | 20 | 1 | 10 | 2.5 |
| 15 | Cys/PIC-1 | 20 | 2 | 10 | ND |

EXAMPLE 6

Evaluation of the pH of a Red Blood Cell Composition upon Addition of PIC-1 and Various Quenchers The effect of various quenching conditions on the pH of a red blood cell composition was determined for various treatment conditions. The quencher solutions were prepared at a concentration of 600 mM in 8% dextrose monohydrate. For cysteine, a portion of the solution was mixed with either 1 or 2 equivalents of sodium hydroxide. Glutathione was assessed at 2 mM (acidic) or 20 mM (2 eq. of base). N-acetyl cysteine, methionine and peptide dimer cysteine-glycine (CysGly) were also assessed, where N-acetyl cysteine was neutralized with 1 equivalent of sodium hydroxide, methionine was neutralized with 1 or 2 equivalents of sodium hydroxide and CysGly was neutralized with 2 equivalents of sodium hydroxide. The pH of the quencher solution, either unmodified or neutralized, was measured using a standard Epoxy Calomel electrode (Beckman Instruments) at room temperature. A solution of PIC-1 was prepared at 6 mM in 8% dextrose monohydrate. A red blood cell composition was prepared as in Example 1. For each sample, 167 µL of quencher and 167 µL of PIC-1 were added sequentially to 4.67 mL of RBC, incubating at room temperature for 10 minutes after addition of the quencher, then adding PIC-1. The samples were mixed and the pH at room temperature was measured using the same electrode as described above. The results of various studies are shown in Table 10.

TABLE 10 pH measurements using various quencher conditions with 0.2 mM PIC-1 in RBC.

| Sample | Quencher conditions | pH of stock quencher | pH of final mixture |
|---|---|---|---|
| 1 | RBC no treatment control* | NA | 6.96 |
| 2 | 2 mM acidic glutathione* | 2.82 | 6.9 |
| 3 | 20 mM glutathione + 2 eq. base* | 9.5 | 7.7 |
| 4 | 20 mM cysteine | 5 | 6.5 |
| 5 | 20 mM cysteine + 1 eq. base | 9.9 | 7.4 |
| 6 | 20 mM cysteine + 2 eq. base | 11.5 | 7.8 |
| 7 | 20 mM N-acetyl cys + 1 eq. base | 6 | 6.7 |
| 8 | 20 mM CysGly + 2 eq. base | 8.5 | ND |
| 9 | 20 mM methionine + 2 eq. base | 13.1 | 8 |
| 10 | 20 mM methionine + 1 eq. base | 11.2 | 7.5 |

EXAMPLE 7

Quenching as a Function of Glutathione Concentration and Neutralization; Assessment of Anti-Acridine Antibody Binding and Inactivation of *S. epidermidis*

In these, the appropriate amount of 600 mM stock was added, mixed with an appropriate volume of 8% dextrose to provide the same volume addition to each RBC sample where in one study, with varied glutathione concentrations, the pH was measured after adding glutathione and after adding PIC-1. Note that the addition of PIC-1 lowers the pH of some of the solutions with higher pH values after addition of quencher, but the final pH is still in a preferred range for improved quenching, and are well above the pH values of the same concentration of glutathione with no neutralization. Samples prepared similarly to Example 6 with various concentrations of glutathione (Table 11A) were assessed for binding to anti-acridine rabbit sera, either by gel card or FACScan analysis. Similar samples were also assessed for the inactivation of *S. epidermidis*. Each RBC sample was treated with glutathione, followed 10 minutes later with PIC-1, then incubated at room temperature for 20 hours following mixing of the PIC-1. For gel card analysis, after incubation, the RBC were washed in BBS and were diluted in BBS to a final hematocrit of 4%. A 25 µL aliquot of each was mixed with 15 µL of rabbit polyclonal anti-acridine sera diluted either 1:4 or 1:100 in BBS and the mixture was incubated at 37° C. for 30 minutes. The cells were subsequently washed with 1.5 mL BBS. After washing was complete, the cells were mixed with goat anti-rabbit Fab'$_2$ fragment anti H+L chains (1:4 dilution in PBS) and incubated at 37° C. for 30 minutes. After incubation, the cells were washed again with 3×1.5 mL BBS and loaded onto a gel card and the cards centrifuged for 10 minutes at 900×g as per manufacturer's settings in an MTS Centrifuge™ (Ortho System, Pompano Beach, Fla.). The cards are scored on a scale of 0, 1+, 2+, 3+, 4+, grading the relative amount of agglutination, where 0 indicates no agglutination, all cells pass through the gel and 4+ indicates complete agglutination, all cells at the top of the gel. These results indicate that as the glutathione concentration is increased, it is necessary to adjust the pH of the RBC composition, such as using neutralized glutathione. Even at 5 mM, the glutathione neutralized with 2 equivalents of base provides better quenching than 5 mM with 1 or 0 equivalents of base. The neutralized glutathione shows reduction in antibody binding as the concentration is increased, whereas acidic glutathione shows little, if any, improvement at higher concentrations compared to the 2 mM standard condition. The sensitivity of this assay is such that, in this study, a 1:100 dilution of the rabbit sera is necessary to see the differences in the quenching methods, as the 1:4 dilution shows complete agglutination in all samples (untreated control shows no agglutination). As such, only the 1:100 diluted samples are shown in Table 11B. The results between studies vary depending on the blood sample used. For example, in this study, the 1:4 diluted anti-acridine rabbit sera resulted in 4+ scores for all samples, another study was done with 10, 15, and 20 mM of neutralized glutathione (2 eq. base) where the differences were observed in the 1:4 diluted samples while the 1:100 diluted samples all showed a score of 0. These samples tested at 1:4 dilution of the rabbit sera showed scores of 4+, 4+, 3+ and 1+ for standard condition, 10 mM, 15 mM and 20 mM neutralized (2 eq. or base) glutathione, respectively. A combination of neutralized glutathione (2 eq. of base) and neutralized cysteine (1 eq. of base) was also used, where the total quencher concentration was 20 mM, and all such samples resulted in scores of 1+ or 0 (i.e. they were at least as effective as 20 mM neutralized glutathione).

TABLE 11A pH measurements using various quencher conditions with 0.2 mM PIC-1 in RBC.

| Sample | Quencher conditions | pH of stock quencher | pH of mixture Post quencher | Final |
|---|---|---|---|---|
| 1 | RBC no treatment control* | NA | ND | 6.8 |
| 2 | 20 mM acidic glutathione |  | 6.1 | 6.1 |
| 3 | 10 mM acidic glutathione | 3.0 | 6.4 | 6.4 |
| 4 | 5 mM acidic glutathione |  | 6.6 | 6.6 |
| 5 | 2 mM acidic glutathione* |  | 6.7 | 6.7 |
| 6 | 20 mM glutathione + 1 eq. base |  | 6.7 | 6.7 |
| 7 | 10 mM glutathione + 1 eq. base | 6.1 | 6.7 | 6.7 |
| 8 | 5 mM glutathione + 1 eq. base |  | 6.7 | 6.7 |
| 9 | 2 mM glutathione + 1 eq. base |  | 6.8 | 6.8 |
| 10 | 20 mM glutathione + 2 eq. base* |  | 7.4 | 7.2 |
| 11 | 10 mM glutathione + 2 eq. base | 9.2 | 7.2 | 7.0 |
| 12 | 5 mM glutathione + 2 eq. base |  | 6.9 | 6.9 |
| 13 | 2 mM glutathione + 2 eq. base |  | 6.8 | 6.8 |

TABLE 11B

Anti-acridine antibody binding in RBC treated with varying concentrations of glutathione and 0.2 mM PIC-1. Gel card score for 1:100 dilution of anti-acridine rabbit sera and 1:4 dilution of secondary anti-rabbit IgG.

| Sample | Gel card score | | |
|---|---|---|---|
|  | No added base | 1 eq. base | 2 eq. base |
| 2 mM GSH | 3+ | 4+ | 3+ |
| 5 mM GSH | 3+/MX* | 3+ | 2+ |

TABLE 11B-continued

Anti-acridine antibody binding in RBC treated with varying concentrations of glutathione and 0.2 mM PIC-1. Gel card score for 1:100 dilution of anti-acridine rabbit sera and 1:4 dilution of secondary anti-rabbit IgG.

| Sample | Gel card score | | |
|---|---|---|---|
|  | No added base | 1 eq. base | 2 eq. base |
| 10 mM GSH | 3+/MX* | 2+ | 1+ |
| 20 mM GSH | 3+ | 1+ | 0 |

*MX = Mixed field

Another set of samples as shown in Table 11A were prepared as above using different unit of RBC and were assessed by FACScan analysis. These samples, following the 20 hour incubation, were treated as per Example 4 and analyzed by FACScan. An untreated control sample as well as a standard sample (co-addition of 2 mM acidic glutathione with 0.2 mM PIC-1) were also assessed. The results are shown in Table 11C.

TABLE 11C

Anti-acridine antibody (rabbit polyclonal; 1:100 dilution) binding in RBC treated with varying concentrations of glutathione and 0.2 mM PIC-1. Assessed by FACScan analysis using FITC labeled anti-rabbit Fab'$_2$ (1:64 dilution).

| Sample | Mean fluorescence | | |
|---|---|---|---|
|  | No added base | 1 eq. base | 2 eq. base |
| Untreated control | 4.62 | NA | NA |
| Co-addition std. | 144.33 | NA | NA |
| 2 mM GSH | 179.17 | 208.05 | 160.37 |
| 5 mM GSH | 95.57 | 87.6 | 67.56 |
| 10 mM GSH | 88.21 | 47.18 | 27.45 |
| 20 mM GSH | 187.74 | 29.97 | 13.37 |

Another set of samples as shown in Table 11A were prepared as above using the same unit of RBC and were spiked with *S. epidermidis* and assessed for titer as per Example 1. The results are shown in Table 1 ID. The combined results of antibody binding and inactivation of *S. epidermidis* demonstrate the improved quenching using neutralized glutathione at higher concentrations.

TABLE 11D

Inactivation of *S. epidermidis* in RBC treated with varying concentrations of glutathione and 0.2 mM PIC-1.

| Sample | Change in Log titer (initial RBC titer = 6.5) | | |
|---|---|---|---|
|  | No added base | 1 eq. base | 2 eq. base |
| Untreated control | 0 | NA | NA |
| 2 mM GSH | 6.5 | 6.5 | 6.5 |
| 5 mM GSH | 6.5 | 6.5 | 6.5 |
| 10 mM GSH | 2.9 | 6.5 | 6.5 |
| 20 mM GSH | 2.5 | 6.5 | 6.5 |

EXAMPLE 8

Assessment of Anti-Acridine Antibody Binding by Gel Card Analysis in Samples Quenched with Various Quenchers Similar studies using the gel card assay were done with other quenching conditions, such as with cysteine, cysteine-glycine dipeptide, or a combination of cysteine and glutathione. Samples were also tested with either the 1:4 or 1:100 dilution of the rabbit sera and no secondary antibody, which resulted in some agglutination for samples treated with the standard condition of 2 mM glutathione and 0.2 mM PIC-1 or with PIC-1 without quencher. The agglutination observed in almost all samples using the concentrated 1:4 dilution of rabbit sera with a secondary anti-rabbit antibody (Tables 12 and 13) are believed to be due, in part, to heterophile reactions. Heterophile antibodies are naturally occurring antibodies that recognize RBC from another species in a non-specific fashion. Tables 12-13 show the results of various experiments for either 1:4 or 1:100 dilution of rabbit sera and 1:4 dilution of anti-rabbit antibody. Data for untreated controls are not shown, as these gave a 0 score for all samples. All samples were mixed with quencher first, then PIC-1 at 0.2 mM. The quencher identity, concentration, and equivalents of base are indicated in the tables. These results suggest that a combination of glutathione and cysteine, or cysteine alone, may provide somewhat better quenching of the binding of PIC-1 to the RBC.

TABLE 12

Anti-acridine antibody binding in RBC treated with varying concentrations of glutathione and cysteine and 0.2 mM PIC-1.

| | | Gel card score | | | |
|---|---|---|---|---|---|
| | | No secondary Ab | | Secondary Ab 1:4 Dilution of rabbit sera: | |
| Sample | Quencher conditions | 1:4 | 1:100 | 1:4 | 1:100 |
| 1 | 2 mM acidic GSH | 3+ | 0 | 4+ | 4 |
| 2 | 20 mM GSH 2eq | 0 | 0 | 3+ | 0 |
| 3 | 2.5 mM Cys 1eq | 2+ | 0 | 4+ | 3 |
| 4 | 5 mM Cys 1eq | 1+ | 0 | 4+ | 1* |
| 5 | 10 mM Cys 1eq | 0 | 0 | 3+ | 0 |
| 6 | 15 mM Cys 1eq | 0 | 0 | 1* | 0 |
| 7 | 20 mM Cys 1eq | 0 | 0 | 0 | 0 |

*very slight color at top of gel.

TABLE 13

Anti-acridine antibody binding in RBC treated with varying concentrations of glutathione and cysteine and 0.2 mM PIC-1.

| | | Gel card score | | | |
|---|---|---|---|---|---|
| | | Blood sample 1 | | Blood sample 2 | |
| | | Dilution of rabbit sera: | | | |
| Sample | Quencher conditions | 1:4 | 1:100 | 1:4 | 1:100 |
| 1 | PIC-1 no quencher | 4+ | 4+ | 4+ | 4+ |
| 2 | 2 mM acidic GSH | 4+ | 4+ | 4+ | 4+ |
| 3 | 20 mM GSH 2eq | 4 | 0 | 4 | 0 |
| 4 | 15 mM GSH 2eq/5 mM Cys 1eq | 4 | 0 | 3 | 0 |
| 5 | 10 mM GSH 2eq/10 mM Cys 1eq | 3 | 0 | 3 | 0 |
| 6 | 5 mM GSH 2eq/15 mM Cys 1eq | 2 | 0 | 3 | 0 |
| 7 | 20 mM Cys 1eq | 0 | 0 | 3 | 0 |
| 8 | 15 mM GSH 2eq/5 mM Cys 2eq | 4 | 0 | 3 | 0 |
| 9 | 10 mM GSH 2eq/10 mM Cys 2eq | 2 | 0 | 2 | 0 |
| 10 | 5 mM GSH 2eq/15 mM Cys 2eq | 1 | 0 | 1 | 0 |
| 11 | 20 mM Cys 2eq | 0 | 0 | 1 | 0 |

The dipeptide cysteine-glycine (CysGly) was also used as a quencher. The standard condition as well as 20 mM neutralized cysteine (2 eq. of base) were compared to varying concentrations of the CysGly with and without 1 equivalent of base. The results are shown in Table 14. The results agree with those seen for both glutathione and cysteine, that as the amount of quencher is increased, adjustment of the pH, e.g. by neutralization of the quencher, is required for improved quenching.

TABLE 14

Comparison of quenching with CysGly with and without neutralization to 20 mM neutralized cysteine, or standard conditions.
Gel card analysis of anti-acridine antibody binding.

| | | Gel card score | |
|---|---|---|---|
| Sample | Quencher conditions | 1:4 dilution of serum | 1:100 dilution of serum |
| 1 | 2 mM acidic GSH | 4 | 4 |
| 2 | 2.5 mM CysGly | 4 | 3 |
| 3 | 2.5 mM CysGly 1 eq. base | 4 | 4 |
| 4 | 5 mM CysGly | 4 | 0 |
| 5 | 5 mM CysGly 1 eq. base | 4 | 2 |
| 6 | 10 mM CysGly | 4 | 0 |
| 7 | 10 mM CysGly 1 eq. base | 4 | 0 |
| 8 | 20 mM CysGly | 4 | 0 |
| 9 | 20 mM CysGly 1 eq. base | 4 | 0 |
| 10 | 20 mM Cys 2 eq base | 4 | 0 |
| 11 | Dextrose only, no treatment control | 2 | 0 |

EXAMPLE 9

Elimination of Cross Reactivity seen with Standard Treated Red Blood Cells by Treatment of Methods of the Present Invention The sera from patients that have developed antibodies that cross react to RBC that have been treated with 2 mM glutathione and 0.2 mM PIC-1 was used to assess cross reactivity with improved methods. Samples using O negative blood (Blood Source, Sacramento, Calif.), were prepared as described in Example 1 and treated with either 2 mM glutathione and 0.2 mM PIC-1, 0.2 mM PIC-1 followed 1 minute later by 20 mM neutralized glutathione (2 eq. base) or 20 mM neutralized glutathione followed 10 minutes later by 0.2 mM PIC-1. An untreated control RBC sample was also prepared. Each sample was washed with BBS three times, then suspended to a hematocrit of 8% in low ionic strength saline (AABB manual, 14$^{th}$ edition). A 50 µL aliquot of each was added to a gel card along with 25 µL of the patient sera, and the mixture was incubated at 37° C. for 15 minutes. The gel card contains rabbit anti-human IgG, which will agglutinate RBC that bind antibodies from the patient sera. The cards were centrifuged as per Example 7. The cards are read by the same scale as described in Example 7. Samples tested with three different sera showed a score of 3+ with the standard treated RBC and 0 with the control untreated or the 20 mM (2 equivalents) neutralized glutathione treated samples.

EXAMPLE 10

Use of Methionine as Model to Assess Quenching due to pH Adjustment Independently from Thiol Quenching Because methionine (Met) has a methyl substituent on the sulfur atom but is otherwise very similar to cysteine, it was used as a model amino acid to assess the effect of pH adjustment alone on quenching. The presence of the methyl group eliminates the nucleophilic nature of the sulfur atom, such that any quenching may be due to the increase in pH of the solution (e.g. the higher concentration of hydroxide may provide some quenching). The methionine (Aldrich) is used at 20 mM with 1 or 2 equivalents of base added, and compared to cysteine (1 or 2 eq.) and glutathione (2 eq.), all with 0.2 mM PIC-1, added 10 minutes after quencher. The standard condition was included, i.e. 0.2 mM PIC-1 and 2 mM acidic glutathione added together. Samples are assessed by gel card analysis of anti-acridine rabbit sera binding as per Example 7, with the exception that samples for gel card analysis were incubated at 37° C. or at room temperature. The results are shown in Table 15. The results show that methionine neutralized with 2 equivalents of base provides improved quenching compared to the standard condition.

TABLE 15

Quenching with methionine, cysteine or glutathione as assessed by anti-acridine rabbit sera binding gel card analysis.

| | | Gel card score Incubation temp.: | | | |
| | | 37° C. | | RT | |
| | | Rabbit sera dilution: | | | |
| Sample | Treatment | 1:4 | 1:100 | 1:4 | 1:100 |
| --- | --- | --- | --- | --- | --- |
| 1 | Untreated | 0 | 0 | 0 | 0 |
| 2 | 0.2 mM PIC-1/2 mM GSH | 4 | 3 | 4 | 3 |
| 3 | 20 mM GSH + 2 eq./0.2 mM PIC-1 | 3 | 0 | 3 | 0 |
| 4 | 20 mM Cys + 1 eq./0.2 mM PIC-1 | 1 | 0 | 2 | 0 |
| 5 | 20 mM Cys + 2 eq./0.2 mM PIC-1 | 0 | 0 | 1 | 0 |
| 6 | 20 mM Met + 1 eq./0.2 mM PIC-1 | 4 | 3 | 4 | 3 |
| 7 | 20 mM Met + 2 eq./0.2 mM PIC-1 | 3 | 0 | 3 | 0 |

EXAMPLE 11

In Vitro Functional Studies on Whole Units Treated with 20 mM Neutralized Glutathione and 0.2 mM PIC-1

Full units of red cell concentrates (Interstate Blood Bank, Inc., Memphis, Tenn.) were leukoreduced. A volume of 200 mL of this RCC (80% hematocrit) was mixed with 94 mL of Erythrosol or 100 mL of Adsol (Baxter Healthcare Corp., Deerfield, Ill.) as control (unit 1). A volume of 20 mL of 8% dextrose was used to dissolve PIC-1 (mg) and acid glutathione (mg) and added to one unit to provide 0.2 mM PIC-1 and 2 mM glutathione (unit 2). For units 3 and 4, PIC-1 (mg) and glutathione (mg) were dissolved separately in 10 mL or 8.8 mL of 8% dextrose, respectively. For the glutathione, 1.2 mL of 10 N NaOH was added (2 equivalents). The PIC-1 was mixed with the unit, followed 1 minute later (unit 3) or 5 minutes later (unit 4) by glutathione. For unit 5, neutralized glutathione was mixed first, followed 10 minutes later by the PIC-1. For unit 6, glutathione was dissolved in 18.8 mL 8% dextrose and mixed with 1.2 mL of 10N NaOH, then mixed with the RBC (no PIC-1). All units were mixed by grasping the ends of the blood bag and mixing in a FIG. 8 motion 30 times. These were then incubated at room temperature for 20 hours total. A compound adsorption device (CAD), comprising a polymeric resin contained within a mesh pouch, was used for all but the control sample. This device is intended to remove residual PIC-1, PIC-1 breakdown products, and glutathione from the samples. Samples were incubated for 8 hours, then transferred to a second blood bag containing the CAD and incubated for an additional 12 hours. Following the room temperature incubation, samples were transferred to a refrigerator (4° C.) and stored up to 43 days. Aliquots were removed from each unit 12 hours and 20 hours post mixing, and every week thereafter. Aliquots were analyzed for total hemoglobin, pH, intracellular ATP, plasma hemoglobin, potassium, extracellular glucose and extracellular lactate. The anti-rabbit sera binding was also assessed by FACScan analysis as described in Example 4. The study was repeated, with PIC-1 treated units treated with or without the CAD. The results for ATP, hemolysis and anti-rabbit sera binding are shown in Tables 16A-C and 17A-C.

Table 16A-C sample identities:
1: Untreated Control
2: Standard Treatment 0.2 mM PIC 1+2 mM GSH
3: 0.2 mM PIC-1, 1' delay, 20 mM GSH+2 equivalents of base
4: 0.2 mM PIC-1, 5' delay, 20 mM GSH+2 equivalents of base
5: 20 mM GSH+2 equivalents of base, 10' delay, 0.2 mM PIC-1
6: 0.2 mM GSH+2 equivalents of base

TABLE 16A

ATP data over 42 Days of storage.

| | RBC Sample ATP μmol/g Hb | | | | | |
| Days | 1 | 2 | 3 | 4 | 5 | 6 |
| --- | --- | --- | --- | --- | --- | --- |
| 0 | 3.66 | 3.62 | 4.20 | 4.16 | 4.11 | 4.30 |
| 0.5 | 3.79 | 3.85 | 2.02 | 5.08 | 5.17 | 5.56 |
| 0.8 | 3.77 | 3.55 | 5.05 | 5.38 | 5.21 | 5.56 |
| 7 | 3.63 | 3.59 | 5.24 | 5.11 | 5.58 | 5.64 |
| 14 | 2.84 | 2.58 | 4.20 | 4.06 | 4.22 | 4.93 |
| 22 | 2.69 | 2.30 | 3.86 | 3.66 | 3.90 | 4.20 |
| 28 | 2.24 | 1.61 | 3.10 | 2.72 | 3.27 | 3.68 |
| 35 | 1.99 | 1.46 | 2.71 | 2.47 | 2.68 | 3.30 |
| 43 | 1.65 | 1.21 | 2.28 | 2.06 | 2.28 | 2.61 |

TABLE 16B

Percent hemolysis over 42 Days of Storage.

| | RBC Sample Percent Hemolysis | | | | | |
| Days | 1 | 2 | 3 | 4 | 5 | 6 |
| --- | --- | --- | --- | --- | --- | --- |
| 0 | 0.16 | 0.22 | 0.19 | 0.19 | 0.19 | 0.15 |
| 0.5 | 0.18 | 0.24 | 0.16 | 0.25 | 0.24 | 0.19 |
| 0.8 | 0.18 | 0.46 | 0.40 | 0.48 | 0.47 | 0.51 |
| 7 | 0.27 | 0.62 | 0.35 | 0.52 | 0.57 | 0.58 |
| 14 | 0.37 | 0.69 | 0.50 | 0.52 | 0.55 | 0.61 |
| 22 | 0.46 | 0.87 | 0.59 | 0.62 | 0.63 | 0.60 |
| 28 | 0.62 | 0.86 | 0.63 | 0.64 | 0.65 | 0.71 |
| 35 | 0.73 | 0.99 | 0.74 | 0.76 | 0.71 | 0.70 |
| 43 | 0.84 | 1.17 | 0.82 | 0.90 | 0.83 | 0.75 |

TABLE 16C

RBC modification measured by anti-acridine antibody binding (FACScan) over 42 Days of Storage.

| | RBC Unit mean fluorescence | | | | | |
| Days | 1 | 2 | 3 | 4 | 5 | 6 |
| --- | --- | --- | --- | --- | --- | --- |
| 0.8 | 1.67 | 284 | 20.1 | 46.0 | 20.0 | 2.16 |
| 2 | 1.84 | 193.5 | 14.58 | 34.07 | 12.31 | 1.78 |
| 7 | 1.72 | 142.1 | 4.96 | 18.84 | 5.34 | 1.58 |
| 14 | 1.56 | 135.7 | 4.09 | 8.41 | 3.29 | 1.48 |
| 22 | 1.61 | 90.8 | 2.61 | 4.46 | 2.12 | 1.58 |
| 28 | 1.95 | 128.7 | 2.6 | 5.69 | 2.83 | 2.02 |
| 35 | 2.71 | 153.4 | 2.74 | 6.71 | 2.58 | 1.62 |
| 43 | 1.63 | 136.1 | 2.43 | 4.51 | 2.46 | 1.8 |

Table 17A-C sample identities:
1: Standard Treatment, 0.2 mM PIC-1, 2 mM GSH+CAD
2; Standard Treatment, 0.2 mM PIC-1, 2 mM GSH
3: 0.2 mM PIC-1, 1' delay, 20 mM neutralized GSH+CAD
4: 0.2 mM PIC-1, 1' delay, 20 mM neutralized GSH
5: 20 mM neutralized GSH, 10' delay, 0.2 mM PIC-1+CAD
6: 20 mM nGSH, 10' delay, 0.2 mM PIC-1
7: 20 mM neutralized GSH
8: Untreated Control

TABLE 17A

Intracellular ATP values over 42 Days of Storage.

RBC Sample ATP µmol/g Hb

| Days | 1 | 2 | 3 | 4 | 5 | 6 | 7 | 8 |
|---|---|---|---|---|---|---|---|---|
| 0.0 | 4.02 | 4.38 | 5.21 | 4.86 | 4.93 | 4.82 | 5.17 | 4.46 |
| 0.5 | 4.63 | 4.78 | 6.78 | 6.60 | 6.92 | 6.56 | 6.54 | 4.28 |
| 0.8 | 4.58 | 4.69 | 6.37 | 6.31 | 6.58 | 6.45 | 6.41 | 4.55 |
| 7 | 3.55 | 3.77 | 5.21 | 5.80 | 6.04 | 6.12 | 6.15 | 3.59 |
| 14 | 2.38 | 2.54 | 4.24 | 4.36 | 4.44 | 4.62 | 4.86 | 2.74 |
| 28 | 1.51 | 1.67 | 3.00 | 3.11 | 3.16 | 3.44 | 3.21 | 2.15 |
| 35 | 0.79 | 0.76 | 1.37 | 1.50 | 1.53 | 1.65 | 1.64 | 1.04 |
| 42 | 1.01 | 1.12 | 2.01 | 2.14 | 2.13 | 2.34 | 2.16 | 1.58 |

TABLE 17B

Percent Hemolysis over 42 Days of Storage.

RBC Unit Percent Hemolysis

| Days | 1 | 2 | 3 | 4 | 5 | 6 | 7 | 8 |
|---|---|---|---|---|---|---|---|---|
| 0.0 | 0.22 | 0.22 | 0.16 | 0.18 | 0.21 | 0.21 | 0.16 | 0.17 |
| 0.5 | 0.27 | 0.22 | 0.22 | 0.20 | 0.28 | 0.27 | 0.19 | 0.17 |
| 0.8 | 0.42 | 0.25 | 0.43 | 0.21 | 0.48 | 0.30 | 0.19 | 0.20 |
| 7 | 0.54 | 0.34 | 0.48 | 0.31 | 0.57 | 0.44 | 0.29 | 0.32 |
| 14 | 0.78 | 0.51 | 0.56 | 0.35 | 0.61 | 0.42 | 0.29 | 0.42 |
| 28 | 1.10 | 0.78 | 0.75 | 0.47 | 0.78 | 0.60 | 0.48 | 0.74 |
| 35 | 1.31 | 0.92 | 0.86 | 0.53 | 0.96 | 0.66 | 0.61 | 0.86 |
| 42 | 1.62 | 1.10 | 1.09 | 0.76 | 1.13 | 0.81 | 0.78 | 1.20 |

TABLE 17C

RBC modification measured by anti-acridine antibody binding (FACScan) over 42 Days of Storage.

RBC Unit mean fluorescence

| Days | 1 | 2 | 3 | 4 | 5 | 6 | 7 | 8 |
|---|---|---|---|---|---|---|---|---|
| 4 | 148.1 | 62.6 | 11.3 | 5.24 | 5.33 | 4.56 | 1.94 | 1.55 |
| 7 | 181.6 | 81.4 | 9.03 | 4.12 | 6.01 | 4.05 | 1.47 | 1.45 |
| 14 | 115.9 | 46.7 | 3.73 | 3.09 | 2.77 | 3.74 | 1.95 | 1.49 |
| 21 | 133.0 | 48.6 | 3.00 | 3.40 | 2.65 | 3.51 | 1.73 | 1.65 |
| 28 | 134.4 | 46.7 | 4.59 | 4.94 | 2.72 | 5.16 | 1.96 | 2.61 |
| 35 | 143.3 | 44.51 | 2.8 | 3.98 | 2.22 | 4.51 | 1.86 | 1.85 |
| 42 | 132.4 | 44.1 | 3.32 | 5.00 | 2.66 | 5.28 | 2.02 | 2.04 |

EXAMPLE 12

In Vivo Assessment of Immunoreactivity of Treated Red Blood Cells in Rabbit Model The in vivo assessment of the immunoreactivity of red blood cells (RBC) that have been treated with S-303 using one, nonlimiting example of an improved quenching method, referred to in this example as the "Modified S-303 RBC," was conducted using an allogeneic transfusion model. (See below for the description of the protocol for Modified S-303 RBC.) The allogeneic transfusion model used was based on a rabbit model described by Ness et al. (*Trans Med Rev,* 2001, 15: 305-17) to investigate the mechanisms for delayed hemolytic transfusion reactions. In that model, HgD-positive red cells were used to immunize HgD-negative recipient animals. However, consistent with the literature that HgD-mismatched RBC only cause antibody formation infrequently, Ness et al. resorted to subcutaneous administration of HgD-positive RBC combined with adjuvant in order to generate appreciable titers of anti-HgD antibody.

The assessment was conducted in two phases: In Phase 1, rabbits were repetitively transfused with allogeneic rabbit RBC, mismatched at the HgD locus and treated with the Original S-303 process (see description below). The endpoint of Phase 1 was to determine whether an antibody response could be generated against Original S-303 RBC in the context of chronic allogeneic transfusions. In Phase 2, rabbits were conventionally immunized with KLH-Acridine conjugate in adjuvant in order to stimulate formation of anti-acridine antibodies. These immunized animals were then transfused with S-303 RBC. The endpoint of Phase 2 was to compare recovery and lifespan of RBCs prepared by the Original and Modified S-303 RBC processes. Control samples in the Phase 1 and Phase 2 experiments included S-220 RBC prepared by the original and modified processes. S-220 is a non-labile version of S-303 that should represent a worst-case in terms of acridine binding to RBCs for each treatment process. The results of these studies demonstrate that Modified S-303 are not affected by the presence of high titer antibody in vivo.

A. Materials and Methods

Animal Husbandry: New Zealand White rabbits, males and females, were approximately 5 to 7 months of age and weighed between 3.5 to 4.5 kg at the initiation of the study. Donor animals were HgD-positive; recipients were HgD-negative.

Reagents. Erythrosol without dextrose was manufactured by Baxter Healthcare according to the formulation in Table 18. A solution of 8% dextrose monohydrate was also made by Baxter.

TABLE 18

The composition of Erythrosol (without dextrose)

| Ingredient | Concentration (mg/100 mL) |
|---|---|
| Sodium citrate dehydrate | 782 |
| Adenine | 21.5 |
| Mannitol | 774 |
| Sodium dihydrogen phosphate dihydrate | 73.4 |
| Dibasic sodium phosphate, anhydrous | 242 |

The pathogen-inactivating compound used in this example was PIC-1 which is referred in this example as S-303. S-303.2HCl was sterilized by gamma irradiation. A non-frangible analogue of S-303, called S-220 was utilized as a control. The chemical structures of S-303 (also referred to herein as "PIC-1") and S-220 are as follows:

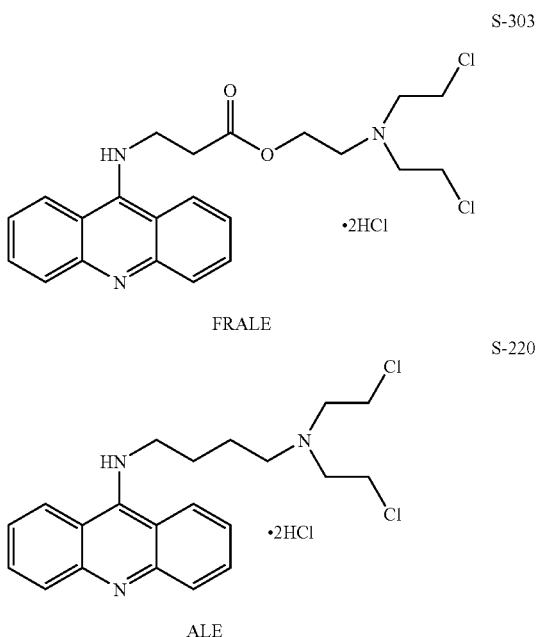

FRALE

ALE

The two compounds have very similar structures with the exception of the frangible ester bond present only in S-303. S-303 is sometimes referred to herein as a Frangible Anchor Linker Effector compound (FRALE) and S220 as an Anchor Linker Effector compound (ALE).

GSH was provided in one of two ways: as a pre-weighed powder of 184 mg sterilized by gamma irradiation (Baxter Healthcare) or as a bulk substance (Aldrich, St. Louis Mo.) to be weighed and formulated at the time of RBC treatment.

RBC Treatment: RBC were transfused within 24-36 hours of preparation. Blood was collected aseptically from HgD-positive donors in ACD-A. Approximately 410 to 500 mL of whole blood was pooled into a plastic container and centrifuged at 4200×g for 6 minutes. After removing the plasma, 94 mL of Erythrosol without dextrose was added to yield a packed red cell preparation with a hematocrit of approximately 60%. The packed red cells were treated in one of three ways as shown in FIG. 2 and described below.

Control RBC: Packed red cells were mixed with 20 mL of 8% dextrose and then stored at 4° C. prior to infusion (up to 2 days).

Original S-303 RBC: GSH (184 mg) was dissolved in 20 mL of 8% dextrose. This GSH solution (pH 2.8-3.0) was then used to dissolve S-303.2HCl (33 mg). The S-303/GSH solution was subsequently added to the packed red cells and mixed manually. RBC were incubated for 12 h at room temperature, and then exposed to a compound adsorption device (CAD) for an additional 8 h with mixing. The final concentrations of S-303 and GSH in the original process were 0.2 mM and 2.0 mM, respectively. Original S-303 RBC were then stored at 4° C. prior to infusion. Treatments with the original process were performed using the same disposable kit used in human clinical studies.

Modified S-303 RBC: GSH.HCl (2026 mg) was weighed into sterile plastic tubes and dissolved in 9.32 mL of 8% dextrose. The acidic GSH was then combined with 1.32 mL 10 N NaOH, which represents 2 equivalents of base. 10 mL of sterile filtered, basic GSH in dextrose (pH 9) was added to the packed red cells and mixed manually. Within 10 min, S-303.2HCl (33 mg) was separately dissolved in 10 mL of 8% dextrose, added to the packed red cells containing GSH, and mixed manually. Modified S-303 RBC were incubated at room temperature and exposed to CAD in a manner identical to the original process. The final concentrations of S-303 and GSH in the modified process were 0.2 mM and 20 mM, respectively.

S-220 RBC: S-220 is an analogue of S-303 lacking the labile ester, and thus the acridine cannot be cleaved by hydrolysis from the rest of the molecule during RBC treatment. S-220 RBC were prepared using methods analogous to the original or modified process described for S-303, and disposables from the original process were used whenever possible. For Original S-220 RBC, final concentrations of S-220 and GSH were 0.2 mM and 2.0 mM, respectively. For Modified S-220 RBC, final concentrations of S-220 and GSH were 0.2 mM and 20 mM, respectively.

Acridine Immunization: To elicit high titer anti-acridine antibodies, rabbits were immunized in Phase 2 with a KLH-Acridine conjugate. KLH-Acridine was prepared on a 2-5 mL scale by reacting equimolar amounts (476 μM) of KLH (Pierce Biotechnology, Ill.) and S-220 in phosphate buffered saline (pH 7.4) for 48 hours at room temperature. The small molecule degradation products of S-220 were separated from KLH-Acridine by passing through a desalting column. The KLH-Acridine conjugate was characterized by its absorption at 210 and 410 nm, and the ratio of acridine to KLH was determined using the extinction coefficient of S-220. Typically 200-400 acridine adducts were formed per molecule of KLH. The KLH-Acridine solution was refrigerated until use. Rabbits were immunized on day 1 with KLH-Acridine in Complete Freund's Adjuvant (0.5 mg/mL) subcutaneously at 10 sites above the popliteal, pre-scapular and pre-femoral lymph nodes (approximately 0.1 mL per site). On days 8, 15, 36 and 64, animals were boosted with KLH-Acridine in Freund's Incomplete Adjuvant (0.25 mg/mL) at the same sites (approximately 0.1 mL per site). Rabbit serum samples were tested biweekly for the formation of antibodies.

Detection of Antibody to Acridine (Phase 1): Antibody to acridine was detected using a flow cytometry assay. Human S-303 RBC were prepared as a test reagent using the original treatment process. Rabbit serum was diluted 1:4 and 25 μL of the diluted serum was mixed with 50 μL of human S-303 RBC at 0.8% hematocrit. Pre-immunization sera were tested as negative controls. Samples were incubated for 30 min at 37° C. and then washed and resuspended in 50 μL of blood bank saline. FITC-labeled goat anti-rabbit IgG (supplier) was diluted 1:64 and 25 μL was incubated with the RBC sample for 30 min at 37° C. Samples were again washed and analyzed by FACS using the FL1 channel to detect bound antibody complex. Once a positive serum was identified, the same procedure was performed with dilutions of rabbit serum to determine the endpoint titer.

Detection of Antibody to Acridine (Phase 2): Human S-303 RBC were prepared as a test reagent using the original treatment process (0.2 μM S-303, 2 mM GSH). RBCs were washed thrice in blood bank saline (BBS, Fisher Scientific) and diluted, in BBS, to approximately 4% hematocrit. Sera from Group V and VI rabbits were serially diluted in BBS. 25 μl of 4% RBC were combined with 15 μl of rabbit serum and allowed to incubate for 30 min at 37° C. BBS was used in place of serum for negative control. After incubation RBC were washed thrice in BBS and then resuspended in 50 μl FITC conjugated Goat F(ab')$_2$ anti-rabbit IgG (H&L) (Caltag) diluted 1:64 in BBS. RBC were incubated for 30 min at 37° C. and washed three times with BBS. Samples were then resuspended 1 ml HaemaLine-2 (HL2, Sereno Diagnostics).

Samples were analyzed by FACS using the FL1 channel to detect bound antibody complex.

RBC Infusions and RBC Lifespan Measurements: RBCs were administered intravenously via the ear vein at 1 mL/min using transfusion pumps. In Phase 1, rabbits were dosed with 10 mL RBC/kg, while in Phase 2, rabbits were dosed with 4 mL RBC/kg. The 10 mL/kg dose corresponds to the approximate amount of blood transfused monthly in regimens for sickle cell and thallasemia patients.

Biotinylation of RBC was carried out after treatment with either S-303 or S-220. RBCs (300 mL) were washed twice with 200 mL PBSG (12 mM phosphate, 138 mM NaCl, 2.7 mM KCl, 5 mM glucose, pH 7.4) and resuspended in the same medium. They were then mixed with an equal volume of PBSG containing 60 µM NHS-biotin (Aldrich, St Louis Mo.) and incubated for 1 h at 37° C. After incubation, they were washed three times with 200 mL PBSG and were finally resuspended in PBSG at 50% hematocrit and stored refrigerated until transfusion.

Lifespan of RBCs was assessed by FACScan analysis. Rabbit blood was obtained at regular intervals after transfusion (1, 3, 7, 15, 21 and 28 days) from all animals. Samples were passed through an 80 micron filter to remove microclots, diluted to 0.07% HCT in PBSG and incubated with phycoerythrin-labeled Streptavidin (1:100 dilution, Molecular Probes) in the dark at room temperature for 20 minutes. FACS analysis was performed on samples that were diluted 5-fold, and 50,000 total events were collected at a rate of 400 events/sec to enable accurate cell quantitation. The lifespan of biotinylated RBC was calculated by extrapolating to 100% recovery at day 0. Values on subsequent days were then expressed as a percent of the day 0 value. When appropriate, the statistical significance of lifespan differences was analyzed using the Student t-test with a heteroskedastic analysis.

B. Phase 1: Repeated Infusions of Mismatched RBC

In Phase 1, animals were transfused biweekly for 24 weeks with 10 mL/kg allogeneic RBC mismatched at the HgD locus in order to determine whether a response to S-303 RBC could be detected. Cohorts of animals are described in Table 19.

TABLE 19

Animal Cohorts in Phase 1

| Cohort | Number | Immunization Regimen |
|---|---|---|
| Group 1 | 4 | Control RBC, intravenous |
| Group 2 | 6 | Original Process S-303 RBC, intravenous |
| Group 3 | 2 | KLH-Acridine conjugate, subcutaneous |
| Group 4 | 6 | Original Process S-220 RBC, intravenous |

Serum was sampled at weekly intervals and tested in a flow cytometry-based assay for the presence of anti-acridine antibody. Briefly, human S-303 RBC prepared by the original process (0.2 mM S-303 and 2 mM GSH) were incubated with a 1:4 dilution of rabbit serum. After washing, the presence of bound rabbit antibody was detected with a goat anti-rabbit IgG labeled with FITC. The only positive result was detected in group 3 at the 1:4 dilution. Results through 24 weeks of infusion are shown in FIG. 1. The animals immunized with KLH-Acridine demonstrated a robust anti-acridine antibody response. In contrast, there was no significant antibody response in the animals repeatedly transfused with the S-303 or S-220 RBC prepared by the original process.

The results shown in FIG. 1 were confirmed by performing agglutination assays with human S-303 RBC treated with the original process for most serum samples. Only sera from Group 3 animals immunized with KLH-Acridine were shown to agglutinate human S-303 RBC. In addition, we did not observe an anti-HgD response in any recipient animals.

C. Phase 2: Determination of RBC Lifespan in Rabbits Immunized with KLH-Acridine Since repeated infusions with S-303 or S-220 treated, antigen-mismatched RBC preparations failed to generate an anti-acridine immune response, in Phase 2, a more stringent approach was taken to elicit anti-acridine antibody. Animals were immunized with KLH-Acridine using a conventional prime-boost regimen including adjuvant and the in vivo lifespan of various treated RBC preparations in rabbits or high-titer antibody was then measured. The results from Phase 1 demonstrated that it was feasible to immunize rabbits via subcutaneous immunization with KLH-Acridine and high achieve antibody titers.

Animals in Groups 1, 2 and 4 were also utilized in Phase 2. These groups were subdivided, and a subset of animals was immunized with KLH-Acridine, while the remainder were maintained on their existing transfusion regimen. Two additional cohorts of HgD-negative rabbits that were naive to RBC infusions of any type were added to Phase 2. A description of the experimental cohorts in Phase 2 is provided in Table 20.

TABLE 20

Animal Cohorts in Phase 2

| Group | Number | Phase 1 Immunization | Phase 2 Immunization |
|---|---|---|---|
| 1A | 2 | Control RBC | Control RBC |
| 1B | 2 | Control RBC | KLH-Acridine |
| 2A | 2 | Original S-303 RBC | Original S-303 RBC |
| 2B | 4 | Original S-303 RBC | KLH-Acridine |
| 4A | 2 | Original S-220 RBC | Original S-220 RBC |
| 4B | 4 | Original S-220 RBC | KLH-Acridine |
| 5 | 6 | None | KLH-Acridine |
| 6 | 6 | None | KLH-Acridine |

During the immunizations in Phase 2, antibody production was followed weekly by the same FACS and agglutination assays used in Phase 1. After approximately 8 weeks, all rabbits immunized with KLH-Acridine developed a strong antibody response specific for human S-303 RBC, while the serum from animals immunized with the various RBC preparations continued to be non-reactive.

The anti-Acridine antibody titer in sera from Groups V and VI was determined. Flow Cytometry analysis was used to titrate sera samples from pre-transfusion 1 (Original processed RBCs) and pre-transfusion 2 (Modified processed RBCs) animals in groups V and VI. Group V animals received RBCs treated with S-303, whereas Group VI animals were transfused with S-220 treated RBCs.

The titer was defined as the dilution of serum in which the mean fluorescence was above background. All rabbits had high titer anti-Acridine antibodies. The titer for Group V was slightly lower in sera taken from prior to Transfusion 1 ("Pre-T1") compared to pre-transfusion 2 sera ("Pre-T2". Group VI titer was the same prior to both transfusions.

TABLE 21

Average endpoint titer/group prior to Transfusion 1 and Transfusion 2

| | Pre-T1 | Pre-T2 |
|---|---|---|
| Group V | 1:2048 | 1:4096 |
| Group VI | 1:4096 | 1:4096 |

Once serum antibody was established by KLH-Acridine immunization, each animal was transfused to determine the in vivo lifespan of various RBC preparations. A biotin label was used to follow the in vivo circulation of RBC (Suzuki and Dale (1987) *Blood* 70:791-5). NHS-biotin forms a covalent attachment to RBC membrane proteins, and can be detected using fluorescently labeled streptavidin. Rabbits received approximately 4 mL RBC/kg according to the scheme in Table 22. After transfusion on day 0, blood was drawn on days 1, 3, 7, 15, 21 and 28 to measure the percentage of biotin-labeled cells in circulation relative to day 0. Test RBCs were either untreated Control RBC, S-303 RBC prepared using the original or modified procedure, or S-220 RBC prepared using the original or modified procedure as shown in Table 22.

TABLE 22

Transfusions to Determine RBC LIfespan by Animal Cohort

| Group | Acridine Antibody | Transfusion 1* | Transfusion 2* |
|---|---|---|---|
| 1A | No | Control RBC | Control RBC |
| 1B | Yes | Control RBC | Control RBC |
| 2A | No | Original S-303 RBC | Modified S-303 RBC |
| 2B | Yes | Original S-303 RBC | Modified S-303 RBC |
| 4A | No | Original S-220 RBC | Modified S-220 RBC |
| 4B | Yes | Original S-220 RBC | Modified S-220 RBC |
| 5 | 6 | Original S-303 RBC | Modified S-303 RBC |
| 6 | 6 | Original S-220 RBC | Modified S-220 RBC |

*All RBC Preparations were biotin labeled prior to infusion

Lifespan of RBC Prepared by the Original Process: Survival of Control RBC was measured in non-immune and acridine-immune rabbits (subgroups 1A and 1B, respectively, Table 21). Since there was no difference in RBC lifespan between these subgroups, data are presented graphically below as the mean percent recovery for all four animals combined. Animals receiving Control RBC were used as a comparator for all the other groups.

Groups 4 and 6 received S-220 RBC prepared by the original process in Transfusion 1. S-220 was used because it represents the "worst case" for hapten formation. The acridine cannot hydrolyze either during in vitro treatment or subsequently during circulation in vivo. Group 4A and 4B had been transfused with Original S-220 RBC in Phase 1 of the study, whereas Group 6 was naive to S-220 RBC (Table 20). There was a striking difference in the lifespan of Original S-220 RBC depending on the immunization history of the animals (FIG. 2). Group 1 animals, receiving Control RBC, had the longest RBC lifespan and biotinylated RBC could be detected in circulation at day 57. Clearance of Control RBC was approximately linear with time. In contrast, Group 6, immunized with KLH-Acridine and which had never been transfused with S-220 RBC, demonstrated rapid clearance of Original S-220 RBC. Essentially no S-220 RBC were detectable on day 20. This demonstrates that rabbits in Group 4B, which had been immunized by the KLH-Acridine procedure, but unlike Group 6, had also been repetitively transfused with Original S-220 RBC in Phase 1, showed significantly longer RBC survival. Nevertheless, the lifespan of Original S-220 in Group 4B was decreased compared to Group 4A (which had not been immunized with KLH-Acridine). The RBC lifespan measured in Group 1 (receiving control RBC) and Group 4A (receiving Original S-220 RBC) was comparable, although a greater percentage of Control RBC were circulating in Group 1 beyond three weeks.

A similar comparison was made by measuring the lifespan of Original S-303 RBC in Groups 2A, 2B and 5 (FIG. 3). The shortest lifespan was observed for S-303 RBC in Group 5 rabbits, which were immunized to KLH-Acridine and were naive to S-303 RBC. Unlike Group 6, however, Original S-303 RBC were not cleared by day 20 and biotinylated S-303 RBC could be detected out to day 57. Interestingly, the lifespan of Original S-303 RBC in Group 2B rabbits, which had a high level of circulating anti-acridine antibody, was not measurably different from Group 1 receiving Control RBC. In comparing results for Groups 2B and Group 5 rabbits, it appears that prior exposure to Original S-303 RBC ameliorated the effects of the anti-acridine antibody on RBC clearance. This unexpected result is similar to what was observed for Groups 4B and 6 using Original S-220 RBC (FIG. 2).

Lifespan of RBC Prepared by the Modified Process: The modified process was developed to improve the quenching by GSH, by changing multiple parameters. First, the amount of GSH was increased 10-fold. Second, the GSH was titrated with NaOH prior to addition to the RBC; this improves the nucleophilicity of the —SH group. These changes lead to a significant reduction of S-303 bound to the RBC surface (see, e.g., Example 5 and Example 13). Modified S-220 RBC were prepared using the same approach.

The lifespan of Modified S-220 RBC was evaluated in Groups 4A, 4B and 6 (FIG. 4). As observed previously for S-220 RBC prepared with the original process, the lifespan of Modified S-220 RBC in Group 6 animals was significantly reduced compared to control RBC transfused in Group 1 animals. However, the decrease in circulation of Modified S-220 RBC over time was significantly less than observed in the same animals with Original S-220 RBC. For example, a mean of 18 percent of Modified RBC were circulating on day 14, whereas only 1.4% of Original RBC were observed at the same timepoint. In addition, the lifespan of Modified S-220 RBC in Groups 4A (no antibody) and 4B (KLH-Acridine induced antibody) were equivalent to or better than Control RBC in Group 1. Consistent with previous data (FIG. 3), previous exposure to Original S-220 RBC appears to have increased the lifespan of S-220 RBC even in the presence of high titer antibody.

Lastly, the lifespan of Modified S-303 RBC in Groups 2A, 2B and 5 is presented in FIG. 5. In all cases, the lifespan of Modified S-303 RBC was comparable to Control RBC. This was the case even for Group 5 animals, which had demonstrated increased clearance of Original S-303 RBC. This important data supports the in vitro finding that S-303-treated RBCs prepared by the Modified Process are not immunoreactive in vitro with anti-acridine antibody derived from several sources. This includes patient sera, murine monoclonal antibody, and rabbit polyclonal antisera.

EXAMPLE 13

Additional FACScan Analysis of S-303 Treated RBC

For flow cytometry testing of RBC for S-303 (PIC-1) binding, 50 μL of blood was washed three times in 1.2 mL of 0.9% saline, and then resuspended in 0.75 mL saline to approximately 4% hematocrit. Twenty-five μL of RBC were combined with 15 μL of anti-acridine rabbit serum that had been diluted 1:100. After incubation for 30 min at 37° C., the sample was washed three times as above. The RBC pellet was then resuspended in a 50 μL volume of FITC-labeled goat anti-rabbit antibody (Caltag) that had been prepared at 1:64 dilution in 0.1% bovine serum albumin. Samples were incubated in the dark for 30 min at 37° C. After three additional washes, the RBC were resuspended in 1 mL HaemaLine-2 (Serono Diagnostics). After diluting to 0.01% hematocrit, 20,000 events were collected and analyzed for fluorescence at 600 nm.

The modified process results in significantly lower levels of binding of S-303 to the RBC surface, as detected using a flow cytometry assay. S-303 bound to RBC was detected using a polyclonal rabbit antiserum, made by immunizing rabbits with a KLH-Acridine conjugate in adjuvant. Bound rabbit IgG was then detected using a FITC-labeled goat anti-rabbit IgG. FACScan results are shown for nine separate pools of RBC prepared using the original and modified process in FIG. 6. For each pool, the FACScan assay was used to detect S-303 binding to C-RBC, O-RBC and M-RBC. Binding of S-303 to the RBC surface was reduced between 15- to 35-fold by the modified process relative to the original process.

It is understood that the examples and embodiments described herein are for illustrative purposes only and that various modifications or changes in light thereof will be suggested to persons skilled in the art and are to be included within the spirit and purview of this application.

All publications, patents, patent applications, and accession numbers (including both polynucleotide and polypeptide sequences) cited herein are hereby incorporated by reference herein their entirety for all purposes to the same extent as if each individual publication, patent, patent application or accession number were specifically and individually indicated to be so incorporated by reference.

I claim:

1. A method of treating a red blood cell composition which contains a red blood cell concentrate in a buffered additive solution, comprising:
    (a) mixing a quencher with a base, wherein the quencher comprises a thiol group and an acid group, and is capable of quenching an undesired side reaction of a pathogen-inactivating compound with the red blood cells,
    (b) mixing the quencher and base of step (a) with the red blood cell composition,
    (c) mixing a pathogen-inactivating compound with the red blood cell composition, wherein the pathogen-inactivating compound contains a nucleic acid binding group and a functional group which is an electrophilic group or is capable of forming an electrophilic group, wherein the electrophilic group is capable of reacting with nucleic acid,
    wherein the molar ratio of the quencher to pathogen-inactivating compound is about 10:1 to about 400:1, wherein the quencher is in a final concentration following step (c) of about 2 mM to about 40 mM, and wherein the base is in a molar ratio with the quencher of at least about 1, so that the undesired side reaction is decreased in comparison with the treatment method of a red blood cell composition without mixing of the base with the quencher.

2. The method of claim 1, wherein the undesired side reaction of the pathogen-inactivating compound with the red blood cells is modification of the surface of the red blood cells by the pathogen-inactivating compound.

3. The method of claim 1, wherein both the base and the quencher are mixed with the red blood cell composition prior to, at the same time, or no more than about 30 minutes after mixing the pathogen-inactivating compound with the red blood cell composition.

4. The method of claim 3, wherein both the base and the quencher are mixed with the red blood cell composition prior to mixing the pathogen-inactivating compound with the red blood cell composition.

5. The method of claim 1, wherein the base is NaOH.

6. The method of claim 1, wherein the base is a basic buffer.

7. The method of claim 1, wherein the quencher is in a final concentration following step (c) of about 10 mM to about 30 mM.

8. The method of claim 1, wherein the resulting mixture comprising the red blood cell composition, the pathogen-inactivating compound, the quencher, and the base has a pH at room temperature of about 6.7.

9. The method of claim 1, wherein the resulting mixture comprising the red blood cell composition, the pathogen-inactivating compound, the quencher, and the base has a pH at room temperature of about 6.7 or higher.

10. The method of claim 1, wherein the resulting mixture comprising the red blood cell composition, the pathogen-inactivating compound, the quencher, and the base has a pH at room temperature of about 7.0 to 8.5.

11. The method of claim 1, wherein the quencher comprises cysteine or a derivative of cysteine.

12. The method of claim 11, wherein the quencher is glutathione.

13. The method of claim 1, wherein the functional group is selected from the group consisting of a mustard, a mustard intermediate, and a mustard equivalent.

14. The method of claim 13, wherein the pathogen-inactivating compound is β-alanine, N-(acridin-9-yl), 2-[bis(2-chloroethyl)amino]ethyl ester.

15. The method of claim 1, wherein the treatment results in an inactivation of at least 1 log of a pathogen contaminant in the red blood cell composition.

16. The method of claim 1, further comprising a step of reducing the concentration of the pathogen-inactivating compound in the resulting mixture comprising the red blood cell composition, the pathogen-inactivating compound, the quencher, and the base.

17. The method of claim 1, wherein the base is in a molar ratio with the quencher of about 1.

18. The method of claim 1, wherein the level of anti-pathogen inactivating compound antibody binding to the treated red blood cell composition in the resulting mixture which comprises the red blood cell composition, the pathogen-inactivating compound, the quencher, and the base, is reduced by at least about 25% relative to the mixture without the base.

19. The method of claim 18, wherein the level of anti-pathogen inactivating compound antibody binding to the treated red blood cell composition in the resulting mixture is reduced by at least about 50% relative to the mixture without the base.

20. The method of claim 19, wherein the level of anti-pathogen inactivating compound antibody binding to the treated red blood cell composition in the resulting mixture is reduced by at least about 75% relative to the mixture without the base.

* * * * *

UNITED STATES PATENT AND TRADEMARK OFFICE
CERTIFICATE OF CORRECTION

PATENT NO. : 7,655,392 B2  Page 1 of 1
APPLICATION NO. : 11/264195
DATED : February 2, 2010
INVENTOR(S) : Adonis Stassinopoulos It is certified that error appears in the above-identified patent and that said Letters Patent is hereby corrected as shown below:

On page 1, under the title, please insert:

--STATEMENT OF RIGHTS TO INVENTIONS MADE UNDER FEDERALLY SPONSORED RESEARCH

This invention was made with Government support of Grant No. DAMD17-03-2-0039 awarded by the USA Medical Research and Command. The Government has certain rights in this invention.--

Signed and Sealed this

Ninth Day of November, 2010

David J. Kappos
*Director of the United States Patent and Trademark Office*